US010689335B2

(12) United States Patent
Wang et al.

(10) Patent No.: US 10,689,335 B2
(45) Date of Patent: Jun. 23, 2020

(54) HYDROGEN SULFIDE PRECURSORS AND CONJUGATES THEREOF

(71) Applicant: Georgia State University Research Foundation, Inc., Atlanta, GA (US)

(72) Inventors: Binghe Wang, Marietta, GA (US); Yueqin Zheng, Atlanta, GA (US); Kaili Ji, Brookhaven, GA (US); Bingchen Yu, Atlanta, GA (US); Zhixiang Pan, Brookhaven, GA (US)

(73) Assignee: Georgia State University Research Foundation, Inc., Atlanta, GA (US)

( * ) Notice: Subject to any disclaimer, the term of this patent is extended or adjusted under 35 U.S.C. 154(b) by 0 days.

(21) Appl. No.: 15/563,887

(22) PCT Filed: Apr. 4, 2016

(86) PCT No.: PCT/US2016/025919
§ 371 (c)(1),
(2) Date: Oct. 2, 2017

(87) PCT Pub. No.: WO2016/161445
PCT Pub. Date: Oct. 6, 2016

(65) Prior Publication Data
US 2018/0118674 A1   May 3, 2018

Related U.S. Application Data

(60) Provisional application No. 62/142,908, filed on Apr. 3, 2015.

(51) Int. Cl.
*C07C 327/12* (2006.01)
*C07C 381/00* (2006.01)
*C07F 9/12* (2006.01)
*C01B 17/16* (2006.01)
*A61P 15/10* (2006.01)
*A61P 27/02* (2006.01)
*A61P 37/00* (2006.01)
(Continued)

(52) U.S. Cl.
CPC .............. *C07C 327/12* (2013.01); *A61P 1/00* (2018.01); *A61P 3/08* (2018.01); *A61P 7/02* (2018.01); *A61P 9/00* (2018.01); *A61P 9/10* (2018.01); *A61P 9/12* (2018.01); *A61P 11/00* (2018.01); *A61P 11/06* (2018.01); *A61P 13/02* (2018.01); *A61P 13/08* (2018.01); *A61P 13/12* (2018.01); *A61P 15/10* (2018.01); *A61P 19/02* (2018.01); *A61P 25/00* (2018.01); *A61P 25/16* (2018.01); *A61P 25/28* (2018.01); *A61P 27/02* (2018.01); *A61P 29/00* (2018.01); *A61P 35/00* (2018.01); *A61P 37/00* (2018.01); *C01B 17/16* (2013.01); *C07C 323/62* (2013.01); *C07C 381/00* (2013.01); *C07F 9/12* (2013.01); *C12P 3/00* (2013.01); *C07C 2601/02* (2017.05); *C07C 2602/08* (2017.05)

(58) Field of Classification Search
CPC ........... A61P 11/00; A61P 11/06; A61P 13/02; A61P 13/08; A61P 13/12; A61P 15/10; A61P 19/02; A61P 1/00; A61P 25/00; A61P 25/16; A61P 25/28; A61P 27/02; A61P 29/00; A61P 35/00; A61P 37/00; A61P 3/08; A61P 7/02; A61P 9/00; A61P 9/10; A61P 9/12; C01B 17/16; C07C 2601/02; C07C 2602/08; C07C 323/62; C07C 327/12; C07C 381/00; C07F 9/12; C12P 3/00
See application file for complete search history.

(56) References Cited

U.S. PATENT DOCUMENTS 4,097,487 A   6/1978   Murakami et al.

FOREIGN PATENT DOCUMENTS

DE       190292   * 11/1905
EP    0549006 A2    6/1993
(Continued)

OTHER PUBLICATIONS

International Search Report and Written Opinion dated Jul. 8, 2016, in PCT/US2016/025919, filed Apr. 4, 2016, 14 pages.
Harrowven DC, et al. "A Simple and Direct Method for Converting Thioamides into Thioesters". Tetrahedron, Elsevier Science Publishers, Amsterdam, NL, vol. 55, No. 4, Jan. 22, 1999, pp. 1187-1196.
(Continued)

*Primary Examiner* — Umamaheswari Ramachandran
(74) *Attorney, Agent, or Firm* — Kilpatrick Townsend & Stockton LLP

(57) ABSTRACT

The present invention provides methods of forming hydrogen sulfide. The methods include contacting a precursor compound with an unmasking agent; wherein the precursor compound comprises a hydrogen sulfide releasing moiety and a masked nucleophile; and wherein the contacting is conducted under conditions sufficient for cyclization of the precursor compound via lactone or lactam formation; thereby releasing hydrogen sulfide from the precursor compound. Hydrogen sulfide precursor compounds according to Formula I are also described, as well as methods for treating diseases and conditions using hydrogen sulfide precursors.

8 Claims, 10 Drawing Sheets

(51) Int. Cl.
| | |
|---|---|
| A61P 7/02 | (2006.01) |
| A61P 13/08 | (2006.01) |
| A61P 3/08 | (2006.01) |
| A61P 9/10 | (2006.01) |
| A61P 25/28 | (2006.01) |
| A61P 9/00 | (2006.01) |
| A61P 11/06 | (2006.01) |
| A61P 19/02 | (2006.01) |
| A61P 9/12 | (2006.01) |
| A61P 13/02 | (2006.01) |
| A61P 13/12 | (2006.01) |
| A61P 1/00 | (2006.01) |
| A61P 11/00 | (2006.01) |
| A61P 25/00 | (2006.01) |
| A61P 25/16 | (2006.01) |
| A61P 29/00 | (2006.01) |
| A61P 35/00 | (2006.01) |
| C07C 323/62 | (2006.01) |
| C12P 3/00 | (2006.01) |

(56) References Cited

FOREIGN PATENT DOCUMENTS

| JP | 09202775 | * | 8/1997 |
| WO | WO 9603378 | * | 8/1996 |

OTHER PUBLICATIONS

Harrowven et al., "The Synthesis of a Natural Product Family: from debromoisooaurinterol to the Aplysins" Tetrahedron, vol. 57, 2001, pp. 791-804.
Burhardt et al., "Palladium-Catalyzed Thiocarbonylation of Aryl, Vinyl and Benzyl Bromides", J. Org. Chem. vol. 79, Dec. 19, 2014, pp. 11830-11840.
Predmore et al. "Hydrogen Sulfide in Biochemistry and Medicine" Antioxidants & Redox Signaling, vol. 17, No. 1, Jan. 2012, pp. 119-140.
Shan D. et al. "Prodrug Strategies Based on Intramolecular Cyclization Reactions" Journal of Pharmaceutical Sciences, American Pharmaceutical Association, Washington U.S., vol. 86, No. 7, Jul. 1, 1997, pp. 765-767.
Cooke et al. "A Novel an Selective Approach to Enantiomerically Pure Bicyclic-Trans-Lactams via a Titanium Enolate of a Thiopyridyl Ester", J. Org. Chem., vol. 66, Dec. 6, 2000, pp. 334-336.
Vandiver, M. S.; Snyder, S. H. *Journal of molecular medicine* (Berlin, Germany) 2012, 90, 255.
Szabo, C. *Nature reviews. Drug discovery* 2007, 6, 917.
Wang, R. *Physiological reviews* 2012, 92, 791.
Blackstone, E.; Morrison, M.; Roth, M. B. *Science* (New York, N.Y.) 2005, 308, 518.
Lowicka, E.; Beltowski, J. *Pharmacological reports*: PR 2007, 59, 4.
Calver, J. W.; Coetzee, W. A.; Lefer, D. J. *Antioxidants & redox signaling* 2010, 12, 1203.
Gadalla, M. M.; Snyder, S. H. *Journal of neurochemistry* 2010, 113, 14.
Kashfi, K.; Olson, K. R. *Biochemical pharmacology* 2013, 85, 689.
Zhao, Y.; Biggs, T. D.; Xian, M. *Chemical communications* (Cambridge, England) 2014, 50, 11788.
Song, Z. J.; Ng, M. Y.; Lee, Z.-W.; Dai, W.; Hagen, T.; Moore, P. K.; Huang, D.; Deng, L.-W.; Tan, C.-H. *MedChemComm* 2014, 5, 557.
Benavides, G. A.; Squadrito, G. L.; Mills, R. W.; Patel, H. D.; Isbell, T. S.; Patel, R. P.; Darley-Usmar, V. M.; Doeller, J. E.; Kraus, D. W. *Proceedings of the National Academy of Sciences of the United States of America* 2007, 104, 17977.
Li, L.; Whiteman, M.; Guan, Y. Y.; Neo, K. L.; Cheng, Y.; Lee, S. W.; Zhao, Y.; Baskar, R.; Tan, C. H.; Moore, P. K. *Circulation* 2008, 117, 2351.
Baskar, R.; Sparatore, A.; Del Soldato, P.; Moore, P. K. *European journal of pharmacology* 2008, 594, 1.
Qandil, A. M. *International Journal of Molecular Sciences* 2012, 13, 17244.
Zhao, Y.; Wang, H.; Xian, M. *Journal of the American Chemical Society* 2011, 133, 15.
Zhao, Y.; Bhushan, S.; Yang, C.; Otsuka, H.; Stein, J. D.; Pacheco, A.; Peng, B.; Devarie-Baez, N. O.; Aguilar, H. C.; Lefer, D. J.; Xian, M. *ACS chemical biology* 2013, 8, 1283.
Martelli, A.; Testai, L.; Citi, V.; Marino, A.; Pugliesi, I.; Barresi, E.; Nesi, G.; Rapposelli, S.; Taliani, S.; Da Settimo, F.; Breschi, M. C.; Calderone, V. *ACS medicinal chemistry letters* 2013, 4, 904.
Devarie-Baez, N. O.; Bagdon, P. E.; Peng, B.; Zhao, Y.; Park, C. M.; Xian, M. *Organic letters* 2013, 15, 2786.
Fukushima, N.; Ieda, N.; Sasakura, K.; Nagano, T.; Hanaoka, K.; Suzuki, T.; Miyata, N.; Nakagawa, H. *Chemical communications* (Cambridge, England) 2014, 50, 587.
Zhou, Z.; von Wantoch Rekowski, M.; Coletta, C.; Szabo, C.; Bucci, M.; Cirino, G.; Topouzis, S.; Papapetropoulos, A.; Giannis, A. *Bioorganic & medicinal chemistry* 2012, 20, 2675.
Kondo, K.; Bhushan, S.; King, A. L.; Prabhu, S. D.; Hamid, T.; Koenig, S.; Murohara, T.; Predmore, B. L.; Gojon, G.; Gojon, G.; Wang, R.; Karusula, N.; Nicholson, C. K.; Calvert, J. W.; Lefer, D. J. *Circulation* 2013, 127, 1116.
Amsberry, K. L.; Gerstenberger, A. E.; Borchardt, R. T. *Pharmaceutical research* 1991, 8, 455.
Rao, Y.; Li, X.; Nagorny, P.; Hayashida, J.; Danishefsky, S. J. *Tetrahedron letters* 2009, 50, 6684.
Elleby, B.; Sjoblom, B.; Lindskog, S. *European journal of biochemistry / FEBS* 1999, 262, 516.
Levine, M. N.; Raines, R. T. *Chemical Science* 2012, 3, 2412.
Shan, D.; Nicolaou, M. G.; Borchardt, R. T.; Wang, B. *Journal of Pharmaceutical Sciences* 1997, 86, 765.

* cited by examiner

HYDROGEN SULFIDE PRECURSORS AND CONJUGATES THEREOF

CROSS-REFERENCES TO RELATED APPLICATIONS

The present application is a 35 U.S.C. 371 national stage application of International Pat. Appl. No. PCT/US2016/025919, which claims priority to U.S. Provisional Pat. Appl. No. 62/142,908, filed Apr. 3, 2015, which applications are incorporated herein by reference in their entirety.

STATEMENT AS TO RIGHTS TO INVENTIONS MADE UNDER FEDERALLY SPONSORED RESEARCH AND DEVELOPMENT

The invention set forth in the present application was made with government support under Grant Nos. CA180805 and CA180519, awarded by the National Institutes of Health. The United States government has certain rights in the invention.

BACKGROUND OF THE INVENTION

Hydrogen sulfide ($H_2S$) is a well-known colorless, toxic and lethal gas with the smell of rotten eggs. It is water soluble as well as lipophilic and can therefore be transported rapidly between cells and tissues. Together with nitric oxide (NO) and carbon monoxide (CO), $H_2S$ belongs to the gasotransmitter family and plays an important role in mammalian systems as a signaling molecule. Therefore, $H_2S$ has promising medical and pharmaceutical applications.

As an endogenous gasotransmitter, hydrogen sulfide is known to reduce inflammatory processes such as edema, cytokine synthesis, and leukocyte adherence to the endothelium. It has been reported that hydrogen sulfide reduces the risk of gastric injury due to ulceration and accelerates repair. Therefore, $H_2S$ releasing agents coupled with non-steroidal anti-inflammatory drugs present prospects for improved gastrointestinal safety, parent-drug potency and overall drug efficacy along with reduced the adverse effects associated with NSAIDs.

Several studies have reported various $H_2S$ donors, which include, garlic and related sulfur compounds; Lawesson's reagent and analogs (e.g., GYY4137); 1,2-dithiole-3-thiones (DTTs) and hybrids of $H_2S$ and non-steroidal anti-inflammatory drugs; thiol-activated $H_2S$ donors; photo-induced $H_2S$ donors; and thiolamino acids. There are several limitations reported for these $H_2S$ donors. Most suffer from drawbacks such as uncontrollable or fixed and inflexible release rates. Others, having controllable $H_2S$ donors, such as thiol-activated $H_2S$ donors, consume free thiols in biological systems, which can cause changes in thiol redox balance. $H_2S$ donors that can afford a slow and continuous release of $H_2S$ mimicking the endogenous $H_2S$ production through enzymatically controlled processes are currently not available.

Therefore, there is a need for new $H_2S$ donors, which generate $H_2S$ in vivo and in vitro controllably without the need for harmful external stimuli (e.g., UV light) or consumption of biological nutrients which could affect the homeostasis of other important biological species. The present invention provides new $H_2S$ donors that meet this need, providing significant advantages for medical, pharmaceutical and research applications.

BRIEF SUMMARY OF THE INVENTION

In one aspect, the present invention provides a method of forming hydrogen sulfide. The method includes contacting a precursor compound with an unmasking agent; wherein the precursor compound contains a hydrogen sulfide releasing moiety and a masked nucleophile; and wherein the contacting is conducted under conditions sufficient for cyclization of the precursor compound via lactone or lactam formation; thereby releasing hydrogen sulfide from the precursor compound.

In another aspect, the invention provides compounds according to Formula I as described herein:

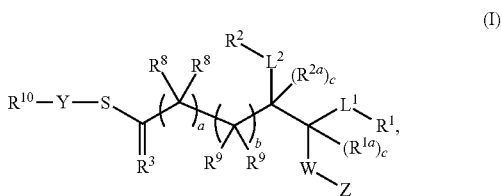

(I)

or a pharmaceutically acceptable salt thereof, wherein:
$R^1$ and $R^2$ are taken together to form $C_6$-$C_{10}$ aryl, $C_3$-$C_6$ cycloalkyl, 3- to 10-membered heterocyclyl, or 5- to 10-membered heteroaryl, each of which is optionally substituted with 1-3 $R^4$;
each $R^{1a}$ and $R^{2a}$, when present, is independently selected from H and $C_{1-6}$ alkyl;
each $R^4$ is independently selected from $C_1$-$C_6$ alkyl, $C_1$-$C_6$ alkoxy, $C_1$-$C_6$ haloalkyl, $C_1$-$C_6$ haloalkoxy, $C_1$-$C_6$ aminoalkyl, $C_1$-$C_6$ aminoalkoxy, $C_1$-$C_6$ thioalkyl, $C_1$-$C_6$ thioalkoxy, $C_3$-$C_6$ cycloalkyl, $C_6$-$C_{10}$ aryl, 6-10 membered heterocyclyl, —C(=O)$R^5$, —C(=O)O$R^5$, —$NR^5$C(=O)O$R^5$, —C(=O)$NR^5$, halo, —CN, —$NO_2$, —$N_3$, and —$NHR^5$;
$L^1$ and $L^2$ are independently selected from a bond, —(CH_2)_x—, —$SO_2$—, —CO—, —$NR^5$—, —$NR^5$CO—, and —$NR^5SO_2$—, wherein each subscript x is independently 0, 1, 2, 3, or 4;
$R^3$ is selected from O, S, and NH;
W is selected from O, S, and NH;
Z is selected from —C(=O)$R^6$, —$R^6$, —C(=O)O$R^6$, —(CH_2)_xO$R^6$, —(CH_2)_xC(=O)O$R^6$, —(CH_2)_xOC(=O)$R^6$, —(CH_2)_xOP(=O)(O$R^6$)_x, —OP(=O)(O$R^6$)_x, —P(=O)(O$R^6$)_x, and $R^7$, wherein each subscript x is independently 0, 1, 2, 3, or 4;
each $R^8$ is independently selected from H, $C_1$-$C_6$ alkyl, $C_1$-$C_6$ alkoxy, $C_1$-$C_6$ haloalkyl, $C_1$-$C_6$ haloalkoxy, $C_1$-$C_6$ aminoalkyl, $C_1$-$C_6$ aminoalkoxy, $C_1$-$C_6$ thioalkyl, $C_1$-$C_6$ thioalkoxy, $C_3$-$C_6$ cycloalkyl, $C_6$-$C_{10}$ aryl, —C(=O)$R^5$, —C(=O)O$R^5$, —C(=O)$NR^5$, halo, CN, $NO_2$, $N_3$, and —$NHR^5$,
each $R^9$ is independently selected from $C_1$-$C_6$ alkyl, H, $C_1$-$C_6$ alkoxy, $C_1$-$C_6$ haloalkyl, $C_1$-$C_6$ haloalkoxy, $C_1$-$C_6$ aminoalkyl, $C_1$-$C_6$ aminoalkoxy, $C_1$-$C_6$ thioalkyl, $C_1$-$C_6$ thioalkoxy, $C_3$-$C_6$ cycloalkyl, $C_6$-$C_{10}$ aryl, —C(=O)$R^5$, —C(=O)O$R^5$, —C(=O)$NR^5$, halo, CN, $NO_2$, $N_3$, and —$NHR^5$,
wherein one $R^8$ is optionally taken together with one $R^9$ to form a double bond;
Y is selected from a bond, —S—, —C(O)S—, and —NH—;
$R^{10}$ is selected from H, $C_1$-$C_6$ alkyl, $C_6$-$C_{10}$ aryl, ($C_6$-$C_{10}$ aryl)-($C_1$-$C_6$ alkyl), $C_3$-$C_6$ cycloalkyl and 5- to 10-membered heteroaryl, wherein $C_1$-$C_6$ alkyl, $C_6$-$C_{10}$ aryl, ($C_6$-$C_{10}$ aryl)-($C_1$-$C_6$ alkyl), $C_3$-$C_6$ cycloalkyl, and 5- to 10-membered heteroaryl are optionally substituted with 1-5 $R^{10a}$;

each $R^{10a}$ is independently selected from $C_1$-$C_6$ alkyl, —C(=O)OR$^5$, —NR$^5$C(=O)OR$^5$, and a moiety —W—Z;

each $R^5$ is independently selected from H and $C_1$-$C_4$ alkyl;

each $R^6$ is independently selected from H, $C_1$-$C_4$ alkyl, $C_2$-$C_4$ alkenyl, $C_2$-$C_4$ alkynyl, and $C_3$-$C_4$ cycloalkyl;

$R^7$ is a sugar or a drug moiety;

subscripts a and b are independently 0, 1, 2, or 3;

each subscript c is 0 when $R^1$ and $R^2$ form aryl or heteroaryl; and each subscript c is 1 when $R^1$ and $R^2$ form cycloalkyl or heterocyclyl.

In some embodiments, the compounds of Formula I have a structure according to Formula Ia:

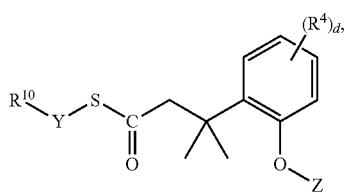

(Ia)

wherein:

Y is selected from a bond and —S—; and subscript d is 0, 1, or 2.

In another aspect, the invention provides a method of providing hydrogen sulfide to a subject in need thereof. The method includes administering a compound according to formula I or its pharmaceutical composition, to a subject in need thereof under conditions sufficient to form hydrogen sulfide.

DETAILED DESCRIPTION OF THE INVENTION

I. General

Figure 1:
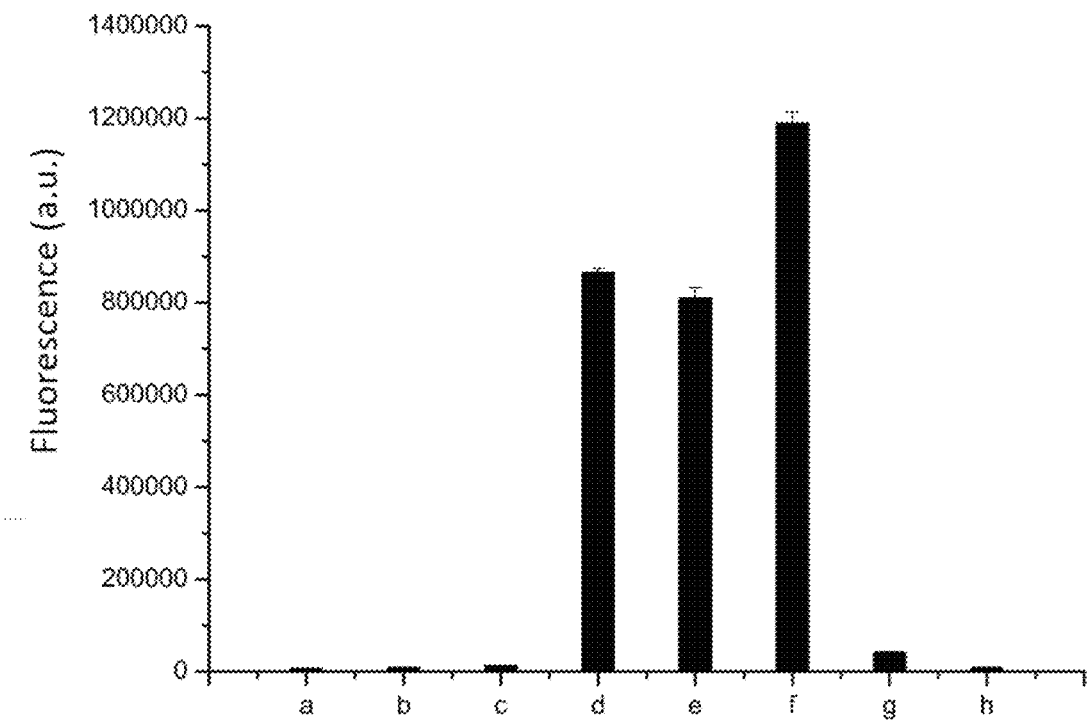
FIG. 1 shows esterase-induced release of $H_2S$ from $H_2S$ precursor HP-101, in PBS buffer and cell media, detected using WSP-5.

The present invention provides method of forming hydrogen sulfide using precursor compounds, which upon contact with unmasking agents release hydrogen sulfide through cyclization of the precursor compound via lactone or lactam formation. Such compounds find applications in the treatment of hydrogen sulfide deficient states such as cardiovascular conditions, ophthalmic conditions, neurological conditions, diabetes, inflammation, hypertension, asthma, gastric injury, irritable bowel syndrome, kidney dysfunction, sepsis, ischemia, respiratory distress syndrome, thrombosis and cancer. Due to the ability of $H_2S$ to mediate gastric mucosal defense, the $H_2S$ precursors of the invention can be especially useful for coupling with NSAIDs, as the latter are associated with gastrointestinal (GI) toxicity, particularly in upper GI tract.

II. Definitions

As used herein, the term "contacting" refers to the process of bringing into contact at least two distinct species such that they can react. It should be appreciated, however, that the resulting reaction product can be produced directly from a reaction between the added reagents or from an intermediate from one or more of the added reagents which can be produced in the reaction mixture.

As used herein, the term "hydrogen sulfide" refers to hydrogen sulfide ($H_2S$) as well as other forms of hydrogen sulfide formed under physiological conditions, including, but not limited to, $HS^-$ and $S^{2-}$.

As used herein, the term "precursor compound" refers to a compound that, following administration, releases hydrogen sulfide in vivo via a chemical reaction (e.g., a precursor on reaching physiological pH or through enzyme action is converted to the biologically active compound). A precursor itself may either lack or possess the desired biological activity.

As used herein, the term "cyclization" refers to formation of one or more rings in a chemical compound.

As used herein, the term "unmasking agent" refers to an agent that promotes the physiological release and increase in plasma levels of endogenous hydrogen sulfide by effecting the cleavage or release of a masking group. Chemical unmasking agents can include, but are not limited to, hydrolyzing agents, oxidizing agents, and reducing agents. Biological unmasking agents can include, but are not limited to, proteins (including enzymes) and nucleic acids. In some embodiments, the biological unmasking agent is an enzyme. In some embodiments, the biological unmasking agent is a hydrolase. In some embodiments, the biological unmasking agent is an esterase.

As used herein, the term "lactone" refers to a cyclic ester.

As used herein, the term "lactam" refers to a cyclic amide.

As used herein, the term "enzyme" refers to a protein that catalyzes a chemical reaction. Enzymes can be endogenous or exogenous proteins. Enzymes include, but are not limited to, hydrolases, esterases, phosphatases, glycosidases, oxidases, reductases, lipases, transferases, polymerases and ligases. In some embodiments, the enzyme is a hydrolase. In some embodiments, the enzyme is an esterase. In some embodiments, the enzyme is a glycosidase. In some embodiments, the enzyme is a phosphatase.

As used herein, the term "cell targeting moiety" refers to any moiety that targets a particular cell type. Cell-targeting moieties can target a cell by interacting with, or binding to, cell-surface receptors or other molecules on the cell surface. Cell targeting moieties can also target cells by interacting with proteins secreted by the cell. The cell-targeting moiety can be an antibody, a molecule that binds to receptors or proteins on the cell-surface, a peptide or a peptidomimetic compound. In certain embodiments, the cell-targeting moiety (e.g., ligand, antibody, or other molecule) specifically binds to a cell receptor of the targeted cell type. The term "specifically bind" means that the cell-targeting moiety binds to a particular type of cell receptor with preference, or with higher affinity, than to another type of cell receptor.

As used herein, the term "peptidomimetic" refers to a compound containing non-peptidic structural elements that is capable of mimicking or antagonizing the biological action(s) of a natural parent peptide.

As used herein, the term "antibody" refers to an immunoglobulin molecule immunologically reactive with a particular antigen, and includes both polyclonal and monoclonal antibodies. The term also includes genetically engineered forms such as chimeric antibodies (e.g., humanized murine antibodies) and heteroconjugate antibodies (e.g., bispecific antibodies). The term "antibody" also includes antigen binding forms of antibodies, including fragments with antigen-binding capability (e.g., Fab', F(ab')$_2$, Fab, Fv and rIgG. See also, Pierce Catalog and Handbook, 1994-1995 (Pierce Chemical Co., Rockford, Ill.). See also, e.g., Kuby, J., *Immunology*, 3$^{rd}$ Ed., W.H. Freeman & Co., New York (1998). The term also refers to recombinant single chain Fv fragments (scFv). The term antibody also includes bivalent or bispecific molecules, diabodies, triabodies, and tetrabodies. Bivalent and bispecific molecules are described in, e.g., Kostelny et al., (1992) *J Immunol* 148:1547, Pack and Pluckthun (1992) *Biochemistry* 31:1579, Hollinger et al., 1993, supra, Gruber et al. (1994) *J Immunol:* 5368, Zhu et al. (1997) *Protein Sci* 6:781, Hu et al. (1996) *Cancer Res.* 56:3055, Adams et al. (1993) *Cancer Res.* 53:4026, and McCartney, et al. (1995) *Protein Eng.* 8:301.

As used herein, the term "drug moiety" refers to a pharmaceutical drug or a functional group that can be converted to a pharmaceutical drug upon cleavage from hydrogen sulfide precursor compound as described above. The conversion to the pharmaceutical drug can occur concomitantly with the release from the precursor compound, or the conversion can occur in one or more steps following the release.

As used herein, the term "non-steroidal anti-inflammatory drug" refers to drugs that are not steroids and used to treat inflammatory disorders. NSAIDs include, but are not limited to, the group consisting of ibuprofen, naproxen, sulindac, aceclofenac, salicylates, indomethacin, flurbiprofen, diclofenac, ketorolac, piroxicam, tebufelone, etodolac, nabumetone, aminopyrine, phenylbutazone, oxyphenbutazone, fenoprofen, flufenamic acid, ketoprofen, mefenamic acid, and phenacetin, including isomers, enantiomers, tautomers and alkaline salts thereof.

As used herein, the term "alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be unsubstituted or substituted with 1-6 $R^S$ groups as described below.

As used herein, the term "alkoxy" refers to an alkyl group having an oxygen atom that connects the alkyl group to the point of attachment: alkyl-O—. As for alkyl groups, alkoxy groups can have any suitable number of carbon atoms, such as $C_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. Alkoxy groups can be unsubstituted or substituted with 1-6 $R^S$ groups as described below.

As used herein, the term "halogen" refers to fluorine, chlorine, bromine and iodine.

As used herein, the term "haloalkyl" refers to alkyl, as defined above, where some or all of the hydrogen atoms are replaced with halogen atoms. As for alkyl groups, haloalkyl groups can have any suitable number of carbon atoms, such as $C_{1-6}$. For example, haloalkyl includes trifluoromethyl, fluoromethyl, etc. In some instances, the term "perfluoro" can be used to define a compound or radical where all the hydrogens are replaced with fluorine. For example, perfluoromethyl refers to 1,1,1-trifluoromethyl.

As used herein, the term "haloalkoxy" refers to an alkoxy group where some or all of the hydrogen atoms are substituted with halogen atoms. As for alkyl groups, haloalkoxy groups can have any suitable number of carbon atoms, such as $C_{1-6}$. The alkoxy groups can be substituted with 1, 2, 3, or more halogens. When all the hydrogens are replaced with a halogen, for example by fluorine, the compounds are per-substituted, for example, perfluorinated. Haloalkoxy includes, but is not limited to, trifluoromethoxy, 2,2,2,-trifluoroethoxy, perfluoroethoxy, etc.

As used herein, the term "heteroalkyl" refers to an alkyl group of any suitable length and having from 1 to 3 heteroatoms such as N, O and S. Additional heteroatoms can also be useful, including, but not limited to, B, Al, Si and P. The heteroatoms can also be oxidized; oxidized heteroatoms include, but are not limited to, —S(O)— and —S(O)$_2$—. Examples of heteroalkyl groups include ethers, thioethers and alkyl-amines. The heteroatom portion of the heteroalkyl can replace a hydrogen of the alkyl group to form a hydroxy, thio or amino group. Alternatively, the heteroatom portion can be the connecting atom, or be inserted between two carbon atoms.

As used herein, the term "amino" refers to an —N(R)$_2$ group where the R groups can be hydrogen, alkyl, alkenyl, alkynyl, cycloalkyl, heterocycloalkyl, aryl, or heteroaryl.

The R groups can be the same or different. The amino groups can be primary (each R is hydrogen), secondary (one R is hydrogen) or tertiary (each R is other than hydrogen).

As used herein, the term "aminoalkyl" refers to an alkyl group as defined herein, having one or more amino groups. The amino groups can be primary, secondary or tertiary. The amino alkyl group can be further substituted with a hydroxy group to form an amino-hydroxy group. Amino alkyl groups useful in the present invention include, but are not limited to, aminoethyl, aminopropyl and aminoisopropyl. The amino group can link the alkyl amine to the point of attachment with the rest of the compound, be at the terminal position of the alkyl group, or link together at least two carbon atoms of the alkyl group. One of skill in the art will appreciate that other alkyl amines are useful in the present invention.

As used herein, the term "thiol" refers to an —SH group.

As used herein, the term "sugar" refers to a monosaccharide, a disaccharide, an oligosaccharide or a polysaccharide. Monosaccharides include, but are not limited to, glucose, ribose and fructose. Disaccharides include, but are not limited to, sucrose and lactose. Polysaccharides include, but are not limited to, cellulose, hemicellulose and lignocellulose or starch. Other sugars are useful in the present invention.

As used herein, the term "cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to cyclopropyl, cyclobutyl, cyclopentyl, and cyclohexyl. Cycloalkyl groups can be unsubstituted or substituted with 1-6 $R^S$ groups as described below.

As used herein, the term "heterocyclyl" refers to a saturated ring system having from 3 to 12 ring members and from 1 to 6 heteroatoms selected from N, O and S. Additional heteroatoms can also be useful, including, but not limited to, B, Al, Si and P. The heteroatoms can also be oxidized; oxidized heteroatoms include, but are not limited to, —S(O)— and —S(O)$_2$—. Heterocyclyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocyclyl groups, such as 1, 2, 3, or 4, or 1 to 2, 1 to 3, 1 to 4, 2 to 3, 2 to 4, or 3 to 4. The heterocyclyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocyclyl groups can also be fused to aromatic or non-aromatic ring systems to form members including, but not limited to, indoline. Heterocyclyl groups can be unsubstituted or substituted with 1-6 $R^S$ groups as described below.

The heterocyclyl groups can be linked via any position on the ring. For example, aziridine can be 1- or 2-aziridine, azetidine can be 1- or 2-azetidine, pyrrolidine can be 1-, 2- or 3-pyrrolidine, piperidine can be 1-, 2-, 3- or 4-piperidine, pyrazolidine can be 1-, 2-, 3-, or 4-pyrazolidine, imidazolidine can be 1-, 2-, 3- or 4-imidazolidine, piperazine can be 1-, 2-, 3- or 4-piperazine, tetrahydrofuran can be 1- or 2-tetrahydrofuran, oxazolidine can be 2-, 3-, 4- or 5-oxazolidine, isoxazolidine can be 2-, 3-, 4- or 5-isoxazolidine, thiazolidine can be 2-, 3-, 4- or 5-thiazolidine, isothiazolidine can be 2-, 3-, 4- or 5-isothiazolidine, and morpholine can be 2-, 3- or 4-morpholine.

When heterocyclyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxzoalidine, thiazolidine, isothiazolidine, morpholine, thiomorpholine, dioxane and dithiane. Heterocycloalkyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

As used herein, the term "aryl" refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be unsubstituted or substituted with 1-6 $R^S$ groups as described below.

As used herein, the term "heteroaryl" refers to a monocyclic or fused bicyclic or tricyclic aromatic ring assembly containing 5 to 16 ring atoms, where from 1 to 5 of the ring atoms are a heteroatom such as N, O or S. Additional heteroatoms can also be useful, including, but not limited to, B, Al, Si and P. The heteroatoms can also be oxidized; oxidized heteroatoms include, but are not limited to, —S(O)— and —S(O)$_2$—. Heteroaryl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be unsubstituted or substituted with 1-6 $R^S$ groups as described below.

The heteroaryl groups can be linked via any position on the ring. For example, pyrrole includes 1-, 2- and 3-pyrrole, pyridine includes 2-, 3- and 4-pyridine, imidazole includes 1-, 2-, 4- and 5-imidazole, pyrazole includes 1-, 3-, 4- and 5-pyrazole, triazole includes 1-, 4- and 5-triazole, tetrazole includes 1- and 5-tetrazole, pyrimidine includes 2-, 4-, 5- and 6-pyrimidine, pyridazine includes 3- and 4-pyridazine, 1,2,3-triazine includes 4- and 5-triazine, 1,2,4-triazine includes 3-, 5- and 6-triazine, 1,3,5-triazine includes 2-triazine, thiophene includes 2- and 3-thiophene, furan includes 2- and 3-furan, thiazole includes 2-, 4- and 5-thiazole, isothiazole includes 3-, 4- and 5-isothiazole, oxazole includes 2-, 4- and 5-oxazole, isoxazole includes 3-, 4- and 5-isoxazole, indole includes 1-, 2- and 3-indole, isoindole includes 1- and 2-isoindole, quinoline includes 2-, 3- and 4-quinoline, isoquinoline includes 1-, 3- and 4-isoquinoline, quinazoline includes 2- and 4-quinoazoline, cinnoline includes 3- and 4-cinnoline, benzothiophene includes 2- and 3-benzothiophene, and benzofuran includes 2- and 3-benzofuran.

Some heteroaryl groups include those having from 5 to 10 ring members and from 1 to 3 ring atoms including N, O or S, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, isoxazole, indole, isoindole, quinoline, isoquinoline, quinoxaline, quinazoline, phthalazine, cinnoline, benzothiophene, and benzofuran. Other heteroaryl groups include those having from 5 to 8 ring members and from 1 to 3 heteroatoms, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, and isoxazole. Some other heteroaryl groups include those having from 9 to 12 ring members and from 1 to 3 heteroatoms, such as indole, isoindole, quinoline, isoquinoline, quinoxaline, quinazoline, phthalazine, cinnoline, benzothiophene, benzofuran and bipyridine. Still other heteroaryl groups include those having from 5 to 6 ring members and from 1 to 2 ring atoms including N, O or S, such as pyrrole, pyridine, imidazole, pyrazole, pyrazine, pyrimidine, pyridazine, thiophene, furan, thiazole, isothiazole, oxazole, and isoxazole.

Some heteroaryl groups include from 5 to 10 ring members and only nitrogen heteroatoms, such as pyrrole, pyridine, imidazole, pyrazole, triazole, pyrazine, pyrimidine, pyridazine, triazine (1,2,3-, 1,2,4- and 1,3,5-isomers), indole, isoindole, quinoline, isoquinoline, quinoxaline, quinazoline, phthalazine, and cinnoline. Other heteroaryl groups include from 5 to 10 ring members and only oxygen heteroatoms, such as furan and benzofuran. Some other heteroaryl groups include from 5 to 10 ring members and only sulfur heteroatoms, such as thiophene and benzothiophene. Still other heteroaryl groups include from 5 to 10 ring members and at least two heteroatoms, such as imidazole, pyrazole, triazole, pyrazine, pyrimidine, pyridazine, triazine (1,2,3-, 1,2,4- and 1,3,5-isomers), thiazole, isothiazole, oxazole, isoxazole, quinoxaline, quinazoline, phthalazine, and cinnoline.

The groups defined above can optionally be substituted by any suitable number and type of substituents. In some embodiments, the groups described above are substituted with from 1-6 $R^S$ groups, wherein $R^S$ is selected from cyano, halogen, haloalkyl, haloalkoxy, —OR', =O, —OC(O)R', —(O)R', —O$_2$R', —ONR'R", —OC(O)NR'R", =NR', =N—OR', —NR'R", —NR"C(O)R', —NR'—(O)NR"R'", —NR"C(O)OR', —NH—(NH$_2$)=NH, —NR' C(NH$_2$)=NH, —NH—(NH$_2$)=NR', —SR', —S(O)R', —S(O)$_2$R', —S(O)$_2$NR'R", —NR'S(O)$_2$R", —N$_3$ and —NO$_2$. R', R" and R'" each independently refer to hydrogen and unsubstituted alkyl, such as unsubstituted $C_{1-6}$ alkyl. Alternatively, R' and R", or R" and R'", when attached to the same nitrogen, are combined with the nitrogen to which they are attached to form a heterocycloalkyl or heteroaryl ring, as defined above.

As used herein, the term "salt" refers to acid or base salts of the compounds of the invention. Illustrative examples of pharmaceutically acceptable salts include mineral acid salts (salts of hydrochloric acid, hydrobromic acid, phosphoric acid, and the like), organic acid salts (salts of acetic acid, propionic acid, glutamic acid, citric acid and the like) salts, and quaternary ammonium salts (salts of methyl iodide, ethyl iodide, and the like). It is understood that the pharmaceutically acceptable salts are non-toxic. Additional information on suitable pharmaceutically acceptable salts can be found in *Remington: The Science & Practice of Pharmacy*, 20th ed., Lippincott Williams & Wilkins, Philadelphia, Pa., 2000, which is incorporated herein by reference.

Pharmaceutically acceptable salts of the acidic compounds of the present invention are salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

Similarly acid addition salts, such as of mineral acids, organic carboxylic and organic sulfonic acids, e.g., hydrochloric acid, methanesulfonic acid, maleic acid, are also possible provided a basic group, such as pyridyl, constitutes part of the structure.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

As used herein, the term "composition" is intended to encompass a product comprising the specified ingredients in the specified amounts, as well as any product, which results, directly or indirectly, from combination of the specified ingredients in the specified amounts. By "pharmaceutically acceptable" it is meant that the carrier, diluent or excipient must be compatible with the other ingredients of the formulation and not deleterious to the recipient thereof.

As used herein, the term "pharmaceutically acceptable excipient" refers to a substance that aids the administration of an active agent to and absorption by a subject. Pharmaceutical excipients useful in the present invention include, but are not limited to, binders, fillers, disintegrants, lubricants, coatings, sweeteners, flavors and colors. One of skill in the art will recognize that other pharmaceutical excipients are useful in the present invention.

As used herein, the term "administering" refers to oral, topical, parenteral, intravenous, intraperitoneal, intramuscular, intralesional, intranasal, subcutaneous, or intrathecal administration, as well as administration via suppository or via the implantation of a slow-release device e.g., a mini-osmotic pump, to a subject.

As used herein, the term "forming a reaction mixture" refers to the process of bringing into contact at least two distinct species such that they mix together and can react, either modifying one of the initial reactants or forming a third, distinct, species, a product. It should be appreciated, however, the resulting reaction product can be produced directly from a reaction between the added reagents or from an intermediate from one or more of the added reagents which can be produced in the reaction mixture.

As used herein, the term "subject" refers to animals such as mammals, including, but not limited to, primates (e.g., humans), cows, sheep, goats, horses, dogs, cats, rabbits, rats, mice and the like. In certain embodiments, the subject is a human.

As used herein, the terms "treat", "treating" and "treatment" refer to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom. The treatment or amelioration of symptoms can be based on any objective or subjective parameter, including, e.g., the result of a physical examination.

Compounds of the present invention includes all tautomers and stereoisomers thereof, either in admixture or in pure or substantially pure form. The compounds of the present invention can have asymmetric centers at the carbon atoms, and therefore the compounds of the present invention can exist in diastereomeric or enantiomeric forms or mixtures thereof. All conformational isomers (e.g., cis and trans isomers) and all optical isomers (e.g., enantiomers and diastereomers), racemic, diastereomeric and other mixtures of such isomers, as well as solvates, hydrates, isomorphs, polymorphs and tautomers are within the scope of the present invention. Compounds according to the present invention can be prepared using diastereomers, enantiomers or racemic mixtures as starting materials. Furthermore, diastereomer and enantiomer products can be separated by chromatography, fractional crystallization or other methods known to those of skill in the art.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

The present invention also includes isotopically-labeled compounds of the present invention, wherein one or more atoms are replaced by one or more atoms having specific atomic mass or mass numbers. Examples of isotopes that can be incorporated into compounds of the invention include, but are not limited to, isotopes of hydrogen, carbon, nitrogen, oxygen, fluorine, sulfur, and chlorine (such as $^2$H, $^3$H, $^{13}$C, $^{14}$C, $^{15}$N, $^{18}$O, $^{17}$O, $^{18}$F, $^{35}$S and $^{36}$Cl).

III. Methods of Forming Hydrogen Sulfide

The present invention provides H$_2$S releasing precursor compounds which release hydrogen sulfide and other active agents via the lactonization/lactamization chemistry described herein.

In one aspect, the invention provides a method of forming hydrogen sulfide. The method includes contacting a precursor compound with an unmasking agent; wherein the precursor compound contains a hydrogen sulfide releasing moiety and a masked nucleophile; and wherein the contacting is conducted under conditions sufficient for cyclization of the precursor compound via lactone or lactam formation; thereby releasing hydrogen sulfide from the precursor compound. The hydrogen sulfide can be released under in vitro conditions or under in vivo conditions.

In some embodiments, the invention provides hydrogen sulfide precursors which function by a mechanism shown in Scheme 1.

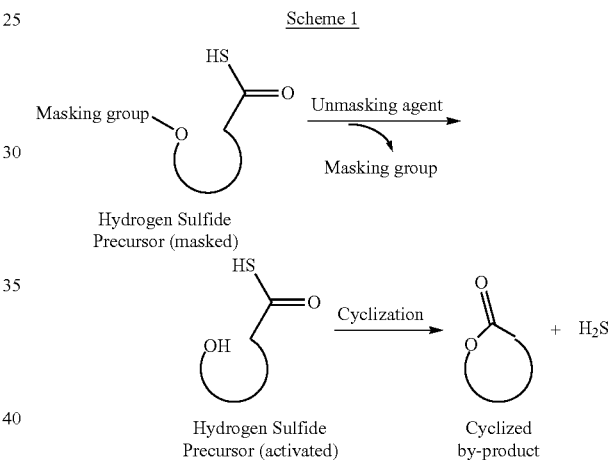

In some embodiments, the invention provides hydrogen sulfide and drug hybrid precursors which function by a mechanism shown in Scheme 2.

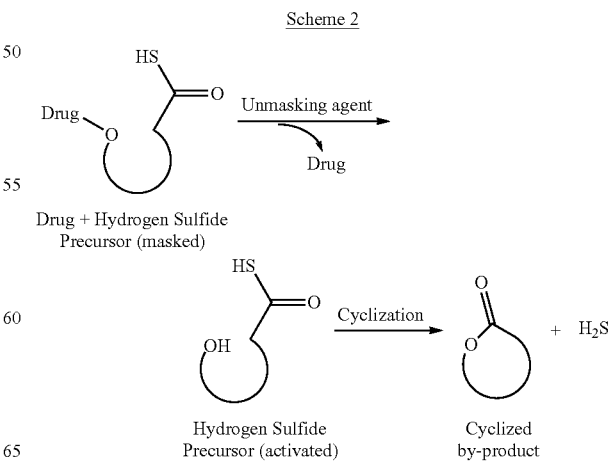

In some embodiments, the hydrogen sulfide releasing moiety is selected from a thioic S-acid, a dithioic acid, an imidothioic acid, and derivatives thereof.

In some embodiments, the hydrogen sulfide releasing moiety is a thioic S-acid or a derivative thereof, including, but not limiting to:

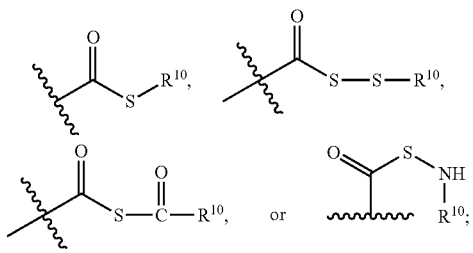

wherein $R^{10}$ is independently selected from H, alkyl, aryl, cycloalkyl and heteroaryl.

In some embodiments, the hydrogen sulfide releasing moiety is an imidothioic acid or a derivative thereof, including, but not limiting to:

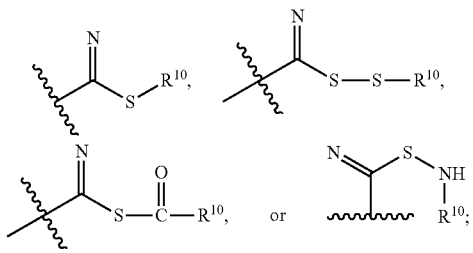

wherein $R^{10}$ is independently selected from H, alkyl, aryl, cycloalkyl and heteroaryl.

In some embodiments, the hydrogen sulfide releasing moiety is a dithioic acid or a derivative thereof, including, but not limiting to:

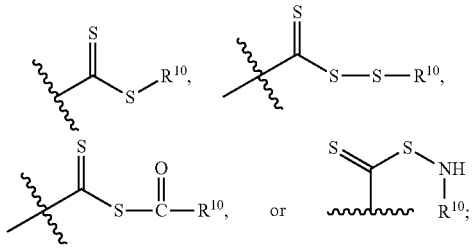

wherein $R^{10}$ is independently selected from H, alkyl, aryl, cycloalkyl and heteroaryl.

In certain embodiments, contacting the precursor compound and the umasking agent is conducted under conditions sufficient to convert the masked nucleophile to an unmasked nucleophile.

In some embodiments, the unmasking agent is an enzyme. In some embodiments, the enzyme is selected from hydrolase, phosphatase, esterase, glycosidase, oxidase and reductase. In some embodiments, the enzyme is an esterase.

In general, the esterases in the methods of the invention catalyze the hydrolysis of ester bonds. Phosphatases catalyze the hydrolysis of phosphate bonds in the methods of the invention. Glycosidases catalyze the hydrolysis of glycosidic bonds in the methods of the invention. Proteases catalyze the hydrolysis of peptide bonds (i.e., amides) in the methods of the invention. In some embodiments, the hydrolysis promotes lactone or lactam formation via cyclization of an unmasked organic acid or organic alcohol resulting from the hydrolysis.

In some embodiments, the precursor compound is conjugated to a cell targeting moiety.

In some embodiments, the cell targeting moiety is selected from a mitochondrion, a nucleus, a cell surface, a cell surface receptor, a lysosome, a liposome, a protein, and a nucleic acid. In some embodiments, the cell targeting moiety includes a triphenylphosphonium (TPP) moiety. In some embodiments, the cell targeting moiety includes a sugar. In some embodiments, the cell targeting moiety includes an antibody.

Targeting moieties used in the compounds and methods of the invention can associate with any target of interest, such as a target associated with an organ, a tissue, a cell, the extracellular matrix, or intracellular regions. In certain embodiments, a target can be associated with a particular disease state, such as an inflammation. In certain embodiments, a target can be associated with a particular disease state, such as a cancerous condition. In some embodiments, the targeting moiety can be specific to only one target, such as a receptor. Suitable targets include, but are not limited, to a nucleic acid, such as a DNA, RNA, or modified derivatives thereof. Suitable targets include, but are not limited, to proteins (such as extracellular proteins, transmembrane proteins, and enzymes), receptors (including cell surface receptors), tumor-markers, and antibodies. Suitable targets also include carbohydrates, such as a monosaccharides, disaccharides, and polysaccharides, that can be, for example, present on the surface of a cell.

In certain embodiments, a targeting moiety can include a target ligand (e.g., an RGD-containing peptide), a small molecule mimic of a target ligand (e.g., a peptide mimetic ligand), or an antibody or antibody fragment specific for a particular target. In some embodiments, a targeting moiety can further include folic acid derivatives, B-12 derivatives, integrin RGD peptides, NGR derivatives, somatostatin derivatives or peptides that bind to the somatostatin receptor, e.g., octreotide, octreotate, and the like. The targeting moiety of the present invention can also include an aptamer. Aptamers can be designed to associate with or bind to a target of interest. Aptamers can be comprised of, for example, DNA, RNA, and/or peptides, and various aspects of aptamers are well known in the art. (See. e.g., Klussman, S., Ed., The Aptamer Handbook, Wiley-VCH (2006); Nissenbaum, E. T., *Trends in Biotech.* 26(8): 442-449 (2008)).

IV. Compounds of the Invention

In a related aspect, the invention provides hydrogen sulfide precursor compounds. In some embodiments, the invention provides compounds according to Formula I:

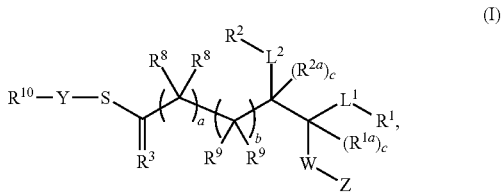

(I)

and pharmaceutically acceptable salts thereof, wherein:
$R^1$ and $R^2$ are taken together to form $C_6$-$C_{10}$ aryl, $C_3$-$C_6$ cycloalkyl, 3- to 10-membered heterocyclyl, or 5- to 10-membered heteroaryl, each of which is optionally substituted with 1-3 $R^4$;
each $R^{1a}$ and $R^{2a}$, when present, is independently selected from H and $C_{1-6}$ alkyl;
each $R^4$ is independently selected from $C_1$-$C_6$ alkyl, $C_1$-$C_6$ alkoxy, $C_1$-$C_6$ haloalkyl, $C_1$-$C_6$ haloalkoxy, $C_1$-$C_6$ aminoalkyl, $C_1$-$C_6$ aminoalkoxy, $C_1$-$C_6$ thioalkyl, $C_1$-$C_6$ thioalkoxy, $C_3$-$C_6$ cycloalkyl, $C_6$-$C_{10}$ aryl, 6-10 membered heterocyclyl, —C(=O)$R^5$, —C(=O)O$R^5$, —NR$^5$C(=O)O$R^5$, —C(=O)N$R^5$, halo, —CN, —NO$_2$, —N$_3$, and —NH$R^5$;
$L^1$ and $L^2$ are independently selected from a bond, —(CH$_2$)$_x$—, —SO$_2$—, —CO—, —N$R^5$—, —N$R^5$CO—, and —N$R^5$SO$_2$—, wherein each subscript x is independently 0, 1, 2, 3, or 4;
$R^3$ is selected from O, S, and NH;
W is selected from O, S, and NH;
Z is selected from —C(=O)$R^6$, —$R^6$, —C(=O)O$R^6$, —(CH$_2$)$_x$O$R^6$, —(CH$_2$)$_x$—C(=O)O$R^6$, —(CH$_2$)$_x$OC(=O)$R^6$, —(CH$_2$)$_x$OP(=O)(O$R^6$)$_x$, —OP(=O)(O$R^6$)$_x$, —P(=O)(O$R^6$)$_x$, and $R^7$, wherein each subscript x is independently 0, 1, 2, 3, or 4;
each $R^8$ is independently selected from H, $C_1$-$C_6$ alkyl, $C_1$-$C_6$ alkoxy, $C_1$-$C_6$ haloalkyl, $C_1$-$C_6$ haloalkoxy, $C_1$-$C_6$ aminoalkyl, $C_1$-$C_6$ aminoalkoxy, $C_1$-$C_6$ thioalkyl, $C_1$-$C_6$ thioalkoxy, $C_3$-$C_6$ cycloalkyl, $C_6$-$C_{10}$ aryl, —C(=O)$R^5$, —C(=O)O$R^5$, —C(=O)N$R^5$, halo, CN, NO$_2$, N$_3$, and —NH$R^5$,
each $R^9$ is independently selected from $C_1$-$C_6$ alkyl, H, $C_1$-$C_6$ alkoxy, $C_1$-$C_6$ haloalkyl, $C_1$-$C_6$ haloalkoxy, $C_1$-$C_6$ aminoalkyl, $C_1$-$C_6$ aminoalkoxy, $C_1$-$C_6$ thioalkyl, $C_1$-$C_6$ thioalkoxy, $C_3$-$C_6$ cycloalkyl, $C_6$-$C_{10}$ aryl, —C(=O)$R^5$, —C(=O)O$R^5$, —C(=O)N$R^5$, halo, CN, NO$_2$, N$_3$, and —NH$R^5$,
wherein one $R^8$ is optionally taken together with one $R^9$ to form a double bond;
Y is selected from a bond, —S—, —C(O)S—, and —NH—;
$R^{10}$ is selected from H, $C_1$-$C_6$ alkyl, $C_6$-$C_{10}$ aryl, ($C_6$-$C_{10}$ aryl)-($C_1$-$C_6$ alkyl), $C_3$-$C_6$ cycloalkyl and 5- to 10-membered heteroaryl, wherein $C_1$-$C_6$ alkyl, $C_6$-$C_{10}$ aryl, ($C_6$-$C_{10}$ aryl)-($C_1$-$C_6$ alkyl), $C_3$-$C_6$ cycloalkyl, and 5- to 10-membered heteroaryl are optionally substituted with 1-5 $R^{10a}$;
each $R^{10a}$ is independently selected from $C_1$-$C_6$ alkyl, —C(=O)O$R^5$, —N$R^5$C(=O)O$R^5$, and a moiety —W—Z;
each $R^5$ is independently selected from H and $C_1$-$C_4$ alkyl;
each $R^6$ is independently selected from H, $C_1$-$C_4$ alkyl, $C_2$-$C_4$ alkenyl, $C_2$-$C_4$ alkynyl, and $C_3$-$C_4$ cycloalkyl;
$R^7$ is a sugar or a drug moiety;
subscripts a and b are independently 0, 1, 2, or 3;
each subscript c is 0 when $R^1$ and $R^2$ form aryl or heteroaryl; and
each subscript c is 1 when $R^1$ and $R^2$ form cycloalkyl or heterocyclyl.
In some embodiments, $R^1$ and $R^2$ are taken together to form $C_6$-$C_{10}$ aryl, each of which is optionally substituted with 1-3 $R^4$;
each $R^4$ is independently selected from $C_1$-$C_6$ alkyl, $C_1$-$C_6$ alkoxy, $C_1$-$C_6$ haloalkyl, $C_1$-$C_6$ haloalkoxy, $C_1$-$C_6$ aminoalkyl, $C_1$-$C_6$ aminoalkoxy, $C_1$-$C_6$ thioalkyl, $C_1$-$C_6$ thioalkoxy, $C_3$-$C_6$ cycloalkyl, $C_6$-$C_{10}$ aryl, 6-10 membered heterocyclyl, —C(=O)$R^5$, —C(=O)O$R^5$, —N$R^5$C(=O)O$R^5$, —C(=O)N$R^5$, halo, —CN, —NO$_2$, —N$_3$, and —NH$R^5$;
$R^3$ is O;
W is O;
each $R^8$ is independently selected from H and $C_1$-$C_6$ alkyl;
each $R^9$ is independently selected from $C_1$-$C_6$ alkyl and H;
Y is selected from a bond and —S—;
subscripts a and b are 1; and
each subscript c is 0.
In some embodiments, $R^1$ and $R^2$ are taken together to form a phenyl group which is optionally substituted with 1-3 $R^4$. In some such embodiments, each $R^4$ is independently $C_1$-$C_6$ alkyl.
In some embodiments, each $R^9$ is $C_1$-$C_6$ alkyl. In some embodiments, each $R^8$ is H and each $R^9$ is $C_1$-$C_6$ alkyl. In some embodiments, each $R^9$ is methyl.
In some embodiments, Z is selected from —C(=O)$R^6$, —$R^6$, —C(=O)O$R^6$, —(CH$_2$)$_x$O$R^6$, —(CH$_2$)$_x$C(=O)O$R^6$, —(CH$_2$)$_x$OC(=O)$R^6$, —(CH$_2$)$_x$OP(=O)(O$R^6$)$_x$, —OP(=O)(O$R^6$)$_x$, and —P(=O)(O$R^6$)$_x$, wherein each subscript x is independently 0, 1, 2, 3, or 4. In some embodiments, Z is —C(=O)$R^6$ and $R^6$ is $C_1$-$C_4$ alkyl. In some such embodiments, Z is acetyl.
In some embodiments, Z is $R^7$ and $R^7$ is a drug moiety.
In some embodiments, the invention provides compounds according to Formula Ia:

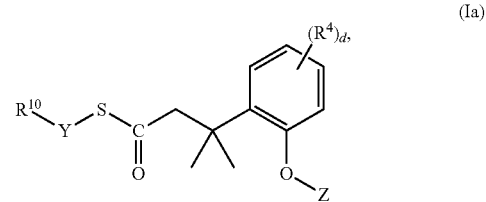

(Ia)

and pharmaceutically acceptable salts thereof, wherein:
Y is selected from a bond and —S—; and
subscript d is 0, 1, or 2.
In some embodiments, the invention provides compounds according to Formula Ia, and pharmaceutically acceptable salts thereof, wherein subscript d is 0.
In some embodiments, the invention provides compounds according to Formula Ia, and pharmaceutically acceptable salts thereof, wherein subscript d is 2 and each $R^4$ is independently $C_1$-$C_6$ alkyl. In some such embodiments, each $R^4$ is methyl.
In some embodiments, the invention provides compounds according to Formula Ia, and pharmaceutically acceptable salts thereof, wherein Z is —C(=O)$R^6$ and $R^6$ is $C_1$-$C_4$ alkyl.
In some embodiments, the invention provides compounds according to Formula Ia, and pharmaceutically acceptable salts thereof, wherein Z is $R^7$ and $R^7$ is a drug moiety.
In some embodiments, the invention provides compounds according to Formula I or Formula Ia, and pharmaceutically acceptable salts thereof, wherein Y is a bond and $R^{10}$ is H.
In some embodiments, the invention provides compounds according to Formula I or Formula Ia, and pharmaceutically acceptable salts thereof, wherein Y is —S—; and $R^{10}$ is selected from $C_1$-$C_6$ alkyl and ($C_6$-$C_{10}$ aryl)-($C_1$-$C_6$ alkyl), each of which is optionally substituted with 1-5 $R^{10a}$.

In some embodiments, the invention provides compounds according to Formula Ib:

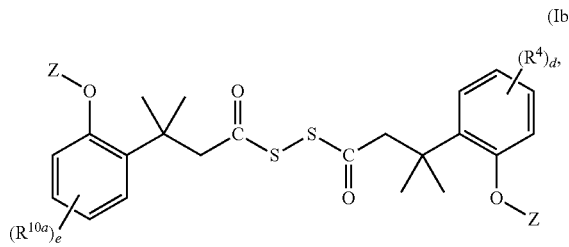
(Ib)

and pharmaceutically acceptably salts thereof, wherein subscripts d and e are independently 0, 1, or 2; and wherein each $R^{10}$ is independently selected from $C_1$-$C_6$ alkyl, —C(=O)$OR^5$, and —$NR^5$C(=O)$OR^5$.

In some embodiments, the invention provides compounds of Formula Ib wherein each Z is independently selected from —(CH$_2$)$_x$OP(=O)(OR$^6$)$_x$, —OP(=O)(OR$^6$)$_x$, —P(=O)(OR$^6$)$_x$, and R$^7$, wherein each subscript x is independently 0, 1, 2, 3, or 4. In some such embodiments, each Z is independently selected from —(CH$_2$)$_x$OP(=O)(OR$^6$)$_x$, —OP(=O)(OR$^6$)$_x$, and —P(=O)(OR$^6$)$_x$. In some embodiments, the invention provides compounds of Formula Ib wherein subscript d is 2, subscript e is 2, each $R^4$ is independently $C_1$-$C_6$ alkyl, and each $R^{10a}$ is independently $C_1$-$C_6$ alkyl. In some such embodiments, each $R^4$ is methyl and each $R^{ina}$ is methyl.

In some embodiments, the invention provides compound according to Formula II

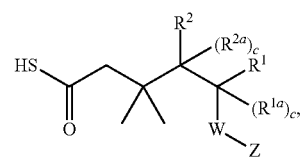
(II)

and pharmaceutically acceptable salts thereof, wherein $R^1$ and $R^2$ are taken together with the carbon atoms to which they are attached to form:

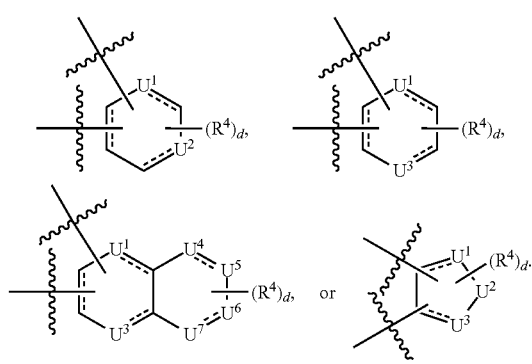

wherein the dashed lines represent the presence or absence of double bonds; $U^{1-7}$ are independently selected from C, N, O and S, provided that no more than three of $U^{1-7}$ are N, O, or S, and subscript d is 0, 1, or 2.

In some embodiments, the invention provides compounds of formula I or formula II as described above, and pharmaceutically acceptable salts thereof, wherein $L^1$ and $L^2$ are each a bond and $R^1$ and $R^2$ are taken together with the carbon atoms to which they are attached to form an aryl ring selected from:

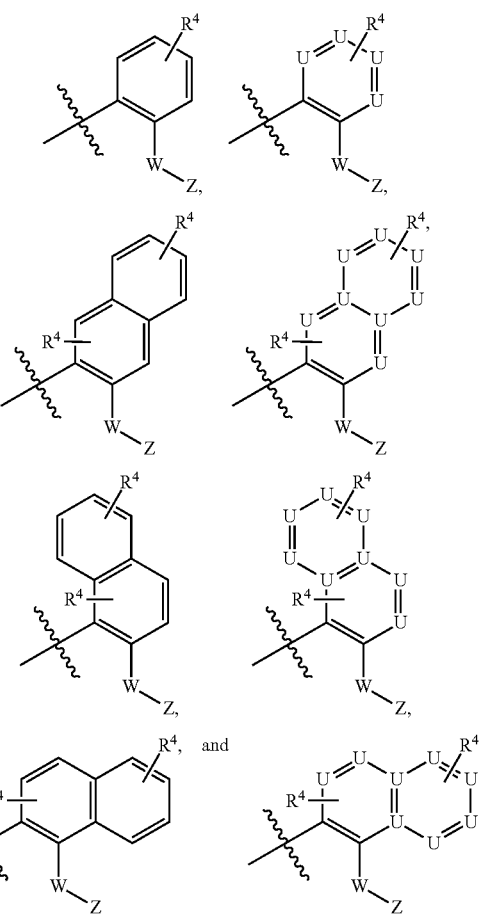

wherein U is selected from atoms C, S, O or N; and wherein $R^4$ is as described above.

In some embodiments, the invention provides compounds of formula I or formula II as described above, and pharmaceutically acceptable salts thereof, wherein W and Z are taken together to form a masked nucleophilic moiety selected from:

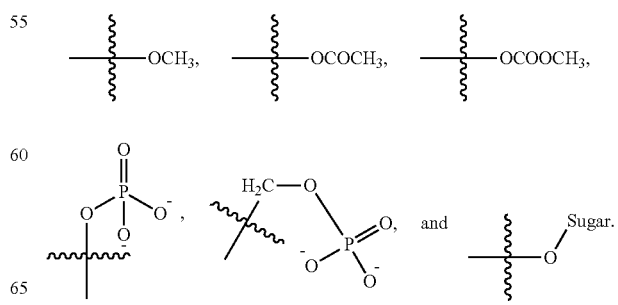

In some embodiments, the invention provides a compound selected from:
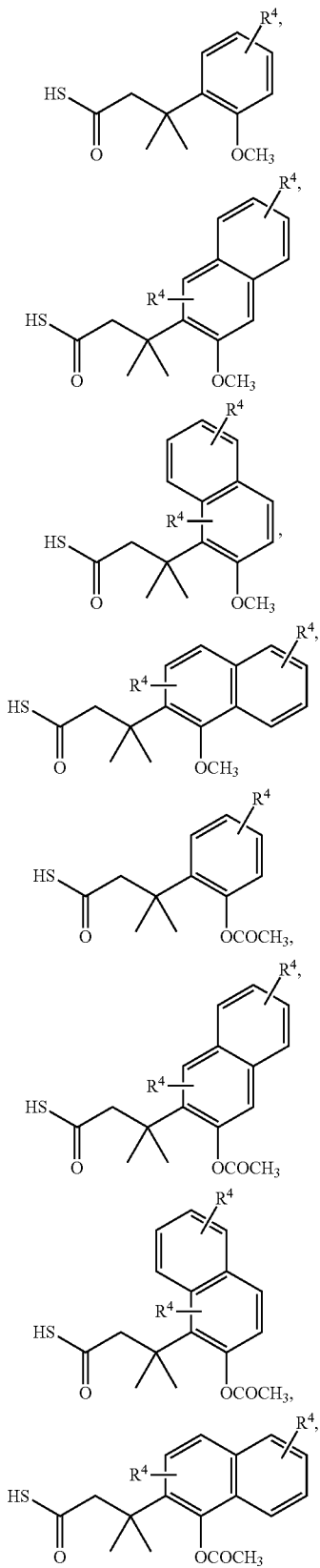
-continued
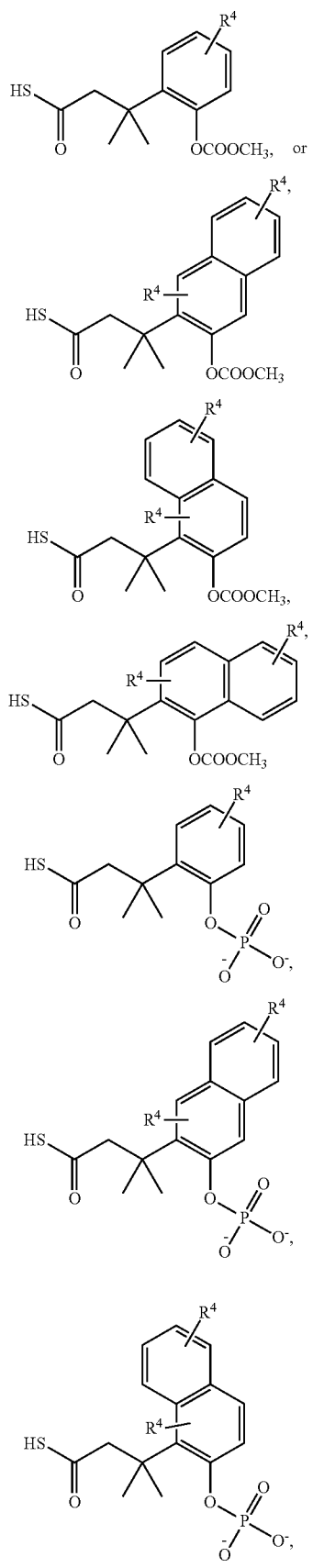

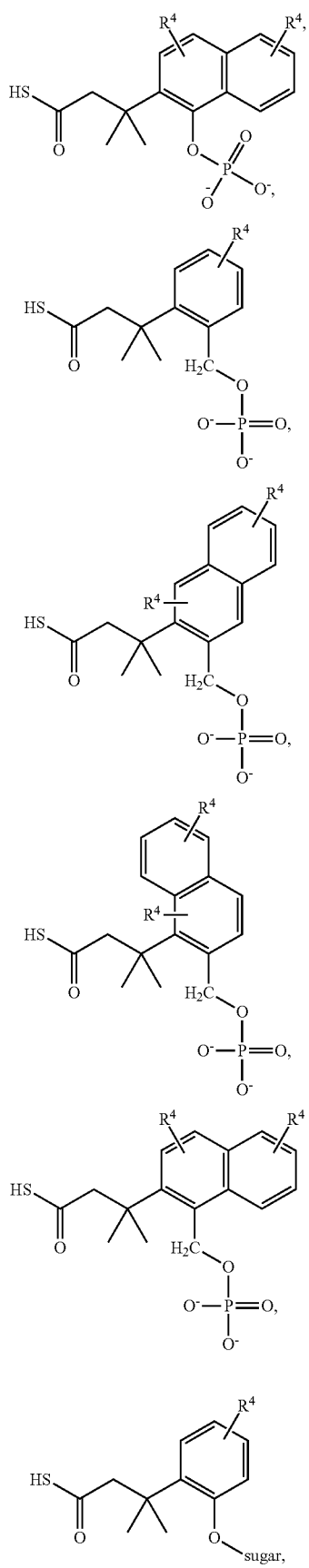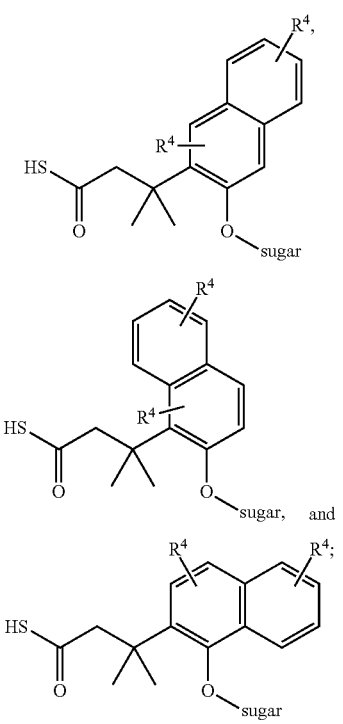
and pharmaceutically acceptable salts thereof, wherein $R^4$ is as described above.
In some embodiments, the compound of formula I, or a pharmaceutically acceptable salt thereof, is selected from:
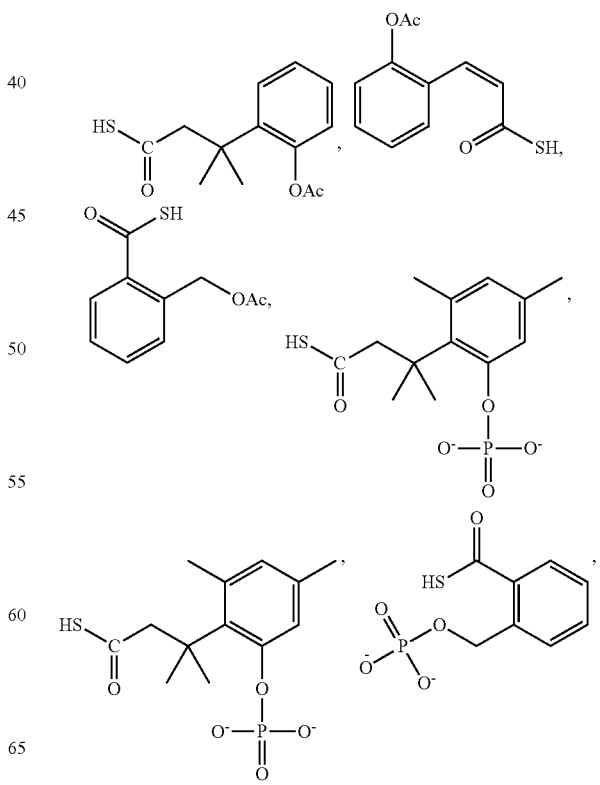

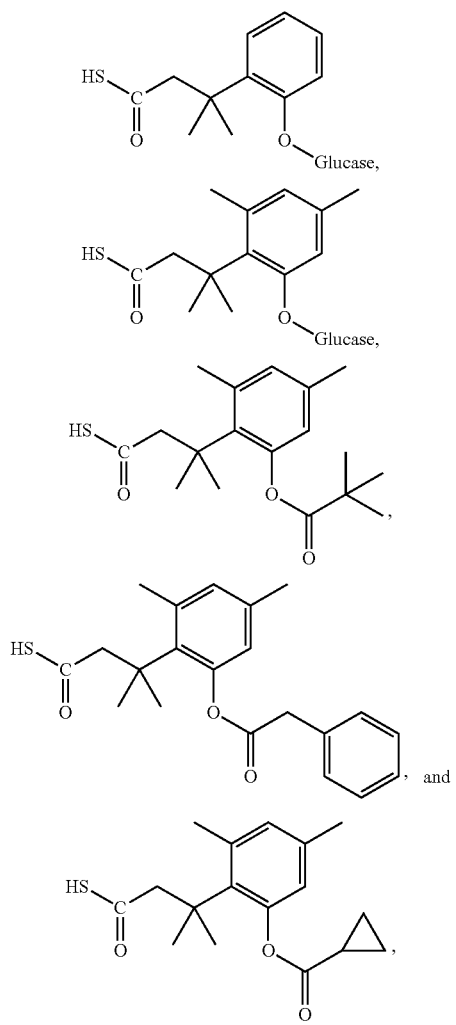
and pharmaceutically acceptable salts thereof.
In some embodiments, the compound is selected from:
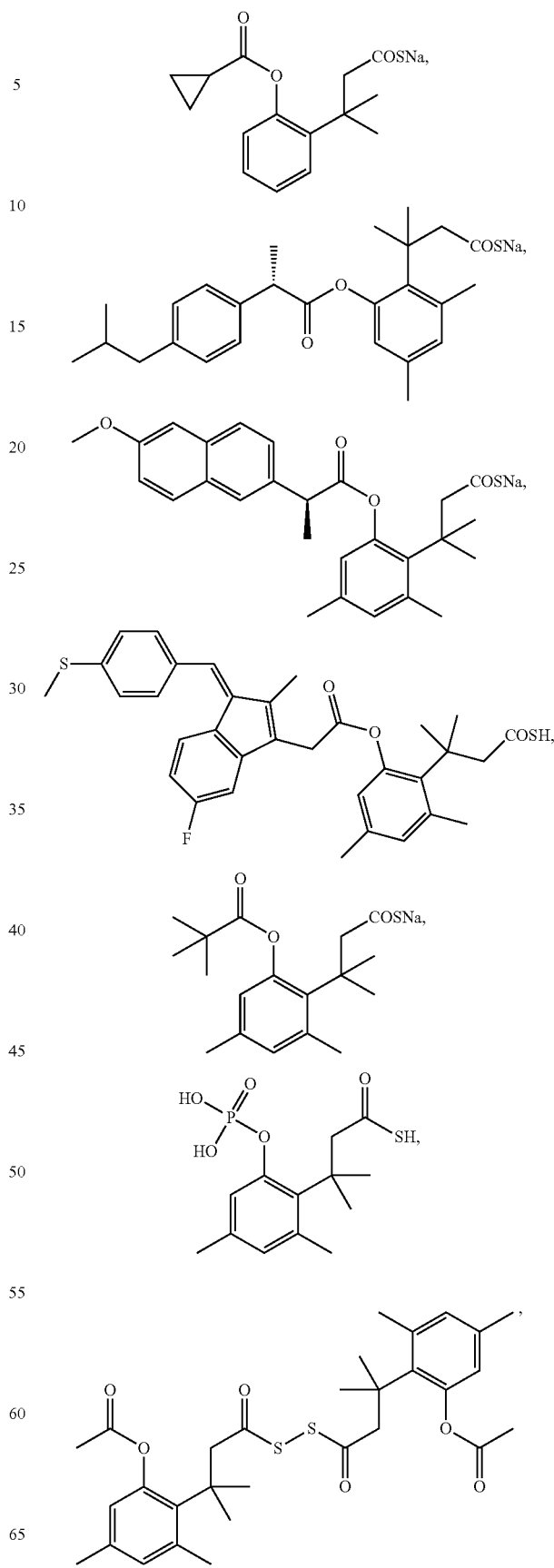

-continued

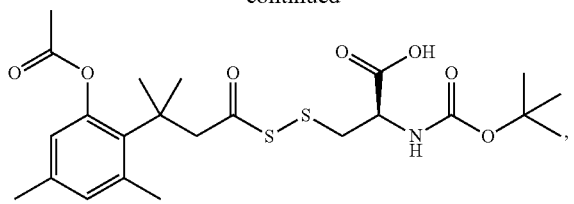

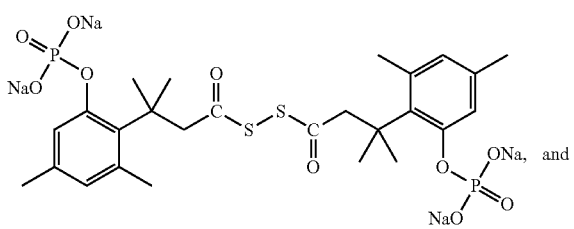

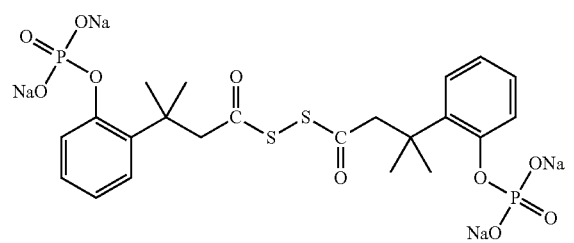

and pharmaceutically acceptable salts thereof.

In some embodiments, the compound is:

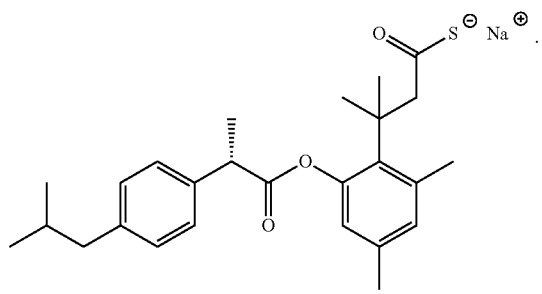 [SMILES: Cc1cc(C)c(C(C)(C)CC(=O)[S-])c(OC(=O)[C@@H](C)c2ccc(CC(C)C)cc2)c1 ; [Na+]]

In some embodiments, the compound is:

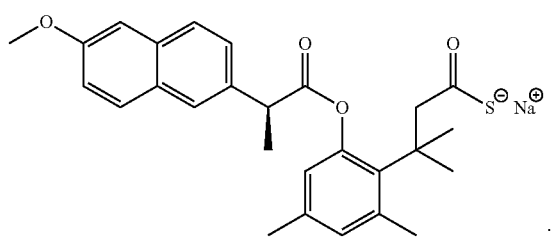 [SMILES: COc1ccc2cc([C@H](C)C(=O)Oc3cc(C)cc(C)c3C(C)(C)CC(=O)[S-])ccc2c1 ; [Na+]]

In some embodiments, the compound is:

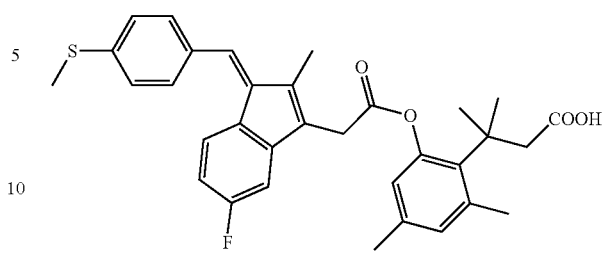

In some embodiments, the invention provides compounds of Formula I and Formula Ia, as well as pharmaceutically acceptable salts thereof, wherein Z is $R^7$, and $R^7$ is a non-steroidal anti-inflammatory drug (NSAID).

Any suitable NSAID can be used as a drug moiety in the compounds of the invention. In some embodiments, the NSAID is selected from ibuprofen, naproxen, sulindac, diclofenac, celecoxib, diflunisal, piroxicam, indomethacin, etodolac, meloxicam, ketoprofen, mefenamic acid, nabumetone, tolmetin, ketorolac tromethamine, choline magnesium trisalicylate, rofecoxib, aspirin, and paracetamol, and pharmaceutically acceptable salts thereof. The NSAID can be a cyclooxygenase-2 inhibitor (i.e., a COX-2 inhibitor) such as celecoxib, etoricoxib, lumiracoxib, parecoxib, rofecoxib, or vladecoxib.

Other drug moieties can also be included in the precursor compounds of the invention. In certain embodiments, the invention provides precursor compounds wherein the drug moiety is a drug for treating a cardiovascular condition, an ophthalmic condition, a neurological condition, a urological condition, diabetes, inflammation, hypertension, asthma, gastric injury, irritable bowel syndrome, kidney dysfunction, sepsis, ischemia, respiratory distress syndrome, thrombosis, or cancer. In some embodiments, the drug moiety is a drug known to treat myocardial infarction, heart failure, heart stroke, cardiomyopathy, myocardial fibrosis or angina pectoris. In some embodiments, the drug moiety is a drug known to treat Parkinson's disease or Alzheimer's disease. In some embodiments, the drug moiety is a drug known to treat erectile dysfunction, prostatic hypertrophy, or urinary tract malfunction. In some embodiments, the drug moiety is a drug known to treat lung cancer, breast cancer, prostate cancer, brain cancer, bone cancer, bladder cancer, cervical cancer, gastric cancer, oral cancer, ovarian cancer, testicular cancer, liver cancer, rectal cancer, retinal cancer, urethral cancer, uterine and vaginal cancer. In some embodiments, the drug moiety is a drug known to treat arthritis.

Drug moieties, including NSAID drug moieties, can be bonded directly to the hydrogen sulfide precursor compounds (e.g., via ester linkages). Alternatively, drug moieties, including NSAID drug moieties, can be bonded to the hydrogen sulfide precursor compounds via cleavable linkers (e.g., an enzymatically cleavable linker, a pH-labile linker, or a redox-sensitive linker). In some embodiments, the NSAID is ibuprofen. In some embodiments, the NSAID is naproxen. In some embodiments, the NSAID is sulindac.

In some embodiments, the invention provides compounds according to Formula A:

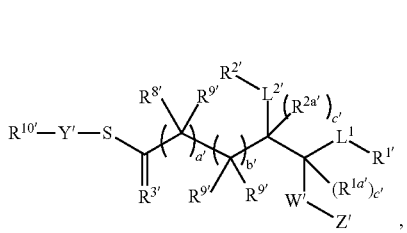

and pharmaceutically acceptable salts thereof, wherein:

$R^{1'}$ and $R^{2'}$ are taken together to form $C_3$-$C_6$ cycloalkyl, $C_6$-$C_{10}$ aryl, 3- to 10-membered heterocyclyl, or 3- to 10-membered heteroaryl, each of which is optionally substituted with 1-3 $R^{4'}$;

each $R^{1a'}$ and $R^{2a'}$ is independently selected from H and $C_{1-6}$ alkyl;

each $R^{4'}$ is independently selected from $C_1$-$C_6$ alkyl, $C_1$-$C_6$ alkoxy, $C_1$-$C_6$ haloalkyl, $C_1$-$C_6$ haloalkoxy, $C_1$-$C_6$ aminoalkyl, $C_1$-$C_6$ aminoalkoxy, $C_1$-$C_6$ thioalkyl, $C_1$-$C_6$ thioalkoxy, $C_{3-6}$ cycloalkyl, $C_{6-10}$ aryl, 6-10 membered heterocyclyl, —C(=O)$R^{5'}$, —C(=O)O$R^{5'}$, —C(=O)N$R^{5'}$, halo, —CN, —$NO_2$, —$N_3$, and —NH$R^{5'}$, wherein each $R^{5'}$ is independently selected from H and $C_1$-$C_4$ alkyl;

$L^{1'}$ and $L^{2'}$ are independently selected from a bond, —($CH_2$)$_{x'}$—, —$SO_2$—, —CO—, —N$R^{5'}$—, —N$R^5$CO—, and —N$R^{5'}$ $SO_2$—, wherein each $R^{5'}$ is independently selected from H and $C_1$-$C_4$ alkyl, and each subscript x' is independently 0, 1, 2, 3, or 4;

$R^{3'}$ is selected from O, S, and NH;

W' is selected from O, S, and NH;

Z' is selected from —$R^{6'}$, —C(=O)O$R^{6'}$, —($CH_2$)$_x$O$R^{6'}$, —($CH_2$)$_x$C(=O)O$R^{6'}$, —($CH_2$)$_x$OC(=O)$R^{6'}$, —($CH_2$)$_{x'}$, —OP(=O)(O$R^{6'}$)$_{x'}$, —OP(=O)(O$R^{6'}$)$_{x'}$, and $R^{7'}$; wherein $R^{6'}$ is selected from H, $C_1$-$C_4$ alkyl, $C_2$-$C_4$ alkenyl, $C_2$-$C_4$ alkynyl, $C_3$-$C_4$ cycloalkyl, wherein each subscript x' is independently 0, 1, 2, 3, or 4; and wherein $R^{7'}$ is a sugar or a drug;

$R^{8'}$ and $R^{9'}$ are independently selected from H, $C_1$-$C_6$ alkyl, $C_1$-$C_6$ alkoxy, $C_1$-$C_6$ haloalkyl, $C_1$-$C_6$ haloalkoxy, $C_1$-$C_6$ aminoalkyl, $C_1$-$C_6$ amino alkoxy, $C_1$-$C_6$ thioalkyl, $C_1$-$C_6$ thioalkoxy, $C_{3-6}$ cycloalkyl, $C_{6-10}$ aryl, C(=O)$R^{5'}$, C(=O)O$R^{5'}$, C(=O)N$R^{5'}$, halo, CN, $NO_2$, $N_3$, and NH$R^{5'}$, wherein one $R^{8'}$ or $R^{9'}$ is optionally taken together with one $R^{8'}$ or $R^{9'}$ to form a double bond;

Y' is selected from —S—, —(O)CS—, —NH—, and H, provided that when Y is H, $R^{10'}$ is absent;

wherein $R^{10'}$, when present, is selected from H, alkyl, aryl, cycloalkyl and heteroaryl;

subscripts a' and b' are independently 0, 1, 2, or 3; and each subscript c' is 0 when $R^1$ and $R^2$ form aryl or heteroaryl; or each subscript c' is 1 when $R^1$ and $R^2$ form cycloalkyl or heterocyclyl.

In general, masking groups are linked to compounds of formula I through a hydrolysable bond as shown, for example, in Scheme 3 where the masking group is labeled $R^a$.

Scheme 3

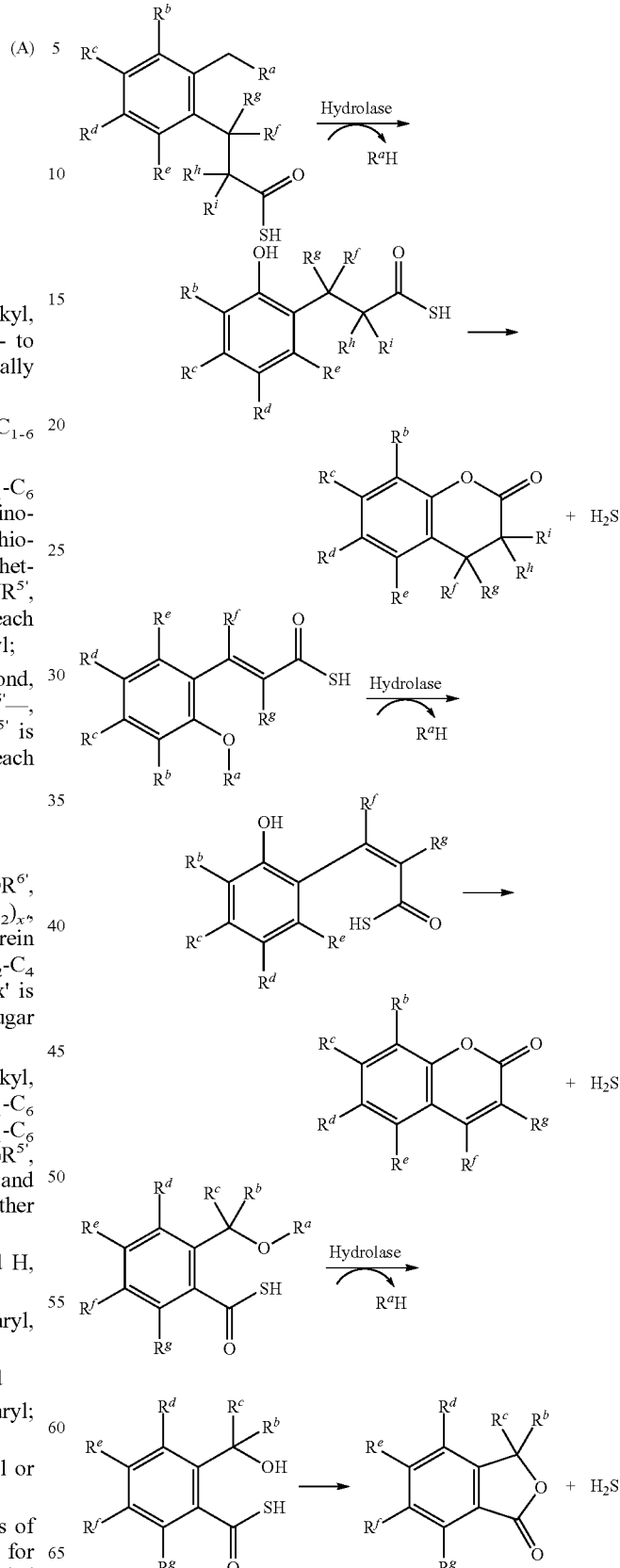

In some embodiments, masking groups are linked to compounds of formula I through an ester bond as shown, for example, in Scheme 4 where the masking group is labeled $R^1$.
Scheme 4
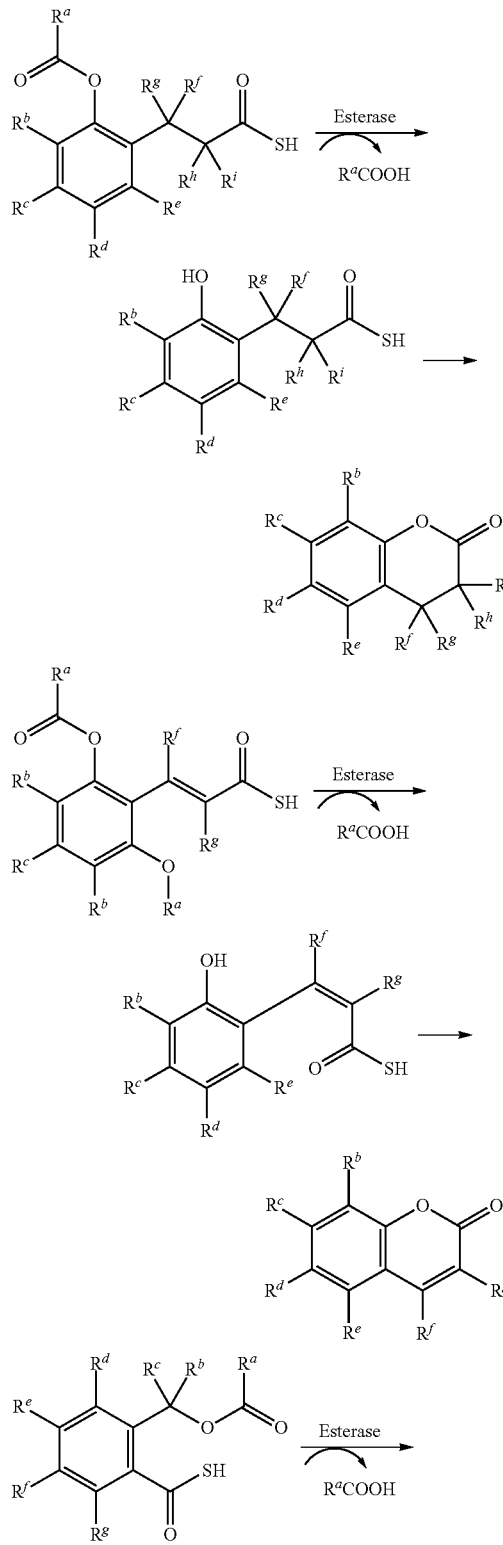
In some embodiments, the masking group is a sugar linked through a glycosidic bond as shown, for example, in Scheme 5.
Scheme 5
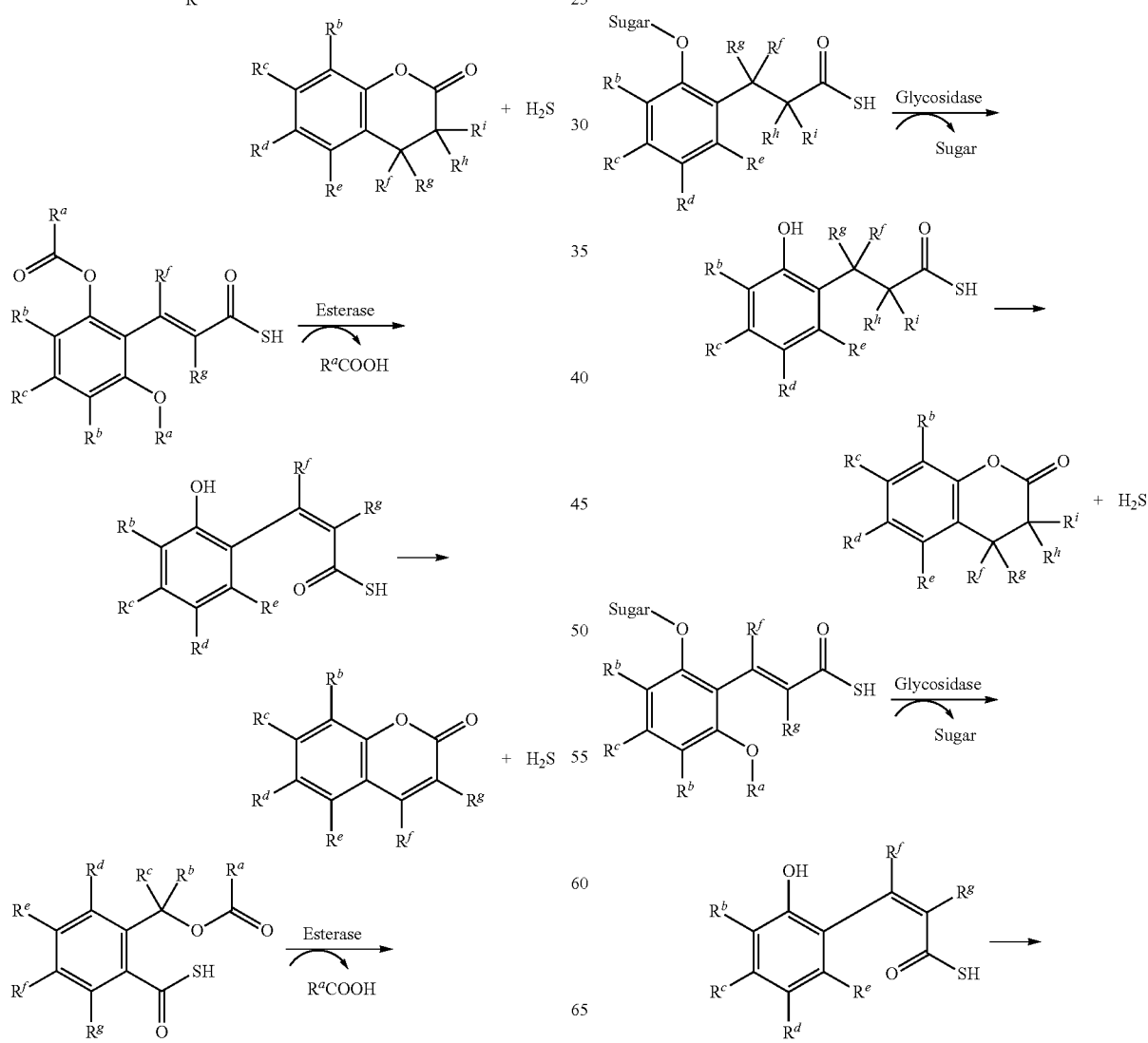

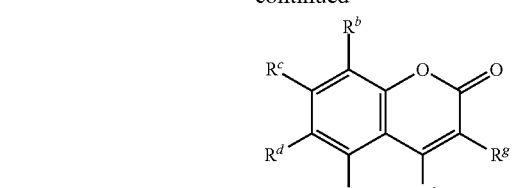

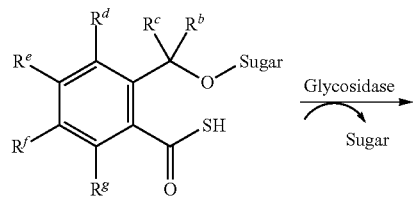

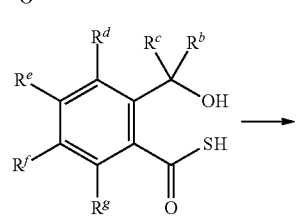

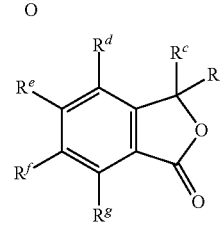

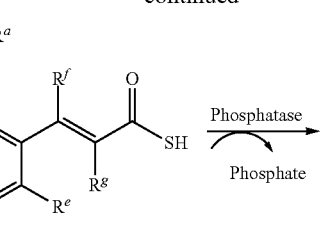

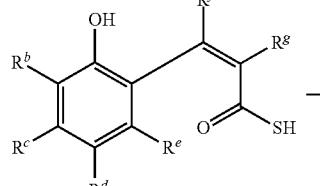

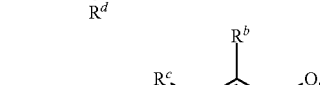

In some embodiments, masking groups are linked to compounds of formula I through a phosphate bond as shown, for example, in Scheme 6 where the masking group is labeled $R^a$.

Scheme 6

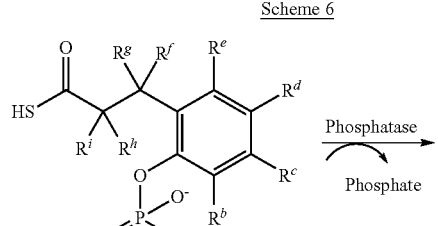

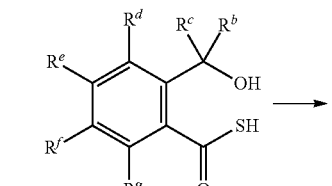

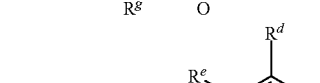

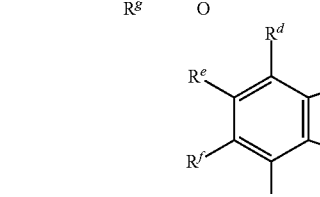

In some embodiments, the invention provides a method of forming hydrogen sulfide. The method includes contacting a precursor compound according to Formula I with an unmasking agent; wherein the contacting is conducted under conditions sufficient for cyclization of the precursor compound via lactone or lactam formation; thereby releasing hydrogen sulfide from the precursor compound.

V. Pharmaceutical Compositions of Compounds of the Invention

In a related aspect, the invention provides pharmaceutical compositions containing a hydrogen sulfide precursor of the invention and a pharmaceutically acceptable carrier or excipient.

The compounds can be administered orally, topically, parenterally, by inhalation or spray or rectally in dosage unit formulations. The term "administration by injection" includes intravenous, intramuscular, subcutaneous and parenteral injections, as well as use of infusion techniques. One or more compounds can be present in association with one or more non-toxic pharmaceutically acceptable carriers and if desired other active ingredients.

Compositions intended for oral use can be prepared according to any suitable method known to the art for the manufacture of pharmaceutical compositions. Such compositions can contain one or more agents selected from diluents, sweetening agents, flavoring agents, coloring agents and preserving agents in order to provide palatable preparations. Tablets contain the active ingredient in admixture with non-toxic pharmaceutically acceptable excipients which are suitable for the manufacture of tablets. These excipients can be, for example, inert diluents, such as calcium carbonate, sodium carbonate, lactose, calcium phosphate or sodium phosphate; granulating and disintegrating agents, for example, corn starch, or alginic acid; and binding agents, for example magnesium stearate, stearic acid or talc. The tablets can be uncoated or they can be coated by known techniques to delay disintegration and adsorption in the gastrointestinal tract and thereby provide a sustained action over a longer period. For example, a time delay material such as glyceryl monostearate or glyceryl distearate can be employed. These compounds can also be prepared in solid, rapidly released form.

Compositions for oral use can also be formulated as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents can be a naturally occurring phosphatide, for example, lecithin, or condensation products or an alkylene oxide with fatty acids, for example polyoxyethylene stearate, or condensation products of ethylene oxide with long chain aliphatic alcohols, for example heptadecaethylene oxycetanol, or condensation products of ethylene oxide with partial esters derived from fatty acids and hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, can also be present.

The compounds can also be in the form of non-aqueous liquid formulations, e.g., oily suspensions which can be formulated by suspending the active ingredients in a vegetable oil, for example arachis oil, olive oil, sesame oil or peanut oil, or in a mineral oil such as liquid paraffin. The oily suspensions can contain a thickening agent, for example beeswax, hard paraffin or cetyl alcohol. Sweetening agents such as those set forth above, and flavoring agents can be added to provide palatable oral preparations. These compositions can be preserved by the addition of an anti-oxidant such as ascorbic acid.

Pharmaceutical compositions of the invention can also be in the form of oil-in-water emulsions. The oily phase can be a vegetable oil, for example olive oil or arachis oil, or a mineral oil, for example liquid paraffin or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions can also contain sweetening and flavoring agents.

Syrups and elixirs can be formulated with sweetening agents, for example glycerol, propylene glycol, sorbitol or sucrose. Such formulations can also contain a demulcent, a preservative and flavoring and coloring agents.

The compounds can also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols.

VI. Methods of Hydrogen Sulfide Delivery

The compounds and methods of the invention have applications in any therapeutic approach in which hydrogen sulfide requirements are addressed. The requirement may be due to deficiency of hydrogen sulfide in a subject. The compounds and methods can also be used to treat patients having normal levels of endogenous hydrogen sulfide but who would benefit from an increase in hydrogen sulfide. The invention therefore relates to methods for treating and preventing diseases that are mediated at least in part by endogenous hydrogen sulfide.

Accordingly, another aspect of the invention affords a method of providing hydrogen sulfide to a subject in need thereof. In certain embodiments, the method includes administering a compound of the invention, or a pharmaceutical composition containing a composition of the invention, to a subject under conditions sufficient to form hydrogen sulfide. In some embodiments, the method includes administering a compound according to Formula I to the subject. In some embodiments, the hydrogen sulfide is used for the treatment of a condition selected from a cardiovascular condition, an ophthalmic condition, a neurological condition, a urological condition, diabetes, inflammation, hypertension, asthma, gastric injury, irritable bowel syndrome, kidney dysfunction, sepsis, ischemia, respiratory distress syndrome, thrombosis and cancer. The compounds of the invention can be administered alone as a monotherapy or in combination with other active agents.

In some embodiments, the hydrogen sulfide release is used for treatment of a cardiovascular condition. In some embodiments, the cardiovascular condition is selected from myocardial infarction, heart failure, heart stroke, cardiomyopathy, myocardial fibrosis and angina pectoris.

In some embodiments, the hydrogen sulfide release is used for treatment of cancers. In some embodiments, the cancer is selected from lung, breast, prostate, brain, bone, bladder, cervical, gastric, oral, ovarian, testicular, liver, rectal, retinal, urethral, uterine and vaginal cancer.

The cancer can be a carcinoma, a sarcoma, an adenocarcinoma, a lymphoma, a leukemia, and a solid and lymphoid cancer. Examples of different types of cancer include, but are not limited to, lung cancer (e.g., non-small cell lung cancer or NSCLC), ovarian cancer, prostate cancer, colorectal cancer, liver cancer (i.e., hepatocarcinoma), renal cancer (i.e., renal cell carcinoma), bladder cancer, breast cancer, thyroid cancer, pleural cancer, pancreatic cancer, uterine cancer, cervical cancer, testicular cancer, anal cancer, pancreatic cancer, bile duct cancer, gastrointestinal carcinoid tumors, esophageal cancer, gall bladder cancer, appendix cancer, small intestine cancer, stomach (gastric) cancer, cancer of the central nervous system, skin cancer, choriocarcinoma, head and neck cancer, blood cancer, osteogenic sarcoma, fibrosarcoma, neuroblastoma, glioma, melanoma, B-cell lymphoma, non-Hodgkin's lymphoma, Burkitt's lymphoma, Small Cell lymphoma, Large Cell lymphoma, monocytic leukemia, myelogenous leukemia, acute lymphocytic leukemia, acute myelocytic leukemia, and multiple myeloma.

In some embodiments, the hydrogen sulfide release is used for treatment of arthritis. In some embodiments, the hydrogen sulfide release is used for treatment of Alzheimer's disease. In some embodiments, the hydrogen sulfide release is used for treatment of Parkinson's disease.

The specific dose level selected for any particular patient will depend upon a variety of factors, including the activity of the specific compound employed, the age, body weight, general health, sex, diet, time of administration, route of administration, and rate of excretion, drug combination and the severity of the condition undergoing therapy.

Hydrogen sulfide precursors can be administered at any suitable dose in the methods of the invention. In general, hydrogen sulfide precursor is administered at a dose ranging from about 0.1 milligrams to about 1000 milligrams per kilogram of a subject's body weight (i.e., about 0.1-1000 mg/kg). The dose of hydrogen sulfide precursor can be, for example, about 0.1-1000 mg/kg, or about 1-500 mg/kg, or about 25-250 mg/kg, or about 50-100 mg/kg. The dose of hydrogen sulfide precursor can be about 1, 2, 3, 4, 5, 10, 15, 20, 25, 30, 35, 40, 45, 50, 55, 60, 65, 70, 75, 85, 90, 95, 100, 150, 200, 250, 300, 350, 400, 450, 500, 550, 600, 650, 700, 750, 800, 850, 900, 950 or 1000 mg/kg. The dose of hydrogen sulfide precursor can be administered at a dose below about 1, below about 2, below about 3, below about 4, below about 5, below about 10, below about 15, below about 20, below about 25, below about 30, below about 35, below about 40, below about 45, below about 50, below about 55, below about 60, below about 65, below about 70, below about 75, below about 85, below about 90, below about 95, below about 100, below about 150, below about 200, below about 250, below about 300, below about 350, below about 400, below about 450, below about 500, below about 550, below about 600, below about 650, below about 700, below about 750, below about 800, below about 850, below about 900, below about 950, or below about 1000 mg/kg. In some embodiments, hydrogen sulfide precursor is administered at a dose below 200 mg of compound per kg of the subject's body weight (200 mg/kg). In some embodiments, hydrogen sulfide precursor is administered at a dose below 100 mg/kg. In some embodiments, hydrogen sulfide precursor is administered at a dose below 50 mg/kg. In some embodiments, hydrogen sulfide precursor is administered at a dose below 20 mg/kg.

The dosages can be varied depending upon the needs of the patient, the severity of the hydrogen sulfide requirement being treated, and the particular formulation being administered. The dose administered to a patient should be sufficient to result in a beneficial therapeutic response in the patient. The size of the dose will also be determined by the existence, nature, and extent of any adverse side-effects that accompany the administration of the drug in a particular patient. Determination of the proper dosage for a particular situation is within the skill of the typical practitioner. The total dosage can be divided and administered in portions over a period of time suitable to address the hydrogen sulfide requirement.

Administration of hydrogen sulfide precursor can be conducted for a period of time which will vary depending upon the nature of the particular hydrogen sulfide requirement, its severity and the overall condition of the patient. Administration can be conducted, for example, hourly, every 2 hours, three hours, four hours, six hours, eight hours, or twice daily including every 12 hours, or any intervening interval thereof. Administration can be conducted once daily, or once every 36 hours or 48 hours, or once every month or several months. Following treatment, a patient can be monitored for changes in his or her condition and for alleviation of the symptoms of the hydrogen sulfide requirement. The dosage of the hydrogen sulfide precursor can either be increased in the event the patient does not respond significantly to a particular dosage level, or the dose can be decreased if an alleviation of the symptoms of the hydrogen sulfide requirement is observed, or if the hydrogen sulfide requirement has been ablated, or if unacceptable side effects are seen with a particular dosage.

A therapeutically effective amount of hydrogen sulfide precursor can be administered to the subject in a treatment regimen including intervals of at least 1 hour, or 6 hours, or 12 hours, or 24 hours, or 36 hours, or 48 hours between dosages. Administration can be conducted at intervals of at least 72, 96, 120, 168, 192, 216, or 240 hours, or the equivalent amount of days. The dosage regimen can consist of two or more different interval sets. For example, a first part of the dosage regimen can be administered to a subject multiple times daily, daily, every other day, or every third day. The dosing regimen can start with dosing the subject every other day, every third day, weekly, biweekly, or monthly. The first part of the dosing regimen can be administered, for example, for up to 30 days, such as 7, 14, 21, or 30 days. A subsequent second part of the dosing regimen with a different interval administration administered weekly, every 14 days, or monthly can optionally follow, continuing for 4 weeks up to two years or longer, such as 4, 6, 8, 12, 16, 26, 32, 40, 52, 63, 68, 78, or 104 weeks. Alternatively, if the hydrogen sulfide requirement decreases, the dosage may be maintained or kept at lower than maximum amount. If the requirement increases, the first dosage regimen can be resumed until an improvement is seen, and the second dosing regimen can be implemented again. This cycle can be repeated multiple times as necessary.

VII. Examples

Example 1. H₂S Precursor HP-101

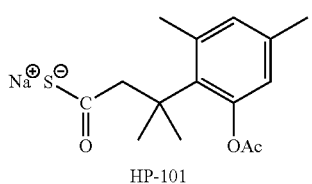 [SMILES: [Na+] ; CC(=O)Oc1cc(C)cc(C)c1C(C)(C)CC(=O)[S-]]

HP-101

Synthesis of Sodium 3-(2-acetoxy-4,6-dimethylphenyl)-3-methylbutanethioate (HP-101)

A solution of 3-(2-acetoxy-4,6-dimethylphenyl)-3-methylbutanoic acid (78 mg, 0.3 mmol), Lawesson's reagent (60 mg, 0.15 mmol) and 1.5 mL $CH_2Cl_2$ in a sealed tube was subjected to microwave irradiation (100° C., 6 min). After completion of reaction, the solution mixture was diluted with $CH_2Cl_2$. The organic layer was washed by 1 N HCl and brine, dried over anhydrous sodium sulfate. Then, after filtration, $CH_2Cl_2$ was removed under vacuum. The residue was purified by flash column chromatography (hexane:ethyl acetate=10:1) to give an oil (59 mg). Then the oil was dissolved in the NaOH solution (8.4 mg in 2 mL methanol) at −78° C., and methanol was removed followed by addition of 2 mL diethyl ether. The final product (HP-101) was collected from diethyl ether as a white solid (57 mg, 67%). $^1$H NMR ($CD_3OD$, 400 MHz): δ 6.80 (s, 1H, Ph-H), 6.53 (s, 1H, Ph-H), 3.33 (s, —$CH_2$—CO—), 2.58 (s, 3H, Ph-$CH_3$), 2.32 (s, 3H, —CO—$CH_3$), 2.21 (s, 3H, Ph-$CH_3$), 1.54 (s, 6H, Ph-C($CH_3$)$_2$—), $^{13}$C NMR ($CD_3OD$, 100 MHz): δ219.0, 172.4, 150.7, 139.5, 137.0, 136.4, 132.9, 123.9, 64.4, 40.1, 31.8, 25.7, 22.0, 20.2. MS calcd. For $C_{15}H_{19}O_3S$ [M−H]⁻ 279.1055, found: 279.1051.

Example 2. H₂S Precursor Sodium 3-(2-acetoxyphenyl)-3-methylbutanethioate (HP-103)

Hydrogen sulfide precursor HP-103 was synthesized in 8 steps as shown in Scheme 7.

Scheme 7

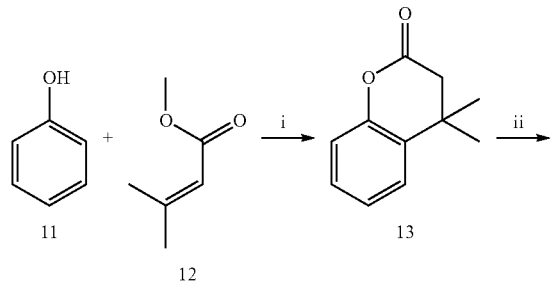

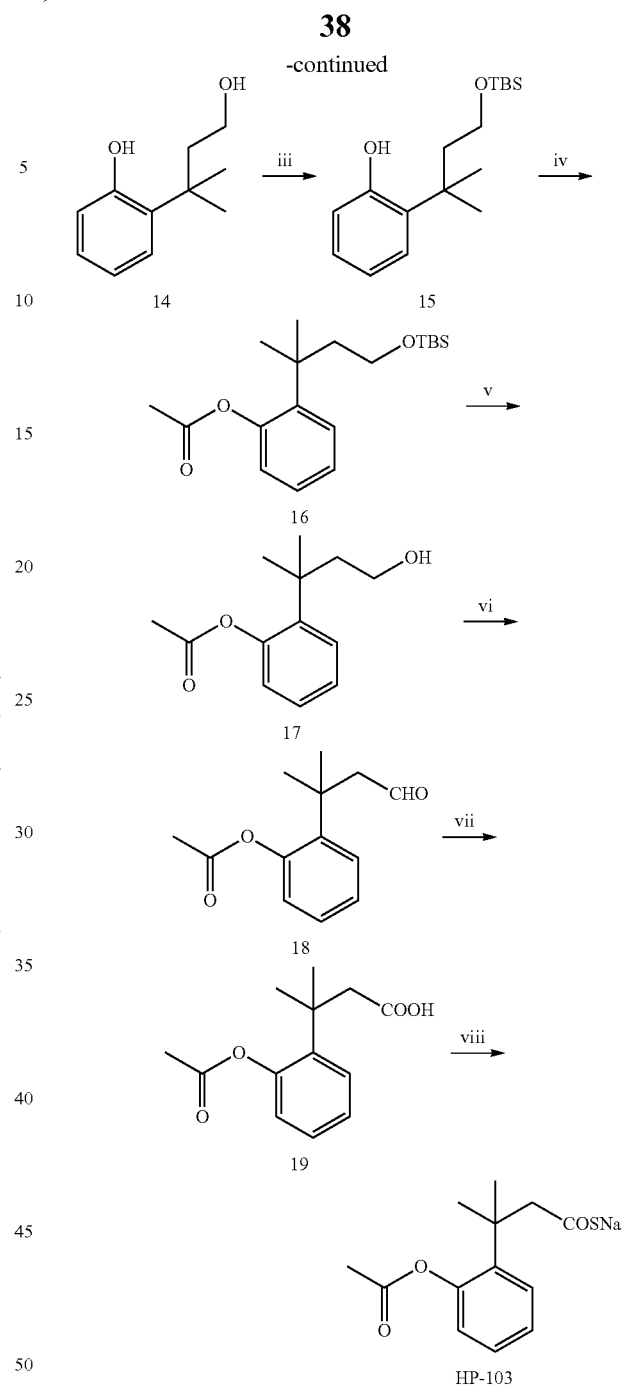

Reagents and conditions (i) MeOSO₃H, 70° C., (ii) LiAlH4, THF, 25° C., (iii) TBDMSCl, DMF, imidazole, (iv) Acetic anhydride, DMAP, 3 h; (v) AcOH/H₂O, THF, rt, 12 h; (vi) PCC, DCM, rt, 2 h; (vii) NaClO₂/NaH₂PO₄, 2-methylbut-2-ene, t-BuOH, rt, 2 h; (viii) 1) Lawesson's reagent, DCM, microwave, 6 min; 2) NaOH, methanol, -78° C.

Synthesis of 2-O-((tert-butyldimethylsilyl)oxy)-2-methylpropan-2-yl)phenyl acetate (16)

To a solution of 2-(4-((tert-butyldimethylsilyl)oxy)-2-methylbutan-2-yl)phenol (15, 1.53 g, 5.6 mmol) in dichloromethane (10 mL), was added acetic anhydride (1.63 g, 3 mmol), Et₃N (1.62 g, 16 mmol and DMAP (0.29 g, 2.4 mmol). The mixture was stirred at room temperature for 2 h. The reaction mixture was quenched with H₂O (10 mL) and extracted in ethyl acetate (2×50 mL). The combined organic phase was dried over Na₂SO₄ and evaporated under reduced pressure to achieve the crude product, which was then purified by chromatography to obtain colorless oil (1.6 g, 91%). ¹H NMR (400 MHz, CDCl₃): δ 7.33 (dd, J=7.6 Hz, 1.2 Hz, 1H), 7.25-7.21 (m, 1H), 7.18-7.14 (m, 1H), 7.00 (dd, J=7.6 Hz, 1.2 Hz, 1H), 3.41 (t, J=7.6 Hz, 2H), 2.33 (s, 3H) 2.01 (t, J=7.6 Hz, 2H), 1.36 (s, 6H), 0.84 (s, 9H), −0.04 (s, 6H).

Synthesis of 2-(4-hydroxy-2-methylbutan-2-yl)phenyl acetate (17)

To a solution of 2-(1-((tert-butyldimethylsilyl)oxy)-2-methylpropan-2-yl)phenyl acetate (16), in 3 ml tetrahydrofuran (1.50 g, 4.46 mmol), was added H₂O (3 mL) and AcOH (9 mL). The reaction mixture was stirred at room temperature for 12 h, quenched with H₂O (10 mL), and extracted in ethyl acetate (2×50 mL). The combined organic phase was dried over Na₂SO₄ and evaporated under reduced pressure to obtain the crude product, which was purified by chromatography to obtain colorless oil (900 mg, 91%). ¹H NMR (400 MHz, CDCl₃): δ 7.32 (dd, J=7.6 Hz, 1.6 Hz, 1H), 7.25-7.21 (m, 1H), 7.18-7.14 (m, 1H), 6.98 (dd, J=7.6 Hz, 1.6 Hz, 1H), 3.40 (t, J=7.6 Hz, 2H), 2.34 (s, 3H), 1.99 (t, J=7.6 Hz, 2H), 1.37 (s, 6H).

Synthesis of 2-(2-methyl-4-oxobutan-2-yl)phenyl acetate (18)

To a solution of PCC (1.55 g, 7.2 mmol) in dichloromethane (5 mL), a solution of (2-(4-hydroxy-2-methylbutan-2-yl)phenyl acetate (17, 710 mg, 3.20 mmol) in dichloromethane (5 mL) was dropwise added at room temperature. After 2 h, the pure product was obtained by column chromatography as colorless oil (650 mg, 92%). ¹H NMR (400 MHz, CDCl₃): δ 9.45 (t, J=2.8 Hz, 1H) 7.38 (dd, J=7.6 Hz, 1.6 Hz, 1H), 7.30-7.26 (m, 1H), 7.22-7.18 (m, 1H), 7.05 (dd, J=7.6 Hz, 1.6 Hz, 1H), 2.79 (d, J=2.8 Hz, 2H), 2.36 (s, 3H), 1.46 (s, 6H).

Synthesis of 3-(2-acetoxyphenyl)butanoic acid (19)

To a solution of 2-(2-methyl-4-oxobutan-2-yl)phenyl acetate (18, 600 mg, 2.73 mmol) in t-BuOH (12 mL) and 2-methylbut-2-ene (2.5 mL) was dropwise added NaClO₂ (564 mg, 6.27 mmol) in 0.67M NaH₂PO₄ (2.0 mL) at room temperature. After 2 h, the reaction mixture was quenched with H₂O (20 mL), and extracted in ethyl acetate (2×50 ml). The combined organic phase was dried over Na₂SO₄ and evaporated under reduced pressure to afford the crude product, which was purified by chromatography to obtain a white solid (510 mg, 79%). ¹H NMR (400 MHz, CDCl₃): δ 7.38 (dd, J=8.0 Hz, 1.6 Hz, 1H), 7.27-7.23 (m, 1H), 7.19-7.15 (m, 1H), 7.03 (dd, J=8.0 Hz, 1.6 Hz, 1H), 2.79 (s, 2H), 2.35 (s, 3H) 1.47 (s, 6H).

Synthesis of sodium 3-(2-acetoxyphenyl)-3-methylbutanethioate (HP-103)

To a solution of 3-(2-acetoxyphenyl)butanoic acid (19, 150 mg, 0.63 mmol) in dichloromethane (5 mL) was added Lawesson's reagent (128 mg). The mixture was microwaved at 100° C. for 6 min. The pure product was achieved by chromatography as colorless oil (125 mg). Then the oil was dissolved in NaOH solution (17.4 mg, in 2 mL methanol) at −78° C., and the methanol was removed and 2 mL diethyl ether was added. The final product was collected from diethyl ether as a white solid (122 mg, 63%). ¹H NMR (400 MHz, CDCl₃): δ 7.41 (d, J=1.6 Hz, 1H), 7.39-7.28 (m, 1H), 7.24-7.09 (m, 1H), 7.07 (d, J=1.6 Hz, 1H), 3.10 (s, 2H), 2.40 (s, 3H) 1.49 (s, 6H). MS calcd. for C₁₃H₁₅O₃S [M−H]⁻ 257.0742, found 257.0742.

Example 3. Sodium 3-(2-((cyclopropanecarbonyl)oxy)-4,6-dimethylphenyl)-3-methylbutanethioate (27)

Hydrogen sulfide precursor 27 was synthesized in 5 steps as shown in Scheme 8.

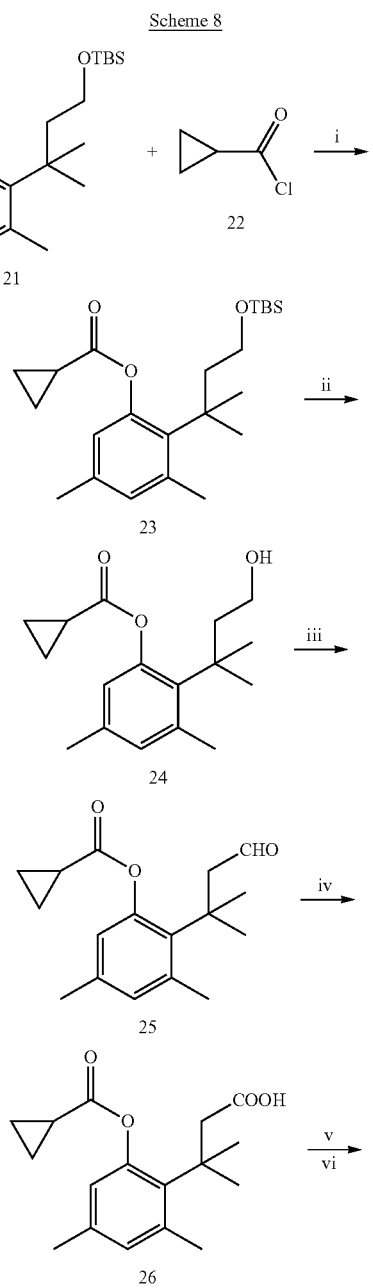

Scheme 8

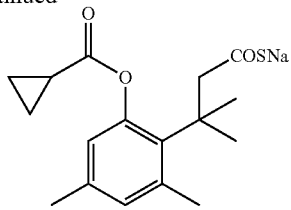

HP-102

Reagents and conditions (i) Et₃N, DCM, 0° C.-rt, 12 h; (ii) AcOH/H₂O, THF, rt, 12 h; (iii) PCC, DCM, rt, 2 h; (iv) NaClO₂/NaH₂PO₄, 2-methylbut-2-ene, t-BuOH, rt, 12 h; (v) Lawesson's Reagent, DCM, microwave, 6 min; (vi) NaOH, methanol, -78° C.

Synthesis of 2-(4-((tert-butyldimethylsilyl)oxy)-2-methylbutan-2-yl)-3,5-dimethylphenyl cyclopropanecarboxylate (23)

To a solution of 2-(4-((tert-butyldimethylsilyl)oxy)-2-methylbutan-2-yl)-3,5-dimethylphenol (21, 1.9 g, 5.9 mmol) and Et₃N (1.2 ml, 8.8 mmol) in dichloromethane (150 mL) was dropwise added cyclopropanecarbonyl chloride (22, 0.8 ml, 8.8 mmol) at 0° C. The mixture was allowed to warm to room temperature and stirred for 12 h, then quenched with the addition of H₂O (100 mL), and extracted with ethyl acetate (2×150 mL). The combined organic phase was dried over Na₂SO₄ and evaporated under reduced pressure to give the crude product, which was purified by chromatography to give a colorless oil (1.04 g, 46%). $^1$H NMR (400 MHz CDCl₃): δ6.79 (s, 1H), 6.56 (s, 1H), 3.50 (t, J=8.0 Hz, 2H), 2.52 (s, 3H), 2.22 (s, 3H), 2.06 (t, J=8.0 Hz, 2H), 1.86-1.80 (m, 1H), 1.49 (s, 6H), 1.17-1.13 (m, 2H), 1.01-0.95 (m, 2H), 0.85 (s, 9H), −0.02 (s, 6H); $^{13}$C NMR (CDCl₃): 174.1, 150.1, 138.4, 136.0, 134.3, 132.3, 123.2, 61.0, 46.1, 39.3, 32.0, 26.1, 25.4, 20.3, 18.4, 13.7, 8.9, −5.2.

Synthesis of 2-(4-hydroxy-2-methylbutan-2-yl)-3,5-dimethylphenyl cyclopropanecarboxylate (24)

To a solution of 2-(4-((tert-butyldimethylsilyl)oxy)-2-methylbutan-2-yl)-3,5-dimethylphenyl cyclopropanecarboxylate (23, 1.04 g, 2.7 mmol) in tetrahydrofuran (15 mL) was added H₂O (15 mL) and AcOH (45 mL). The reaction mixture was stirred at room temperature for 12 h, quenched with H₂O (50 mL), and extracted in ethyl acetate (2×150 mL). The combined organic phase was dried over Na₂SO₄ and evaporated under reduced pressure, and purified silica gel column chromatography as colorless oil (680 mg, 91%). $^1$H NMR (400 MHz CDCl₃): δ 6.81 (s, 1H), 6.55 (s, 1H), 3.54 (t, J=8.0 Hz, 2H), 2.52 (s, 3H), 2.22 (s, 3H), 2.06 (t, J=8.0 Hz, 2H), 1.87-1.82 (m, 1H), 1.51 (s, 6H), 1.18-1.14 (m, 2H), 1.04-0.99 (m, 2H); $^{13}$C NMR (CDCl₃): 174.8, 150.0, 138.5, 136.3, 134.1, 132.5, 123.4, 60.7, 45.9, 39.3, 32.2, 25.5, 20.3, 13.7, 9.1.

Synthesis of 3,5-dimethyl-2-(2-methyl-4-oxobutan-2-yl)phenylcyclopropanecarboxylate (25)

To a solution of PCC (1.5 g, 7.0 mmol) in dichloromethane (20 mL) was dropwise added 2-(4-hydroxy-2-methylbutan-2-yl)-3,5-dimethylphenyl cyclopropanecarboxylate (24, 0.96 g, 3.5 mmol) in dichloromethane (25 mL) at room temperature. After 2 h, the pure product was achieved by chromatography as colorless oil (0.8 g, 83%). $^1$H NMR (400 MHz, CDCl₃): δ 9.55 (t, J=4 Hz, 1H), 6.84 (s, 1H), 6.61 (s, 1H), 2.84 (d, J=4.0 Hz, 2H), 2.53 (s, 3H), 2.23 (s, 3H), 1.86-1.80 (m, 1H), 1.57 (s, 6H), 1.17-1.14 (m, 2H), 1.05-1.00 (m, 2H); $^{13}$C NMR (CDCl₃): 203.3, 174.1, 149.7, 137.9, 136.9, 132.8, 132.7, 123.5, 56.8, 38.3, 31.7, 25.5, 20.4, 13.6, 9.1.

Synthesis of 3-(2-((cyclopropanecarbonyl)oxy)-4,6-dimethylphenyl)-3-methylbutanoic acid (26)

To a solution of 3,5-dimethyl-2-(2-methyl-4-oxobutan-2-yl)phenyl cyclopropanecarboxylate (25, 200 mg, 0.73 mmol) in t-BuOH (4 mL) and 2-methylbut-2-ene (0.7 mL)NaClO₂ (98 mg, 1.08 mmol) in 0.67 M NaH₂PO₄ (0.8 mL) was added dropwise at room temperature. After 2 h, the reaction mixture was quenched with H₂O (10 mL), and extracted in ethyl acetate (2×50 ml). The combined organic phase was dried over Na₂SO₄ and then evaporated under reduced pressure to give the crude product, which was purified by column chromatography to yield a white solid (110 mg, 52%). $^1$H NMR (400 MHz, CDCl₃): δ 6.80 (s, 1H), 6.59 (s, 1H), 2.86 (s, 2H), 2.53 (s, 3H), 2.22 (s, 3H), 1.89-1.83 (m, 1H), 1.58 (s, 6H), 1.18-1.14 (m, 2H), 1.03-0.98 (m, 2H); $^{13}$C NMR (CDCl₃): 177.5, 174.2, 149.7, 138.1, 136.4, 133.5, 132.5, 123.2, 47.7, 38.9, 31.4, 25.4, 20.4, 13.6, 9.1.

Synthesis of Sodium 3-(2-((cyclopropanecarbonyl)oxy)-4,6-dimethylphenyl)-3-methylbutanethioate (HP-102)

To a solution of 3-(2-((cyclopropanecarbonyl)oxy)-4,6-dimethylphenyl)-3-methylbutanoic acid (26, 110 mg, 0.38 mmol) in dichloromethane (5 mL) was added Lawesson's reagent (77 mg, 0.19 mmol). The mixture was heated in a microwave at 100° C. for 6 min. A pure product was obtained using column chromatography (86 mg), which was then dissolved in 5 ml methanol and 2.5 ml of 0.1 M NaOH methanol solution at −78° C. After 5 min, the mixture was allowed to warm to room temperature and the solvent was removed by vacuum. The final product was achieved by recrystallization in ether as a white solid (70 mg, 56%). $^1$H NMR (400 MHz, CDCl₃): δ 6.79 (s, J=0.8 Hz, 1H), 6.48 (s, J=4 Hz, 1H), 3.56 (s, 2H), 2.58 (s, 3H), 2.20 (s, 3H), 2.02-1.96 (m, 1H), 1.54 (s, 6H), 1.11-1.05 (m, 4H); $^{13}$C NMR (CDCl₃): 176.5, 150.9, 139.5, 137.1, 136.3, 132.9, 123.8, 64.4, 40.7, 31.8, 25.7, 14.3, 9.4.

Example 4. Synthesis of sodium 3-(2-((cyclopropanecarbonyl)oxy)phenyl)-3-methylbutanethioate (HP-104)

Hydrogen sulfide precursor HP-104 was synthesized in 5 steps as shown in Scheme Scheme 9.

Scheme 9

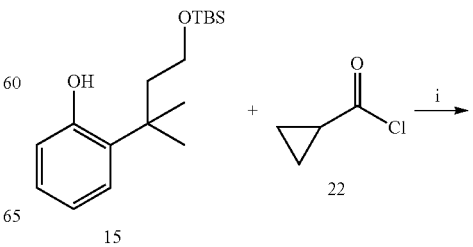

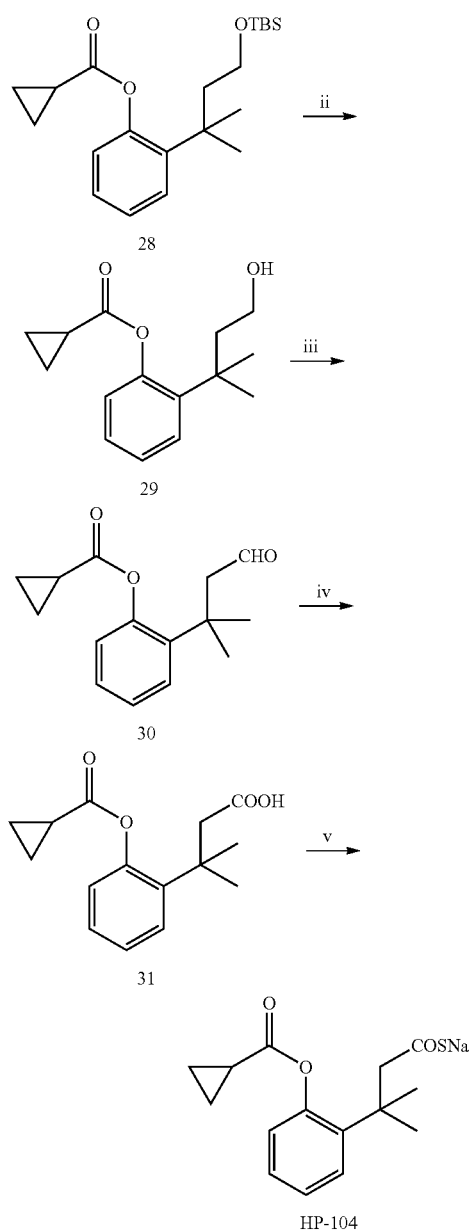

Reagents and conditions (i) Et$_3$N, DCM, 0° C.-rt, 12 h, 73%; (ii) AcOH/H$_2$O, THF, rt, 12 h, 85%; (iii) PCC, DCM, rt, 2 h 88%; (iv) NaClO$_2$/NaH$_2$PO$_4$, 2-methylbut-2-ene, t-BuOH, rt, 2 h 65%; (v) 1) Lawesson's Reagent, DCM, microwave, 6 min; 2) NaOH, methanol, -78° C., 65% for the last two steps.

Synthesis of 2-(4-((tert-butyldimethylsilyl)oxy)-2-methylbutan-2-yl)phenyl cyclopropanecarboxylate (28)

To a solution of 2-(4-((tert-butyldimethylsilyl)oxy)-2-methylbutan-2-yl)phenol (15, 2.0 g, 6.8 mmol) and Et$_3$N (1.4 g, 13.6 mmol) in DCM (150 mL) was added dropwise cyclopropanecarbonyl chloride (22, 1.46 g, 13.6 mmol) at 0° C. The mixture was allowed to warm to room temperature and stirred for 12 h. Then the reaction was quenched with the addition of H$_2$O (100 mL), and solution was extracted with ethyl acetate (2×150 mL). The combined organic phase was dried over anhydrous Na$_2$SO$_4$ and evaporated under reduced pressure to give the crude product, which was purified by column chromatography (hexane:ethyl acetate=50:1) to give a colorless oil (1.8 g, 73%). $^1$H NMR (CDCl$_3$): δ 7.32 (dd, J=7.6 Hz, 1.6 Hz, 1H), 7.23-7.19 (m, 1H), 7.16-7.12 (m, 1H), 6.98 (dd, J=7.6 Hz, 1.6 Hz, 1H), 3.41 (t, J=7.6 Hz, 2H), 2.03 (t, J=7.6 Hz, 2H), 1.92-1.85 (m, 1H), 1.38 (s, 6H), 1.19-1.18 (m, 2H), 1.05-1.00 (m, 2H), 0.84 (s, 9H), -0.04 (s, 6H). $^{13}$C NMR (CDCl$_3$) δ 173.5, 149.4, 139.1, 128.1, 127.1, 125.6, 124.2, 60.7, 44.5, 36.9, 29.2, 26.1, 18.3, 13.5, 9.1, -5.2. HRMS calcd for C$_{21}$H$_{34}$O$_3$Si [M+H]$^+$363.2350, found: 363.2348.

Synthesis of 2-(4-hydroxy-2-methylbutan-2-yl)phenyl cyclopropanecarboxylate (29)

To a solution of 2-(4-((tert-butyldimethylsilyl)oxy)-2-methylbutan-2-yl)phenyl cyclopropanecarboxylate (28, 1.7 g, 4.69 mmol) in THF (20 mL) was added H$_2$O (20 mL) and AcOH (60 mL). The reaction mixture was stirred at room temperature for 4 h, quenched with H$_2$O (50 mL), and extracted with ethyl acetate (2×150 mL). The combined organic phase was dried over anhydrous Na$_2$SO$_4$ and evaporated under reduced pressure, and purified silica gel column chromatography (hexane:ethyl acetate=10:1) as colorless oil (1.1 g, 95%). $^1$H NMR (400 MHz CDCl$_3$): δ 7.32 (dd, J=7.6 Hz, 1.6 Hz, 1H), 7.24-7.20 (m, 1H), 7.18-7.13 (m, 1H), 6.96 (dd, J=7.6 Hz, 1.6 Hz, 1H), 3.42 (t, J=7.6 Hz, 2H), 2.03 (t, J=7.6 Hz, 2H), 1.93-1.87 (m, 1H), 1.39 (s, 6H), 1.21-1.17 (m, 2H), 1.07-1.02 (m, 2H). $^{13}$C NMR (CDCl$_3$) δ 174.1, 149.4, 139.0, 128.1, 127.3, 125.9, 124.3, 60.3, 44.4, 36.9, 29.2, 13.6, 9.2. For C$_{15}$H$_{20}$O$_3$ [M+H]$^+$ 249.1485, found: 249.1485.

Synthesis of 2-(2-methyl-4-oxobutan-2-yl)phenyl cyclopropanecarboxylate (30)

To a solution of PCC (2.2 g, 10.0 mmol) in DCM (20 mL) was added dropwise 2-(4-hydroxy-2-methylbutan-2-yl)phenyl cyclopropanecarboxylate (29, 1.1 g, 4.4 mmol) in DCM (25 mL) at room temperature. After 2 h, the mixture was directly subjected to column chromatography (hexane:ethyl acetate=20:1) to obtain the pure product as colorless oil (0.95 g, 88%). $^1$H NMR (CDCl$_3$): δ 9.45 (t, J=2.8 Hz, 1H), 7.38 (dd, J=8.0 Hz, 1.6 Hz, 1H), 7.29-7.25 (m, 1H), 7.21-7.17 (m, 1H), 7.03 (dd, J=8.0 Hz, 1.6 Hz, 1H), 2.81 (d, J=2.8 Hz, 2H), 1.93-1.86 (m, 1H), 1.47 (s, 6H), 1.21-1.17 (m, 2H), 1.08-1.04 (m, 2H). $^{13}$C NMR (CDCl$_3$): δ 202.9, 173.4, 149.2, 137.6, 127.9, 127.7, 126.0, 124.5, 54.5, 36.3, 29.1, 13.5, 9.2. HRMS calcd for C$_{15}$H$_{18}$O$_3$ [M+Na]$^+$269.1148, found: 269.1149.

Synthesis of 3-(2-((cyclopropanecarbonyl)oxy)phenyl)-3-methylbutanoic acid (31)

To a solution of 2-(2-methyl-4-oxobutan-2-yl)phenyl cyclopropanecarboxylate (30, 900 mg, 3.6 mmol) in t-BuOH (20 mL) and 2-methylbut-2-ene (4 mL)NaClO$_2$ (496 mg, 5.4 mmol) in 0.67 M NaH$_2$PO$_4$ (4 mL) was added dropwise at room temperature. After 2 h, the reaction mixture was quenched with H$_2$O (20 mL), and extracted with ethyl acetate (2×100 ml). The combined organic phase was dried over anhydrous Na$_2$SO$_4$ and then evaporated under reduced pressure to give the crude product, which was purified by column chromatography (hexane:ethyl acetate=10:1) to yield a white solid (610 mg, 65%). $^1$H NMR (MeOH): δ 7.42 (dd, J=7.6 Hz, 1.6 Hz, 1H), 7.23-7.14 (m, 2H), 6.97 (dd, J=7.6 Hz, 1.6 Hz, 1H), 2.80 (s, 2H), 1.99-1.93 (m, 1H), 1.47 (s, 6H), 1.13-1.07 (m, 4H). $^{13}$C NMR (CDCl$_3$) δ 177.6, 173.6, 149.1, 138.2, 127.8, 127.5, 125.8, 124.1, 45.8, 36.7, 28.4, 13.5, 9.2. HRMS calcd for C$_{15}$H$_{18}$O$_4$ [M+H]$^+$ 263.1278, found: 263.1279.

Synthesis of sodium 3-(2-((cyclopropanecarbonyl)oxy)phenyl)-3-methylbutanethioate (HP-104)

To a solution of 3-(2-((cyclopropanecarbonyl)oxy)phenyl)-3-methylbutanoic acid (31, 120 mg, 0.46 mmol) in DCM (5 mL) was added Lawesson's reagent (92 mg, 0.23 mmol). The mixture was heated in a microwave at 100° C. for 6 min. The mixture was directly subjected to column chromatography (hexane:ethyl acetate=20:1) to obtain the pure product as colorless oil, which was then dissolved in 5 ml methanol. Then 2.5 ml of 0.1 M NaOH methanol solution was added to the reaction solution at −78° C. After 5 min, the mixture was allowed to warm to room temperature and the solvent was removed by vacuum. The final product was achieved by recrystallization in ether as a white solid (90 mg, 65%). $^1$H NMR (CDCl$_3$): δ 7.38 (d, J=7.2 Hz, 1H), 7.28-7.17 (m, 2H), 7.04 (d, J=8.0 Hz, 1H), 4.41 (s, 1H), 3.11 (s, 2H), 1.97-1.90 (m, 1H), 1.48 (s, 6H), 1.22-1.20 (m, 2H), 1.09-1.06 (m, 2H); $^{13}$C NMR (CDCl$_3$): 195.8, 173.4, 149.1, 137.6, 128.0, 127.7, 125.9, 124.2, 56.3, 37.5, 28.4, 13.5, 9.3. HRMS calcd for C$_{15}$H$_{17}$NaO$_3$S [M+H]$^+$ 301.0869, found: 301.0871.

Example 5: (S)-Ibuprofen Hybrid H$_2$S Precursor (HP-106)

Hydrogen sulfide-ibuprofen hybrid precursor (HP-106) was synthesized in 6 steps, as shown in Scheme 10.

Scheme 10

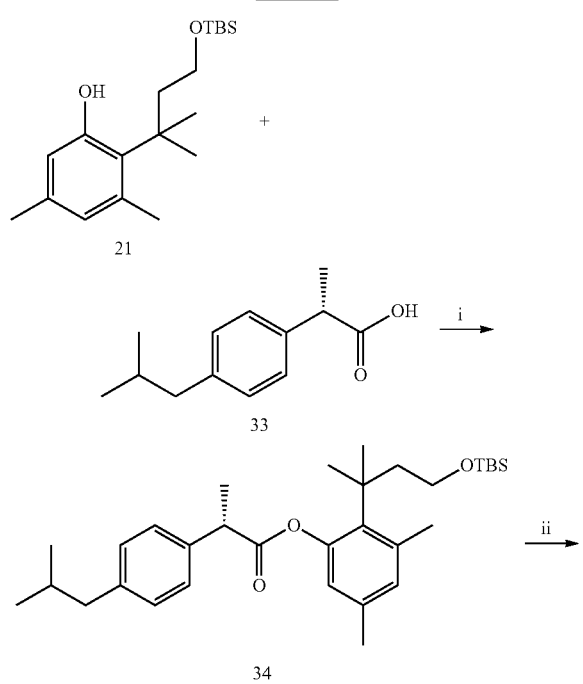

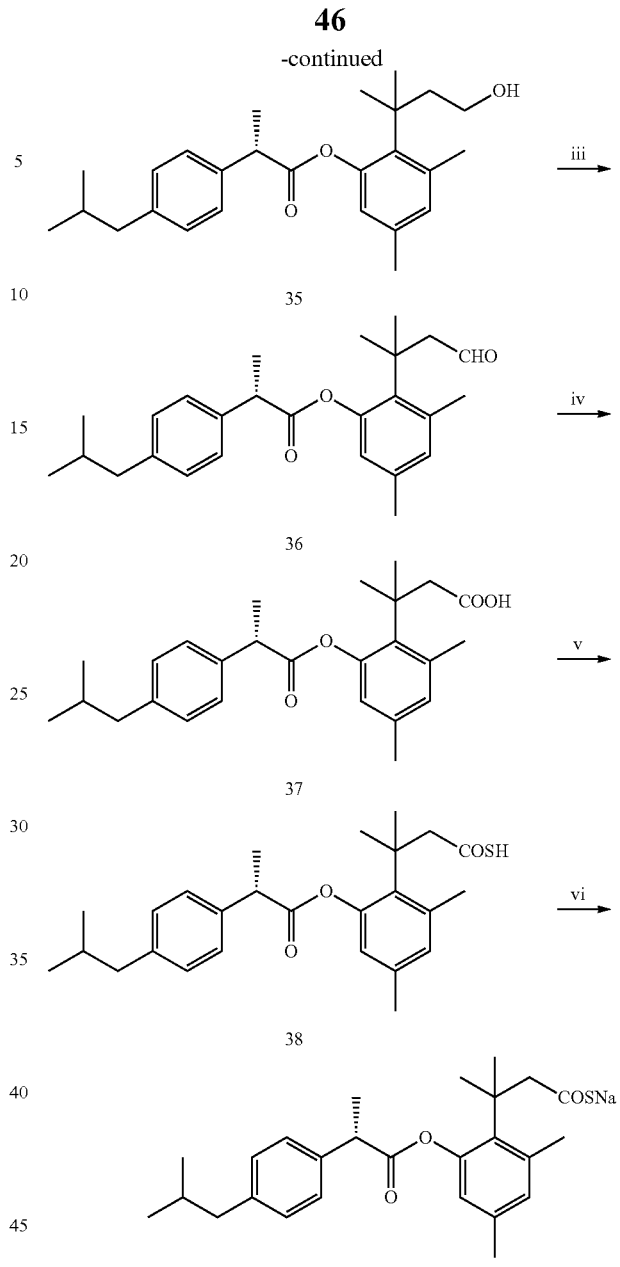

HP-106

Reagents and conditions (i) EDC/DMAP, DCM, rt, 2 h; (ii) AcOH/H$_2$O, THF, rt, 12 h; (iii) PCC, DCM, rt, 2 h; (iv) NaClO$_2$/NaH$_2$PO$_4$, 2-methylbut-2-ene, t-BuOH, rt, 2 h; (v) Lawesson's Reagent, DCM, microwave, 6 min; (vi) NaOH, methanol, -78° C.

Synthesis of (S)-2-O-((tert-Butyldimethylsilyl)oxy)-2-methylpropan-2-yl)-3,5-dimethylphenyl 2-(4-isobutylphenyl)propanoate (34)

To a solution of 2-(4-((tert-butyldimethylsilyl)oxy)-2-methylbutan-2-yl)-3,5-dimethylphenol (21, 1.06 g, 3.3 mmol), (S)-2-(4-isobutylphenyl)propanoic acid (33, 618 mg, 3 mmol) and DMAP (73 mg, 0.6 mmol) in dichloromethane (10 mL) was added EDC (1.15 g, 6 mmol). The mixture was stirred at room temperature for 2 h, then quenched with the addition of H$_2$O (10 mL), and extracted with ethyl acetate (2×50 mL). The combined organic phase was dried over Na$_2$SO$_4$ and evaporated under reduced pressure to give the crude product, which was purified by chromatography to obtain a colorless oil (1.45 g, 95%). $^1$H NMR (400 MHz CDCl$_3$): δ 7.32 (d, J=8.0 Hz, 2H), 7.15 (d, J=8.0 Hz, 2H), 6.77 (s, 1H), 6.35 (m, 1H), 3.90 (q, J=7.2 Hz, 1H), 3.44 (t, J=7.2 Hz, 2H), 2.50-2.48 (m, 5H), 2.18 (s, 3H), 1.95-1.85 (m, 3H), 1.62 (d, J=7.2 Hz, 3H), 1.37-1.35 (m, 6H), 0.93 (d, J=6.8 Hz, 6H), 0.86 (s, 9H), 0.02 (s, 6H); $^{13}$C NMR (CDCl$_3$): 173.7, 150.3, 140.9, 138.3, 137.0, 135.9, 134.3, 132.3, 129.6, 127.7, 122.7, 60.9, 46.0, 45.9, 45.2, 39.2, 31.9, 31.9, 30.4, 26.1, 25.4, 22.5, 20.3, 18.4, 18.4, −5.2.

Synthesis of (S)-2-(4-Hydroxy-2-methylbutan-2-yl)-3, 5-dimethylphenyl 2-(4-isobutylphenyl)propanoate (35)

To a solution of (S)-2-(1-((tert-butyldimethylsilyl)oxy)-2-methylpropan-2-yl)-3, 5-dimethylphenyl2-(4-isobutylphenyl)propanoate (34, 850 mg, 1.67 mmol) in tetrahydrofuran (3 mL) was added H$_2$O (3 mL) and AcOH (9 mL). The reaction mixture was stirred at room temperature for 12 h, quenched with H$_2$O (10 mL), and extracted in ethyl acetate (2×50 mL). The combined organic phase was dried over Na$_2$SO$_4$ and evaporated under reduced pressure, and purified using silica gel column chromatography as a colorless oil (590 mg, 90%). $^1$H NMR (400 MHz CDCl$_3$): 7.31 (d, J=8.0 Hz, 2H), 7.16 (d, J=8.0 Hz, 2H), 6.78 (s, 1H), 6.35-6.34 (m, 1H), 3.91 (q, J=7.2 Hz, 1H), 3.44 (t, J=7.2 Hz, 2H), 2.49-2.48 (m, 5H), 2.18 (s, 3H), 1.89-1.64 (m, 3H), 1.63 (d, J=7.2 Hz, 3H), 1.36 (s, 6H), 0.92 (d, J=6.8 Hz, 6H); $^{13}$C NMR (CDCl$_3$): 174.3, 150.3, 141.1, 138.4, 136.7, 136.2, 134.0, 132.4, 129.6, 127.7, 122.8, 60.6, 46.0, 45.7, 45.2, 39.2, 32.0, 30.3, 26.0, 22.5, 20.2, 18.3.

Synthesis of (S)-3,5-Dimethyl-2-(2-methyl-4-oxobutan-2-yl)phenyl 2-(4-isobutylphenyl)propanoate (36)

To a solution of PCC (591 mg, 2.75 mmol) in dichloromethane (5 mL) was dropwise added (S)-2-(4-hydroxy-2-methylbutan-2-yl)-3,5-dimethylphenyl2-(4-isobutylphenyl)propanoate (35, 545 mg, 1.38 mmol) in dichloromethane (5 mL) at room temperature. After 2 h, the pure product was achieved by chromatography as colorless oil (515 mg, 94%). $^1$H NMR (400 MHz, CDCl$_3$): δ 9.40 (d, J=2.8 Hz, 1H), 7.30 (d, J=8.0 Hz, 2H), 7.16 (d, J=8.0 Hz, 2H), 6.80 (s, 1H), 6.44 (s, 1H), 3.91 (q, J=7.2 Hz, 1H), 2.57-2.55 (m, 2H), 2.50-2.45 (m, 5H), 1.91-1.84 (m, 3H), 1.64-1.62 (m, J=6.4 Hz, 3H), 1.63 (d, J=7.2 Hz, 3H), 1.42 (s, 3H), 1.36 (s, 3H), 0.92 (d, J=6.4 Hz, 6H). $^{13}$C NMR (CDCl$_3$): δ 203.2, 173.5, 150.0, 141.2, 137.8, 136.8, 136.4, 132.9, 132.6, 129.7, 127.7, 123.0, 56.5, 45.99, 45.1, 38.2, 31.6, 31.5, 30.3, 25.6, 22.4, 20.3, 18.2.

Synthesis of 3-(2-(((S)-2-(4-Isobutylphenyl)propanoyl)oxy)-4, 6-dimethyl phenyl)butanoic acid (37)

To a solution of (S)-3,5-dimethyl-2-(2-methyl-4-oxobutan-2-yl)phenyl2-(4-isobutylphenyl)propanoate (36, 570 mg, 1.44 mmol) in t-BuOH (8 mL) and 2-methylbut-2-ene (2.5 mL) was added dropwise NaClO$_2$ (298 mg, 3.31 mmol) in 0.67M NaH$_2$PO$_4$ (1.2 mL) at room temperature. After 2 h, the reaction mixture was quenched with H$_2$O (20 mL), and extracted in ethyl acetate (2×50 ml). The combined organic phase was dried over Na$_2$SO$_4$ and then evaporated under reduced pressure to give the crude product, which was purified by column chromatography to yield a white solid (480 mg, 81%). $^1$H NMR (400 MHz, CDCl$_3$): δ 7.30 (d, J=8.0 Hz, 2H), 7.14 (d, J=8.0 Hz, 2H), 6.76 (s, 1H), 6.39 (s, 1H), 3.92 (q, J=6.8 Hz, 1H), 2.68-2.54 (m, 2H), 2.50-2.46 (m, 5H), 2.17 (s, 3H), 1.89-1.83 (m, J=6.4 Hz, 1H), 1.62 (d, J=6.8 Hz, 3H), 1.44 (s, 3H), 1.38 (s, 3H), 0.90 (d, J=6.4 Hz, 6H); $^{13}$C NMR (CDCl$_3$): δ 176.8, 173.8, 150.1, 141.1, 138.1, 136.6, 136.3, 133.4, 132.5, 129.7, 127.7, 122.7, 47.2, 46.0, 45.2, 38.8, 31.4, 31.3, 30.4, 25.5, 22.5, 20.4, 18.3.

Synthesis of 3-(2-(((S)-2-(4-Isobutylphenyl)propanoyl)oxy)-4,6-dimethylphenyl)butanethioic S-acid (38)

To a solution of 3-(2-(((S)-2-(4-isobutylphenyl)propanoyl)oxy)-4,6-dimethylphenyl)butanoic acid (37, 190 mg, 0.46 mmol) in dichloromethane (5 mL) was added Lawesson's reagent (92 mg). The mixture was subjected to the following microwave condition: Temperature: 100° C., reaction time 6 min. A pure product was obtained after column chromatography (150 mg, 79%). $^1$H NMR (400 MHz, CDCl$_3$): δ 7.33 (d, J=8.0 Hz, 2H), 7.18 (d, J=8.0 Hz, 2H), 6.77 (s, 1H), 6.49 (m, 1H), 4.27 (s, 1H), 3.96 (q, J=7.2 Hz, 1H), 2.86-2.71 (m, 2H), 2.51-2.49 (m, 5H), 2.20 (s, 3H), 1.92-1.83 (m, J=6.4 Hz, 1H), 1.66 (d, J=7.2 Hz, 3H), 1.41 (s, 3H), 1.32 (s, 3H), 0.93 (d, J=6.4 Hz, 6H). $^{13}$C NMR (CDCl$_3$): δ 196.2, 173.4, 150.1, 141.3, 138.1, 136.5, 136.4, 132.8, 132.5, 129.8, 127.8, 122.8, 58.3, 46.1, 45.2, 39.7, 31.6, 31.4, 30.4, 25.7, 22.5, 20.4, 18.2.

Synthesis of Sodium(S)-3-(2-((2-(4-isobutylphenyl)propanoyl)oxy)-4,6-dimethylphenyl)-3-methylbutanethioate (HP-106)

To a solution of 3-(2-(((S)-2-(4-isobutylphenyl)propanoyl)oxy)-4,6-dimethylphenyl)butanethioic S-acid (38) in methanol was added 0.1 M NaOH methanol solution at −78° C. After 5 min, the mixture was allowed to warm to room temperature and the solvent was removed by vacuum. The final product was achieved by recrystallization in ether as white solid. $^1$H NMR (400 MHz, CD$_3$OD): δ 7.35 (d, J=8.1 Hz, 2H), 7.17 (d, J=8.1 Hz, 2H), 6.74 (s, 1H), 6.23 (s, 1H), 4.08 (q, J=7.1 Hz, 1H), 3.21 (m, 2H), 2.53 (s, 3H), 2.48 (m, 2H), 2.12 (s, 3H), 1.87 (m, 1H), 1.58 (d, J=7.1 Hz, 3H), 1.43 (s, 3H), 1.38 (s, 3H), 0.91 (d, J=6.6 Hz, 6H). $^{13}$C NMR (CD$_3$OD): δ 176.0, 151.1, 142.0, 139.4, 138.6, 137.1, 136.3, 132.8, 130.5, 128.7, 123.2, 64.4, 48.4, 46.9, 46.1, 40.6, 31.7, 31.5, 25.7, 22.7, 20.1, 18.7.

Example 6: (5)-Naproxen Hybrid H$_2$S Precursor (HP-105)

Hydrogen sulfide-naproxen hybrid precursor HP-105 was synthesized in 5 steps, as shown in Scheme 11.

Scheme 11

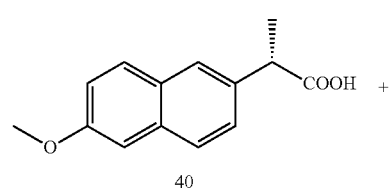

40

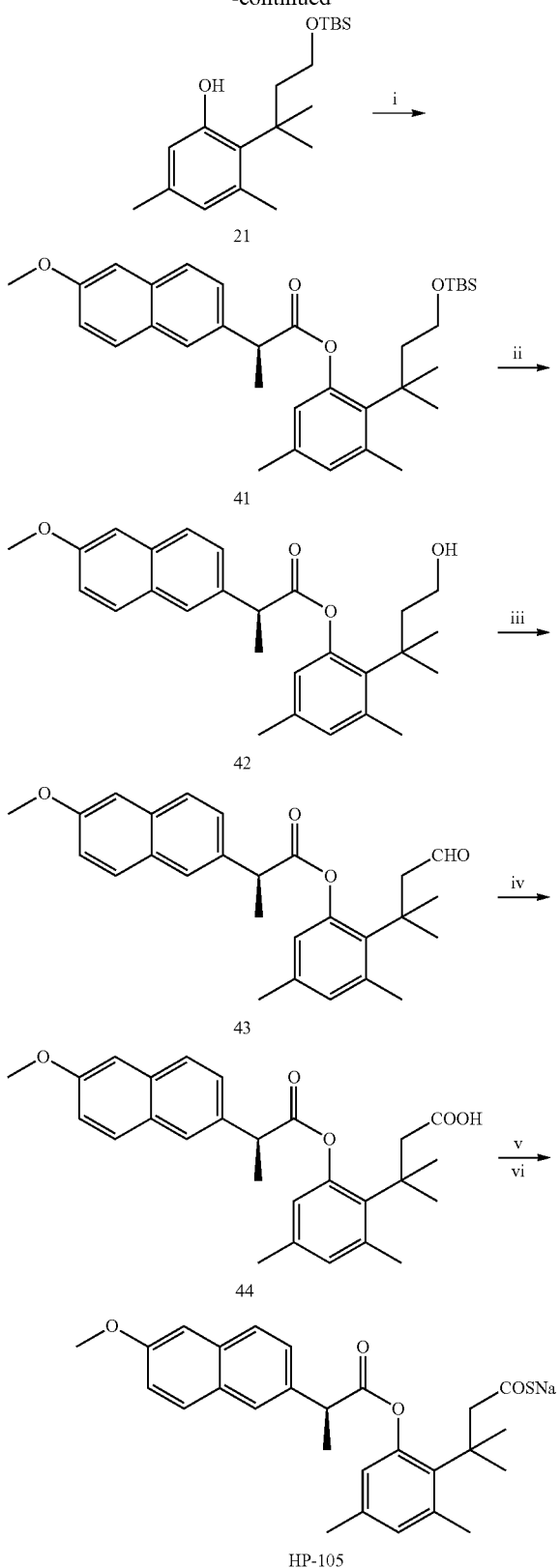

Reagents and conditions (i) EDC/DMAP, DCM, rt, 2 h; (ii) AcOH/H₂O, THF, rt, 12 h; (iii) PCC, DCM, rt, 2 h; (iv) NaClO₂/NaH₂PO₄, 2-methylbut-2-ene, t-BuOH, rt, 2 h; (v) Lawesson's Reagent, DCM, microwave, 6 min; (vi) NaOH, methanol, -78° C.

Synthesis of 2-(4-((tert-butyldimethylsilyl)oxy)-2-methylbutan-2-yl)-3,5-dimethylphenyl (S)-2-(6-methoxynaphthalen-2-yl)propanoate (41)

To a solution of 2-(4-((tert-butyldimethylsilyl)oxy)-2-methylbutan-2-yl)-3,5-dimethylphenol (21, 1.27 g, 3.9 mmol), (S)-2-(6-methoxynaphthalen-2-yl)propanoic acid (1.00 g, 4.4 mmol) and DMAP (100 mg, 0.8 mmol) in dichloromethane (50 mL) was added EDC (1.62 g, 8.7 mmol). The mixture was stirred at room temperature for 2 h, then quenched with the addition of H₂O (50 mL), and extracted with dichloromethane (2×50 mL). The combined organic phase was dried over Na₂SO₄ and evaporated under reduced pressure to give the crude product, which was purified by chromatography to give a colorless oil (1.86 g, 88%). $^1$H NMR (400 MHz CDCl₃): δ 7.80-7.74 (m, 3H), 7.53 (dd, J=8.4 Hz, J=1.6 Hz, 1H), 7.20-7.16 (m, 2H), 6.77 (d, J=1.2 Hz, 1H), 6.36 (d, J=1.2 Hz, 1H), 4.07 (q, J=7.2 Hz, 1H), 3.93 (s, 3H), 3.43 (t, J=7.2 Hz, 2H), 2.50 (s, 3H), 2.17 (s, 3H), 1.94 (t, J=7.2 Hz, 2H), 1.72 (d, J=7.2 Hz, 3H), 1.39 (d, J=7.2 Hz, 6H), 0.87 (s, 9H), −0.02 (s, 6H); $^{13}$C NMR (CDCl₃): 173.7, 157.8, 150.2, 138.3, 136.0, 134.9, 134.2, 134.0, 132.3, 129.5, 129.1, 127.4, 126.6, 126.5, 122.7, 119.2, 105.7, 60.9, 55.4, 46.3, 45.9, 39.2, 31.9, 31.9, 26.1, 25.4, 20.3, 18.6, 18.3, −5.2.

Synthesis of 2-(4-hydroxy-2-methylbutan-2-yl)-3,5-dimethylphenyl (S)-2-(6-methoxynaphthalen-2-yl)propanoate (42)

To a solution of (2-(4-((tert-butyldimethylsilyl)oxy)-2-methylbutan-2-yl)-3,5-dimethylphenyl (S)-2-(6-methoxynaphthalen-2-yl)propanoate (41, 1.86 g, 3.5 mmol) in tetrahydrofuran (15 mL) was added H₂O (20 mL) and AcOH (45 mL). The reaction mixture was stirred at room temperature for 12 h, quenched with H₂O (50 mL), and extracted with ethyl acetate (2×100 mL). The combined organic phase was dried over Na₂SO₄ and evaporated under reduced pressure. Silica gel column chromatography gave the product as colorless oil (1.27 g, 87%). $^1$H NMR (400 MHz CDCl₃): δ 7.79-7.74 (m, 3H), 7.52 (dd, J=8.4 Hz, J=1.6 Hz, 1H), 7.19-7.15 (m, 2H), 6.77 (d, J=1.2 Hz, 1H), 6.35 (d, J=1.2 Hz, 1H), 4.08 (q, J=7.2 Hz, 1H), 3.93 (s, 3H), 3.44 (t, J=7.2 Hz, 2H), 2.49 (s, 3H), 2.16 (s, 3H), 1.92-1.80 (m, 2H), 1.72 (d, J=7.2 Hz, 3H), 1.37 (s, 6H); 13C NMR (CDCl3): 174.2, 157.9, 150.2, 138.4, 136.3, 134.6, 134.0, 134.0, 132.5, 129.4, 129.1, 127.5, 126.7, 126.5, 122.8, 119.3, 105.7, 60.6, 55.4, 46.3, 45.6, 39.2, 32.0, 25.5, 20.2, 18.5.

Synthesis of 3,5-dimethyl-2-(2-methyl-4-oxobutan-2-yl)phenyl (S)-2-(6-methoxynaphthalen-2-yl)propanoate (43)

To a solution of PCC (1.2 g, 5.6 mmol) in dichloromethane (15 mL), 2-(4-hydroxy-2-methylbutan-2-yl)-3,5-dimethylphenyl (S)-2-(6-methoxynaphthalen-2-yl)propanoate (42, 1.2 g, 2.8 mmol) in dichloromethane (20 mL) was added dropwise at room temperature. After 2 h, the pure product was achieved by chromatography as colorless oil (0.97 g, 81%). $^1$H NMR (400 MHz, CDCl₃): δ 9.36 (d, J=2.4 Hz, 1H), 7.77-7.73 (m, 3H), 7.49 (dd, J=8.8 Hz, J=1.6 Hz, 1H), 7.19-7.14 (m, 2H), 6.79 (s, 1H), 6.43 (s, 1H), 4.06 (q, J=7.2 Hz, 1H), 3.93 (s, 3H), 2.54 (t, J=2.4 Hz, 2H), 2.48 (s, 3H), 2.18 (s, 3H), 1.71 (d, J=7.2 Hz, 3H), 1.40 (s, 3H), 1.35 (s, 3H); 13C NMR (CDCl3): 201.2, 173.5, 157.9, 149.9, 137.8, 136.9, 134.3, 134.0, 132.9, 132.7, 129.4, 129.1, 127.6, 126.7, 126.4, 123.0, 119.4, 105.7, 56.4, 55.4, 46.3, 38.2, 31.6, 31.4, 25.6, 20.3, 18.4.

Synthesis of (S)-3-(2-((2-(6-methoxynaphthalen-2-yl)propanoyl)oxy)-4,6-dimethylphenyl)-3-methylbutanoic acid (44)

To a solution of 3,5-dimethyl-2-(2-methyl-4-oxobutan-2-yl)phenyl (S)-2-(6-methoxynaphthalen-2-yl)propanoate (43, 0.96 g, 2.3 mmol) in t-BuOH (18 mL) and 2-methylbut-2-ene (3 mL) was added dropwise NaClO$_2$ (330 mg, 3.4 mmol) in 0.67M NaH$_2$PO$_4$ (3.6 mL) at room temperature. After 2 h, the reaction mixture was quenched with H$_2$O (20 mL), and extracted with ethyl acetate (2×50 ml). The combined organic phase was dried over Na$_2$SO$_4$ and then evaporated under reduced pressure to give the crude product, which was purified by column chromatography to yield a white solid (650 mg, 66%). $^1$H NMR (400 MHz, CDCl$_3$): δ7.77-7.71 (m, 3H), 7.50 (dd, J=8.8 Hz, J=2.0 Hz, 1H), 7.17-7.13 (m, 2H), 6.75 (s, 1H), 6.40 (s, 1H), 4.09 (q, J=7.2 Hz, 1H), 3.92 (s, 3H), 2.68-2.55 (m, 2H), 2.49 (s, 3H), 2.15 (s, 3H), 1.70 (d, J=7.2 Hz, 3H), 1.44 (s, 3H), 1.38 (s, 3H); 13C NMR (CDCl3): 176.8, 173.7, 157.9, 150.0, 138.1, 136.4, 134.5, 134.0, 133.5, 132.5, 129.5, 129.1, 127.5, 126.7, 126.5, 122.7, 119.2, 105.7, 55.4, 47.2, 46.3, 38.8, 31.4, 31.2, 25.5, 20.3, 18.4.

Synthesis of Sodium (S)-3-(2-((2-(6-methoxynaphthalen-2-yl)propanoyl)oxy)-4,6-dimethylphenyl)-3-methylbutanethioate (HP-105)

To a solution of (S)-3-(2-((2-(6-methoxynaphthalen-2-yl)propanoyl)oxy)-4,6-dimethylphenyl)-3-methylbutanoic acid (44, 180 mg, 0.41 mmol) in dichloromethane (5 mL) was added Lawesson's reagent (83 mg). The mixture was subjected to the following microwave condition: Temperature: 100° C., reaction time 6 min. A pure product was obtained after column chromatography, which was then dissolved in 5 ml methanol and 2.6 ml 0.1 M NaOH methanol solution was added at −78° C. After 5 min, the mixture was allowed to warm to room temperature and the solvent was removed by vacuum. The final product was achieved by recrystallization in ether as white solid (140 mg, 72%)$^1$H NMR (400 MHz, CDCl$_3$): δ 7.83-7.75 (m, 3H), 7.53 (dd, J=8.8 Hz, J=2.0 Hz, 1H), 7.22 (d, 2 Hz, 1H), 7.12 (dd, J=8.8 Hz, J=2.0 Hz, 1H), 6.71 (s, 1H), 6.21 (s, 1H), 4.26 (q, J=7.2 Hz, 1H), 3.90 (s, 3H), 3.31 (m, 2H), 2.52 (s, 3H), 2.08 (s, 3H), 1.66 (d, J=7.2 Hz, 3H), 1.44 (s, 3H), 1.40 (s, 3H); 13C NMR (CDCl3): 176.0, 159.2, 151.1, 139.4, 137.1, 136.3, 136.3, 135.4, 132.9, 130.5, 130.3, 128.4, 127.6, 127.4, 123.2, 120.0, 106.6, 64.5, 55.7, 47.1, 40.6, 31.7, 25.7, 20.1, 18.7.

Example 7: Sulindac Hybrid H$_2$S Precursor (HP-107)

Hydrogen sulfide-sulindac hybrid precursor HP-107 was synthesized in 6 steps, as shown in Scheme 12.

Synthesis of 2-(4-((tert-butyldimethylsilyl)oxy)-2-methylbutan-2-yl)-3,5-dimethylphenyl-2-(5-fluoro-2-methyl-1-(4-(methylsulfinyl)benzylidene)-1H-inden-3-yl)acetate (47)

To a solution of 2-(4-((tert-butyldimethylsilyl)oxy)-2-methylbutan-2-yl)-3,5-dimethylphenol (21, 1.27 g, 3.9 mmol), 2-(5-fluoro-2-methyl-1-(4-(methylsulfinyl) benzylidene)-1H-inden-3-yl) acetic acid (46, 2.00 g, 5.6 mmol) and DMAP (105 mg, 0.84 mmol) in dichloromethane (50 mL) was added EDC (2.09 g, 11.2 mmol). The mixture was stirred at room temperature for 2 h, then quenched with the addition of H$_2$O (50 mL), and extracted with dichloromethane (2×50 mL). The combined organic phase was dried over Na$_2$SO$_4$ and evaporated under reduced pressure to give the crude product, which was purified by chromatography to give a yellow oil (2.05 g, 83%). $^1$H NMR (400 MHz, CDCl$_3$): δ 7.67-7.74 (m, 4H), 7.21-7.14 (m, 2H), 7.01-6.91 (m, 2H), 6.79 (s, 1H), 6.56-6.60 (m, 1H), 6.47 (s, 1H), 3.77 (s, 2H), 3.43 (t, J=7.4 Hz, 2H), 2.81 (s, 3H), 2.50 (s, 3H), 2.27 (s, 3H), 2.20 (s, 3H), 1.97 (t, J=7.4 Hz, 2H), 1.43 (s, 6H), 0.82 (s, 9H), −0.05 (s, 6H); $^{13}$C NMR (CDCl$_3$): 169.1, 163.4 (d, $^1J_{CF}$=246 Hz), 149.8, 146.8, 146.7, 145.6, 141.7, 139.6, 138.7, 138.5, 136.0, 134.0, 132.5, 131.2, 130.3, 129.5, 128.4, 123.8, 123.8, 123.7, 122.8, 110.9 (d, $^2J_{CF}$=23 Hz), 106.2 (d, $^2J_{CF}$=23 Hz), 60.7, 45.9, 43.9, 39.1, 32.6, 31.8, 26.0, 25.3, 20.2, 18.2, 10.8, −5.4.

2-(4-hydroxy-2-methylbutan-2-yl)-3,5-dimethylphenyl-2-(5-fluoro-2-methyl-1-(4-(methylsulfinyl)benzylidene)-1H-inden-3-yl)acetate (48)

To a solution of 2-(4-((tert-butyldimethylsilyl)oxy)-2-methylbutan-2-yl)-3,5-dimethylphenyl-2-(5-fluoro-2-methyl-1-(4-(methylsulfinyl)benzylidene)-1H-inden-3-yl) acetate (47, 2.05 g, 3.10 mmol) in tetrahydrofuran (15 mL) was added H$_2$O (20 mL) and AcOH (45 mL). The reaction mixture was stirred at room temperature for 12 h, quenched with H$_2$O (50 mL), and extracted with ethyl acetate (2×100 mL). The combined organic phase was dried over Na$_2$SO$_4$ and evaporated under reduced pressure. Silica gel column chromatography gave the product as yellow oil (1.49 g, 88%) $^1$H NMR (400 MHz, CDCl3): δ 7.67-7.74 (m, 4H), 7.17-7.20 (m, 2H), 6.98 (dd, J=8.8, 2.3 Hz, 1H), 6.80 (s, 1H), 6.59 (td, J=8.9, 2.3 Hz, 1H), 6.48 (s, 1H), 3.80 (s, 2H), 3.45 (t, J=7.3 Hz, 2H), 2.80 (s, 3H), 2.50 (s, 3H), 2.27 (s, 3H), 2.20 (s, 3H), 1.96 (t, J=7.3 Hz, 2H), 1.44 (s, 6H); $^{13}$C NMR (CDCl$_3$): 169.6, 163.4 (d, $^1J_{CF}$=245 Hz), 149.8, 146.7, 146.6, 145.6, 141.6, 139.6, 138.8, 138.5, 136.3, 133.8, 132.6, 131.0, 130.3, 129.5, 128.6, 123.9, 123.8, 123.7, 122.9, 111.0 (d, $^2J_{CF}$=23 Hz), 106.2 (d, $^2J_{CF}$=22 Hz), 60.4, 45.6, 43.9, 39.1, 32.6, 31.9, 25.4, 20.2, 10.8.

3,5-dimethyl-2-(2-methyl-4-oxobutan-2-yl)phenyl-2-(5-fluoro-2-methyl-1-(4-(methylsulfinyl)benzylidene)-1H-inden-3-yl)acetate (49). To a solution of PCC (1.1 g, 5.4 mmol) in dichloromethane (15 mL), 2-(4-hydroxy-2-methylbutan-2-yl)-3,5-dimethylphenyl-2-(5-fluoro-2-methyl-1-(4-(methylsulfinyl)benzylidene)-1H-inden-3-yl)acetate (48, 1.49 g, 2.7 mmol) in dichloromethane (20 mL) was added dropwise, at room temperature. After 2 h, the pure product was achieved by chromatography as yellow oil (1.17 g, 80%). $^1$H NMR (400 MHz, CDCl$_3$) δ 9.41 (t, J=2.5 Hz, 1H), 7.68-7.74 (m, 4H), 7.17-7.20 (m, 2H), 6.97 (dd, J=8.8, 2.1 Hz, 1H), 6.83 (s, 1H), 6.63-6.53 (m, 2H), 3.80 (s, 2H), 2.81 (s, 3H), 2.68 (d, J=2.5 Hz, 2H), 2.51 (s, 3H), 2.27 (s, 3H), 2.22 (s, 3H), 1.47 (s, 6H).

Scheme 12

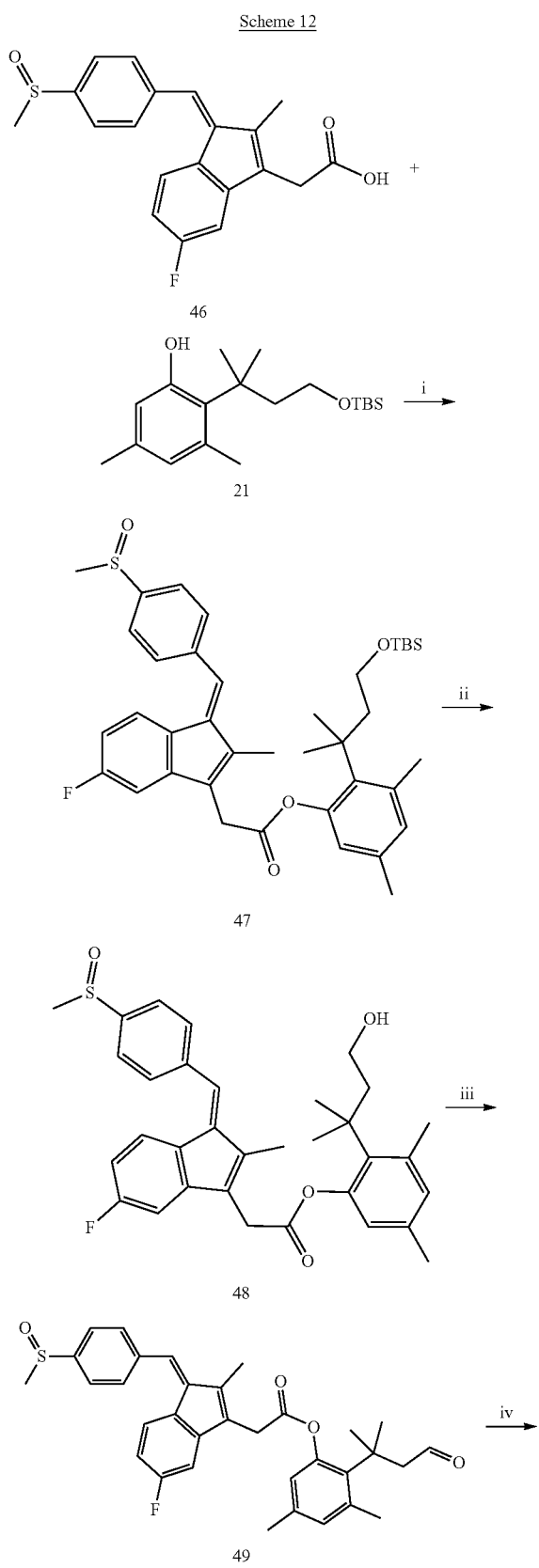

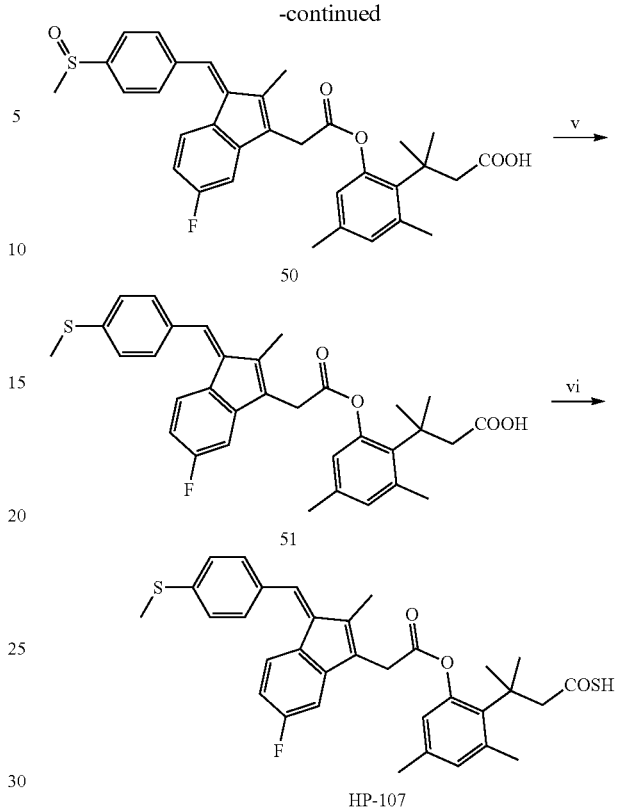

Reagents and conditions (i) EDC/DMAP, DCM, rt, 2 h; (ii) AcOH/H₂O, THF, rt, 12 h; (iii) PCC, DCM, rt, 2 h; (iv) NaClO₂/NaH₂PO₄, 2-methylbut-2-ene, t-BuOH, rt, 2 h; (v) Lawesson's Reagent, DCM, rt, 30 min; (vi) Lawesson's Reagent, DCM, microwave, 6 min;

Synthesis of 3-(2-(2-(5-fluoro-2-methyl-1-(4-(methylsulfinyl)benzylidene)-1H-inden-3-yl)acetoxy)-4,6-dimethylphenyl)-3-methylbutanoic acid (50)

To a solution of 3,5-dimethyl-2-(2-methyl-4-oxobutan-2-yl)phenyl-2-(5-fluoro-2-methyl-1-(4-(methylsulfinyl)benzylidene)-1H-inden-3-yl)acetate (49, 1.17 g, 2.15 mmol) in t-BuOH (18 mL) and 2-methylbut-2-ene (3 mL) was added dropwise NaClO₂ (350 mg, 3.4 mmol) in 0.67M NaH₂PO₄ (3.5 mL) at room temperature. After 2 h, the reaction mixture was quenched with H₂O (20 mL), and extracted with ethyl acetate (2×50 ml). The combined organic phase was dried over Na₂SO₄ and then evaporated under reduced pressure to give the crude product, which was purified by column chromatography to yield a yellow solid (831 mg, 69%). 1H NMR (400 MHz, CDCl₃): δ 7.65-7.72 (m, 4H), 7.15-7.18 (m, 2H), 6.97 (dd, J=8.8, 2.3 Hz, 1H), 6.78 (s, 1H), 6.71-6.70 (m, 1H), 6.56 (td, J=8.9, 2.3 Hz, 1H), 6.52 (s, 1H), 3.80 (s, 2H), 2.80 (s, 3H), 2.74 (s, 2H), 2.51 (s, 3H), 2.25 (s, 3H), 2.18 (s, 3H), 1.51 (s, 6H); ¹³C NMR (CDCl₃): 174.81, 169.11, 164.41 (d, $^1J_{CF}$=245 Hz), 149.6, 146.7, 146.6, 145.5, 141.6, 139.6, 138.9, 138.2, 136.4, 133.2, 132.6, 130.9, 130.3, 129.5-128.5, 123.9, 123.8, 123.7, 122.8, 111.0 (d, $^2J_{CF}$=22 Hz), 106.2 (d, $^2J_{CF}$=23.7 Hz), 46.8, 43.9, 38.7, 32.6, 31.3, 25.4, 20.3, 10.7.

Synthesis of 3-(2-(2-(5-fluoro-2-methyl-1-(4-(methylthio)benzylidene)-1H-inden-3-yl)acetoxy)-4,6-dimethylphenyl)-3-methylbutanoic acid (51)

To a solution of 3-(2-(2-(5-fluoro-2-methyl-1-(4-(methylsulfinyl)benzylidene)-1H-inden-3-yl)acetoxy)-4,6 dimethylphenyl)-3-methylbutanoic acid (50, 200 mg, 0.38 mmol) in dichloromethane (20 mL) was added Lawesson's reagent (77 mg, 0.19 mmol) at room temperature. After 2 h, the pure product was achieved by chromatography as yellow solid. (151 mg, 71%) $^1$H NMR (400 MHz, CDCl$_3$) δ 7.45 (d, J=8.2 Hz, 2H), 7.37-7.40 (m, 1H), 7.29 (d, J=8.3 Hz, 2H), 7.16 (s, 1H), 6.97 (dd, J=8.9, 2.3 Hz, 1H), 6.78 (s, 1H), 6.59 (td, J=8.9, 2.4 Hz, 1H), 6.52 (s, 1H), 3.80 (s, 2H), 2.73 (s, 2H), 2.55 (s, 3H), 2.51 (s, 3H), 2.25 (s, 3H), 2.19 (s, 3H), 1.52 (s, 6H).

Synthesis of 3-(2-(2-(5-fluoro-2-methyl-1-(4-(methylthio)benzylidene)-1H-inden-3-yl)acetoxy)-4,6-dimethylphenyl)-3-methylbutanethioic S-acid (HP-107)

To a solution of 3-(2-(2-(5-fluoro-2-methyl-1-(4-(methylthio)benzylidene)-1H-inden-3-yl)acetoxy)-4,6-dimethylphenyl)-3-methylbutanoic acid (51, 151 mg, 0.28 mmol) in dichloromethane (5 mL) was added Lawesson's reagent (56 mg). The pure product was achieved by chromatography as yellow solid. (98 mg, 60%). $^1$H NMR (400 MHz, CDCl$_3$): δ 7.46 (d, J=8.2 Hz, 2H), 7.40-7.43 (m, 1H), 7.30 (d, J=8.4 Hz, 2H), 7.20 (s, 1H), 6.98 (dd, J=8.9, 2.4 Hz, 1H), 6.79 (s, 1H), 6.64-6.56 (m, 2H), 3.83 (s, 2H), 2.91 (s, 2H), 2.55 (s, 3H), 2.50 (s, 3H), 2.29 (s, 3H), 2.22 (s, 3H), 1.43 (s, 6H).

Example 8. Synthesis of sodium 3-(2,4-dimethyl-6-(pivaloyloxy)phenyl)-3-methylbutanethioate (HP-108)

Hydrogen sulfide precursor HP-108 was synthesized in 5 steps, as shown in Scheme 13.

Scheme 13

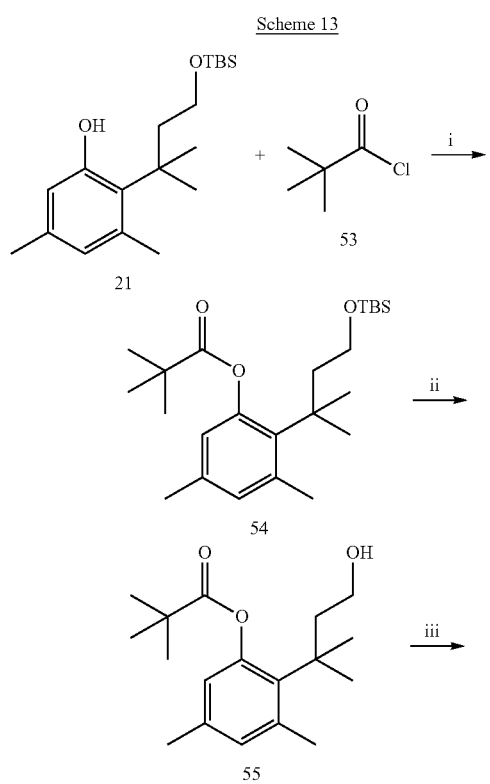

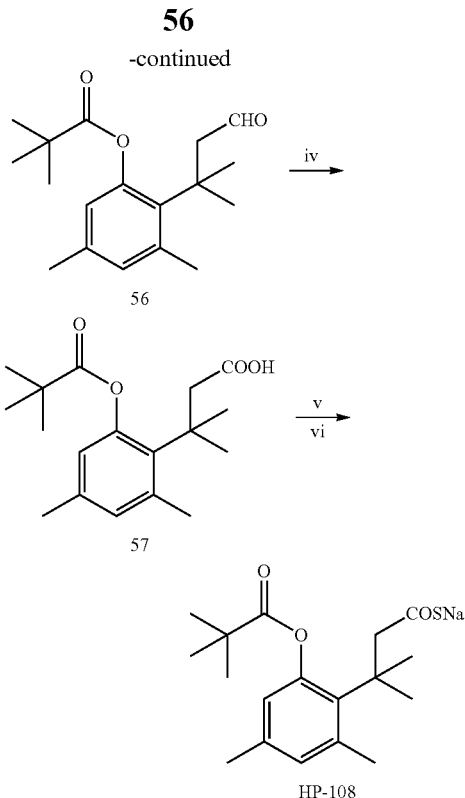

Reagents and conditions (i). Et$_3$N, DCM, DMAP, 0° C.-rt, 12 h; (ii) AcOH/H$_2$O, THF, rt, 12 h; (iii). PCC, DCM, rt, 2 h; (iv). NaClO$_2$/NaH$_2$PO$_4$, 2-methylbut-2-ene, t-BuOH, rt, 2 h; (v) Lawesson's Reagent, DCM, microwave, 6 min; (vi) NaOH, methanol, -78° C.

2-(4-((tert-butyldimethylsilyl)oxy)-2-methylbutan-2-yl)-3,5-dimethylphenyl pivalate (54). To a solution of 2-(4-((tert-butyldimethylsilyl)oxy)-2-methylbutan-2-yl)-3,5-dimethylphenol (21, 1.9 g, 5.9 mmol), DMAP (73 mg, 0.6 mmol) and Et3N (1.0 ml, 7.1 mmol) in DCM (150 mL) was added dropwise pivaloyl chloride (53, 0.85 g, 7.1 mmol) at room temperature and stirred for 4 h. Then the reaction was quenched with the addition of H$_2$O (100 mL), and solution was extracted with ethyl acetate (2×150 mL). The combined organic phase was dried over anhydrous Na2SO4 and evaporated under reduced pressure to give the crude product, which was purified by column chromatography (hexane:ethyl acetate=50:1) to give a colorless oil (2.35 g, 98%). 1H NMR (CDCl3): δ 6.78 (s, 1H), 6.41 (s, 1H), 3.50 (t, J=7.6 Hz, 2H), 2.53 (s, 3H), 2.22 (s, 3H), 2.04 (t, J=7.6 Hz, 2H), 1.47 (s, 6H), 1.36 (s, 9H), 0.85 (s, 9H), −0.02 (s, 6H); 13C NMR (CDCl3) δ 177.8, 151.1, 138.4, 136.1, 134.6, 132.1, 122.9, 60.9, 45.9, 39.4, 39.3, 32.0, 27.4, 26.1, 25.5, 20.3, 18.4, −5.2. For C24H42O3Si [M+H]+ 407.2976, found: 407.2967.

2-(4-hydroxy-2-methylbutan-2-yl)-3,5-dimethylphenyl pivalate (55). To a solution of 2-(4-((tert-butyldimethylsilyl)oxy)-2-methylbutan-2-yl)-3,5-dimethylphenyl pivalate (54, 2.3 g, 5.7 mmol) in THF (20 mL) was added H$_2$O (20 mL) and AcOH (60 mL). The reaction mixture was stirred at room temperature for 4 h, quenched with H$_2$O (50 mL), and extracted with ethyl acetate (2×150 mL). The combined organic phase was dried over anhydrous Na2SO4 and evaporated under reduced pressure, and purified silica gel column chromatography (hexane:ethyl acetate=5:1) as colorless oil (1.5 g, 90%). 1H NMR (CDCl3): δ 6.80 (s, 1H), 6.40 (s, 1H), 3.53 (t, J=7.2 Hz, 2H), 2.53 (s, 3H), 2.22 (s, 3H), 2.02 (t, J=7.2 Hz, 2H), 1.80 (s, 6H), 1.48 (s, 6H), 1.37

(s, 9H); 13C NMR (CDCl3): δ 178.6, 151.0, 138.5, 136.4, 134.3, 132.4, 122.9, 60.6, 45.7, 39.4, 39.3, 32.2, 27.3, 25.5, 20.3. For C18H29O3 [M+H]+ 293.2111, found: 293.2106.

3,5-dimethyl-2-(2-methyl-4-oxobutan-2-yl)phenyl pivalate (56). To a solution of PCC (2.1 g, 9.8 mmol) in DCM (20 mL) was added dropwise 2-(4-hydroxy-2-methylbutan-2-yl)-3,5-dimethylphenyl pivalate (55, 1.4 g, 4.8 mmol) in DCM (25 mL) at room temperature. After 2 h, the mixture was directly subjected to column chromatography (hexane:ethyl acetate=6:1) to obtain the pure product as colorless oil (1.2 g, 83%). 1H NMR (CDCl3): δ 9.52 (t, J=2.8 Hz, 1H), 6.82 (d, J=0.8 Hz, 1H), 6.46 (d, J=0.8 Hz, 1H), 2.83 (d, J=2.8 Hz, 2H), 2.54 (s, 3H), 2.23 (s, 3H), 1.95 (s, 6H), 1.37 (s, 9H); 13C NMR (CDCl3) δ 203.4, 177.8, 150.8, 137.8, 137.0, 133.0, 132.6, 123.2, 56.5, 39.4, 38.5, 31.8, 27.3, 25.6, 20.3. For C18H26O3 [M+H]+ 291.1955, found: 291.1952.

3-(2,4-dimethyl-6-(pivaloyloxy)phenyl)-3-methylbutanoic acid (57). To a solution of 3,5-dimethyl-2-(2-methyl-4-oxobutan-2-yl)phenyl pivalate (56, 1.15 g, 4.0 mmol) in t-BuOH (20 mL) and 2-methylbut-2-ene (4 mL), NaClO2 (540 mg, 6 mmol) in 0.67 M NaH2PO4 (4.5 mL) was added dropwise at room temperature. After 2 h, the reaction mixture was quenched with H₂O (20 mL), and extracted with ethyl acetate (2×100 ml). The combined organic phase was dried over anhydrous Na2SO4 and then evaporated under reduced pressure to give the crude product, which was purified by column chromatography (hexane:ethyl acetate=10:1) to yield a white solid (895 mg, 73%). 1H NMR (CDCl3): δ 6.78 (s, 1H), 6.44 (s, 1H), 2.84 (s, 2H), 2.54 (s, 3H), 2.22 (s, 3H), 1.57 (s, 6H), 1.37 (s, 9H); 13C NMR (CDCl3) δ 178.0, 177.3, 150.8, 138.2, 136.5, 133.7, 132.4, 122.9, 47.1, 39.4, 39.1, 31.4, 27.3, 25.5, 20.4. For C18H26O4 [M+H]+ 307.1904, found: 307.1899.

sodium 3-(2,4-dimethyl-6-(pivaloyloxy)phenyl)-3-methylbutanethioate (HP-108). To a solution of 3-(2,4-dimethyl-6-(pivaloyloxy)phenyl)-3-methylbutanoic acid (57, 120 mg, 0.39 mmol) in DCM (5 mL) was added Lawesson's reagent (79 mg, 0.20 mmol). The mixture was heated in a microwave at 100° C. for 6 min. The mixture was directly subjected to column chromatography (hexane:ethyl acetate=40:1) to obtain the pure product as colorless oil, which was then dissolved in 5 ml methanol. Then 3.0 ml of 0.1 M NaOH methanol solution was added to the reaction solution at −78° C. After 5 min, the mixture was allowed to warm to room temperature and the solvent was removed by vacuum. The final product was achieved by recrystallization in ether as a white solid (76 mg, 57%). 1H NMR (CDCl3): δ 6.81 (s, 1H), 6.48 (s, 1H), 4.39 (s, 1H), 3.14 (s, 2H), 2.56 (s, 3H), 2.24 (s, 3H), 1.56 (s, 6H), 1.40 (s, 9H); 13C NMR (CDCl3): δ 196.3, 177.7, 150.9, 138.2, 136.8, 133.0, 132.4, 123.0, 58.1, 40.0, 39.4, 31.5, 27.3, 25.7, 20.4. For C18H25NaO3S [M+H]+ 345.1495, found: 345.1485.

Example 9. Synthesis of 3-(2,4-dimethyl-6-(phosphonooxy)phenyl)-3-methylbutanethioic 5-acid (HP-109)

Hydrogen sulfide precursor HP-109 was synthesized in 6 steps, as shown in Scheme 14.

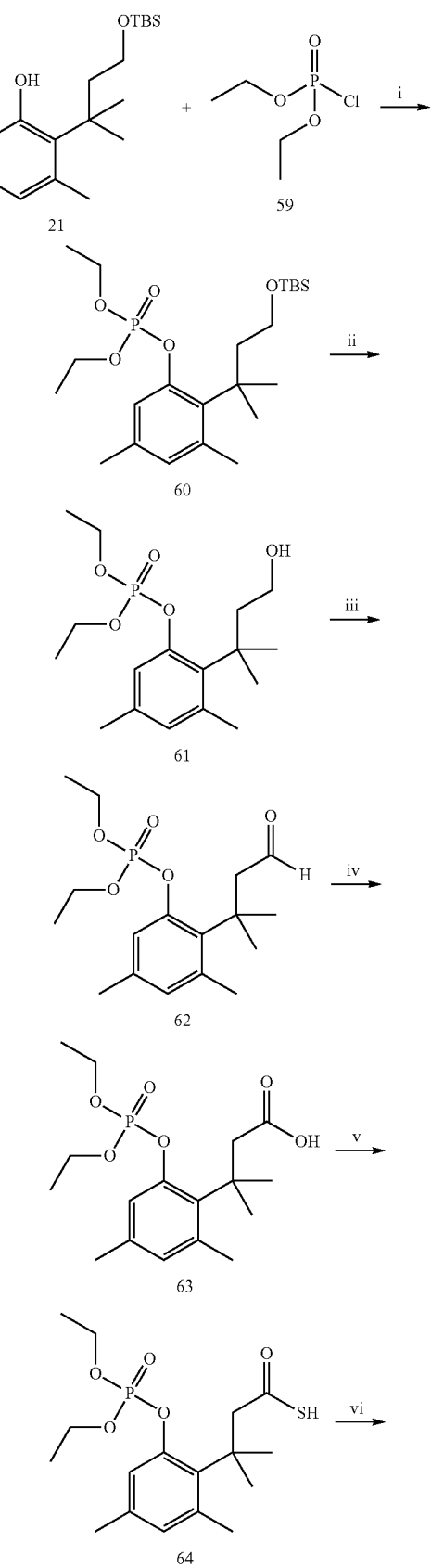

Scheme 14

-continued

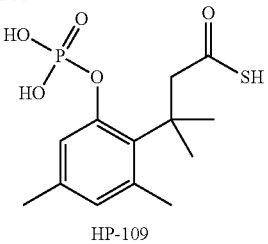

HP-109

Reagents and conditions (i) tBuOK, DCM, 0° C.-rt, 12 h, 98%; (ii) AcOH/H₂O, THF, rt, 49 h, 84%; (iii) Pyridinium chlorochromate (PCC), DCM, rt, 2 h, 82%; (iv) NaClO₂/NaH₂PO₄, 2-methylbut-2-ene, t-BuOH, rt, 2 h, 66%; (v) Lawesson's reagent, DCM, microwave, 6 min; 69%; (vi) TMSBr, CHCl₃, rt, 48 h, 91%.

Synthesis of 2-(4-((tert-butyldimethylsilyl)oxy)-2-methylbuta58n-2-yl)-3,5-dimethylphenyl diethyl phosphate (60)

To a solution of 2-(4-((tert-butyldimethylsilyl)oxy)-2-methylbutan-2-yl)-3,5-dimethylphenol (21, 4 g, 12.4 mmol) and tBuOK (2 g, 18.6 mmol) in DCM (40 mL) was added dropwise diethyl phosphorochloridate (59, 2.6 ml, 18.6 mmol) in 20 ml DCM at 0° C. during a period of 10 min. The mixture was allowed to warm to room temperature and was stirred for an additional 12 h. Then the reaction was quenched with the addition of H₂O (100 mL), and extracted with ethyl acetate (2×100 mL). The combined organic phase was dried over anhydrous Na₂SO₄ and evaporated under reduced pressure to give the crude product, which was purified by column chromatography (hexane:ethyl acetate=10:1) to give a colorless oil (5.56 g, 98%). ¹H NMR (400 MHz, CDCl₃) δ 7.11 (s, 1H), 6.69 (s, 1H), 4.29-4.07 (m, 4H), 3.48 (t, J=7.5 Hz, 2H), 2.48 (s, 3H), 2.21 (s, 3H), 2.08 (t, J=7.5 Hz, 2H), 1.52 (s, 6H), 1.31-1.34 (m, 6H), 0.82 (s, 10H), −0.05 (s, 6H). ¹³C NMR (100 MHz, CDCl₃) δ 150.5, 138.5, 136.1, 132.7 (d, J=8.1 Hz), 130.9, 118.7 (d, J=2.1 Hz), 77.5, 77.2, 76.8, 64.4 (d, J=5.9 Hz), 61.1, 45.8, 39.6, 32.2, 26.0, 25.7, 20.5, 18.3, 16.2 (d, J=6.8 Hz), −5.26.

Synthesis of diethyl (2-(4-hydroxy-2-methylbutan-2-yl)-3,5-dimethylphenyl) phosphate (61)

To a solution of 2-(4-((tert-butyldimethylsilyl)oxy)-2-methylbutan-2-yl)-3,5-dimethylphenyl diethyl phosphate (60, 5.46 g, 11.9 mmol) in tetrahydrofuran (THF, 60 mL) was added H₂O (60 mL) and AcOH (180 mL). All the solvents were evaporated under reduced pressure, and the crude product was purified by silica gel column chromatography (DCM:ethyl acetate=20:1) to give a colorless oil (3.4 g, 84%). ¹H NMR (400 MHz, CDCl₃) δ 7.03 (s, 1H), 6.68 (s, 1H), 4.15-4.22 (m, 4H), 3.46 (t, J=7.5 Hz, 2H), 2.45 (s, 3H), 2.18 (s, 3H), 2.09 (t, J=7.5 Hz, 2H), 1.48 (s, 6H), 1.30-1.34 (m, 6H). ¹³C NMR (100 MHz, CDCl₃) δ 150.3 (d, J=6.9 Hz), 138.5, 136.2, 132.6 (d, J=7.7 Hz), 131.1, 118.9 (d, J=2.0 Hz), 77.5, 77.2, 76.8, 64.52 (d, J=6.0 Hz), 60.4, 46.0, 39.5, 32.1, 25.6, 20.3, 16.1 (d, J=6.8 Hz).

Synthesis of 3,5-dimethyl-2-(2-methyl-4-oxobutan-2-yl)phenyl diethyl phosphate (62)

To a solution of PCC (4.0 g, 20.0 mmol) in DCM (30 mL) was added dropwise diethyl (2-(4-hydroxy-2-methylbutan-2-yl)-3,5-dimethylphenyl) phosphate (61, 3.4 g, 10 mmol) in DCM (50 mL) at room temperature. After 2 h, the mixture was directly subjected to column chromatography (DCM: ethyl acetate=10:1) to obtain the pure product as colorless oil (2.85 g, 82%). ¹H NMR (400 MHz, CDCl₃) δ 9.50 (s, 1H), 7.10 (s, 1H), 6.71 (s, 1H), 4.30-4.04 (m, 4H), 2.90 (d, J=1.6 Hz, 2H), 2.47 (s, 3H), 2.19 (s, 3H), 1.56 (s, 7H), 1.29 (t, J=6.9 Hz, 7H). ¹³C NMR (100 MHz, CDCl₃) δ 203.1, 149.9 (d, J=6.7 Hz), 138.0, 136.8, 131.2 (d, J=7.0 Hz), 119.0 (d, J=2.0 Hz), 77.5, 77.2, 76.8, 64.5 (d, J=5.8 Hz), 56.7, 38.4, 31.7, 25.6, 20.3, 16.1 (d, J=6.7 Hz).

Synthesis of 3-(2-((diethoxyphosphoryl)oxy)-4,6-dimethylphenyl)-3-methylbutanoic acid (63)

To a solution of 3,5-dimethyl-2-(2-methyl-4-oxobutan-2-yl)phenyl diethyl phosphate (62, 950 mg, 2.81 mmol) in t-BuOH (15 mL) and 2-methylbut-2-ene (3 mL), NaClO₂ (380 mg, 4.2 mmol) in 0.67 M NaH₂PO₄ (3 mL) was added dropwise at room temperature. After 2 h, the reaction mixture was quenched with 1M HCl (20 mL), and extracted with ethyl acetate (2×30 ml). The combined organic phase was dried over anhydrous Na₂SO₄ and then evaporated under reduced pressure to give the crude product, which was purified by column chromatography (DCM:ethyl acetate=10:1) to yield a colorless oil (670 mg, 66%). 1H NMR (400 MHz, CDCl3) δ 9.52 (t, J=2.4 Hz, 1H), 7.12 (s, 1H), 6.72 (s, 1H), 4.25-4.10 (m, 4H), 2.92 (d, J=2.4 Hz, 2H), 2.49 (s, 3H), 2.21 (s, 3H), 1.57 (s, 6H), 1.31 (t, J=7.0 Hz, 6H). ¹³C NMR (100 MHz, CDCl₃) δ 176.8, 150.2 (d, J=6.8 Hz), 138.5, 136.4, 132.0 (d, J=7.8 Hz), 131.2, 118.8 (d, J=2.0 Hz), 77.5, 77.2, 76.8, 64.7 (d, J=5.9 Hz), 47.4, 39.2, 31.7, 25.6, 20.4, 16.1 (d, J=6.8 Hz).

Synthesis of 3-(2-((diethoxyphosphoryl)oxy)-4,6-dimethylphenyl)-3-methylbutanethioic S-acid (64)

To a solution of 3-(2-((diethoxyphosphoryl)oxy)-4,6-dimethylphenyl)-3-methylbutanoic acid (63, 180 mg, 0.50 mmol) in DCM (5 mL) was added Lawesson's reagent (101 mg, 0.25 mmol). The mixture was heated in a microwave at 100° C. for 6 min. The mixture was directly subjected to column chromatography (hexane:ethyl acetate=5:1) to obtain the pure product as colorless oil. (129 mg, 69%). ¹H NMR (400 MHz, CDCl₃) δ 7.09 (s, 1H), 6.71 (s, 1H), 4.31-4.04 (m, 4H), 3.25 (s, 2H), 2.50 (s, 3H), 2.21 (s, 3H), 1.57 (s, 6H), 1.33 (t, J=7.0 Hz, 6H). ¹³C NMR (100 MHz, CDCl₃) δ 196.4, 150.1 (d, J=6.9 Hz), 138.4, 136.7, 131.2 (d, J=7.9 Hz), 118.7 (d, J=2.0 Hz), 77.5, 77.2, 76.8, 64.69 (d, J=5.8 Hz), 58.6, 40.0, 31.6, 25.7, 20.5, 16.2 (d, J=6.7 Hz).

Synthesis of 3-(2,4-dimethyl-6-(phosphonooxy)phenyl)-3-methylbutanethioic S-acid (HP-109)

To a solution of 3-(2-((diethoxyphosphoryl)oxy)-4,6-dimethylphenyl)-3-methylbutanethioic S-acid (64, 40 mg, 0.11 mmol) in anhydrous CHCl₃ (5 mL) was added TMSBr (117 μl, 0.88 mmol) dropwise at room temperature under N₂. The mixture was stirred at room temperature for 48 h, after which 1 ml H₂O and 1 ml MeOH was added and the mixture was stirred at room temperature for 30 min. All the solvents were evaporated under reduced pressure to afford a yellow solid. (32 mg, 91%). ¹H NMR (400 MHz, MeOD) δ 7.10 (s, 1H), 7.10 (s, 1H), 6.69 (s, 1H), 6.69 (s, 1H), 3.34 (s, 2H), 2.48 (s, 3H), 2.19 (s, 3H), 1.58 (s, 6H).

Example 10. Synthesis of 3-(2-acetoxy-4,6-dimethylphenyl)-3-methylbutanoic dithioperoxyanhydride (HP-110)

Hydrogen sulfide precursor HP-110 was synthesized in one step, as shown in Scheme 15

Scheme 15

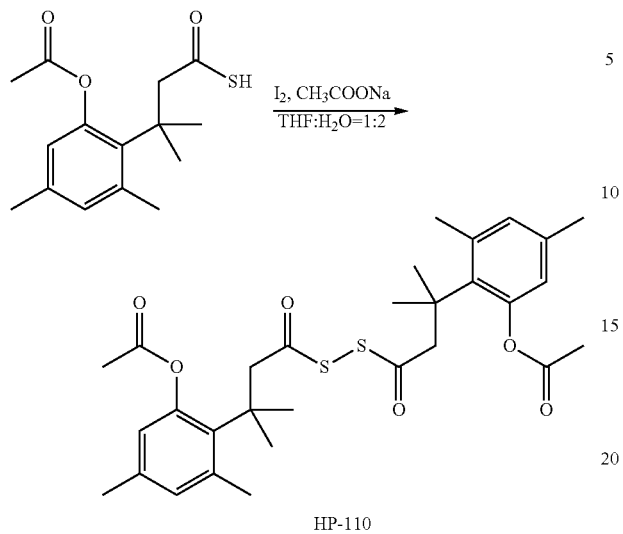

Synthesis of 3-(2-acetoxy-4,6-dimethylphenyl)-3-methylbutanoic dithioperoxyanhydride (HP-110)

To a solution of 3-(2-acetoxy-4,6-dimethylphenyl)-3-methylbutanethioic S-acid (90 mg, 0.32 mmol) and CH$_3$COONa (26 mg, 0.32 mmol) in THF (2 mL) and H$_2$O (1 mL) was added I$_2$ (41 mg, 0.16 mmol) at room temperature. The mixture was stirred at room temperature for 5 min. H$_2$O (20 ml) was added and the mixture was extracted with ethyl acetate (2×10 ml). The combined organic phase was washed by saturated sodium thiosulfate aqueous solution and dried over anhydrous Na$_2$SO$_4$ and then evaporated under reduced pressure to give the product. (90 mg, 100%). $^1$H NMR (CD$_3$OD, 400 MHz): δ 6.80 (s, 2H), 6.61 (s, 2H), 3.26 (s, 4H), 2.51 (s, 6H), 2.32 (s, 6H), 2.23 (s, 6H), 1.57 (s, 12H).

Example 11. Synthesis of 3-(2-acetoxy-4,6-dimethylphenyl)-3-methylbutanoic dithioperoxyanhydride (HP-111)

Hydrogen sulfide precursor HP-111 was synthesized in one step, as shown in Scheme 16.

Scheme 16

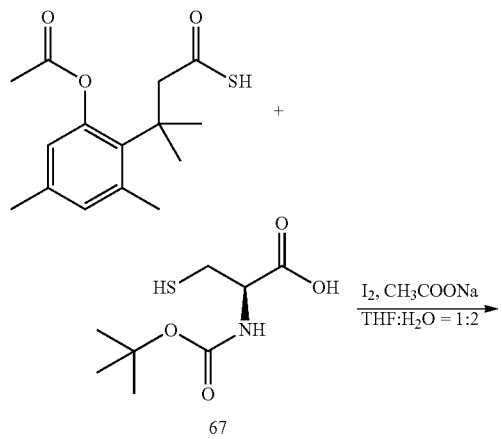

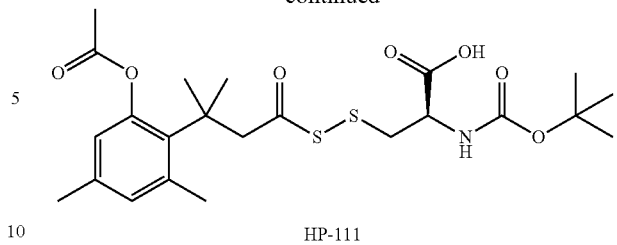

Synthesis of S-((3-(2-acetoxy-4,6-dimethylphenyl)-3-methylbutanoyl)thio)-N-(tert-butoxycarbonyl)-L-cysteine (68)

To a solution of 3-(2-acetoxy-4,6-dimethylphenyl)-3-methylbutanethioic S-acid (10, 40 mg, 0.14 mmol), CH$_3$COONa (100 mg, 1.12 mmol) and (tert-butoxycarbonyl)-L-cysteine (67, 220 mg, 1.00 mmol) in THF (2 mL) and H$_2$O (1 mL) was added I$_2$ (142 mg, 0.56 mmol) at room temperature. The mixture was stirred at room temperature for 5 min. H$_2$O (20 ml) was added and the mixture was extracted with ethyl acetate (2×10 ml). The combined organic phase was washed by saturated sodium thiosulfate aqueous solution and dried over anhydrous Na$_2$SO$_4$ and then evaporated under reduced pressure to give a yellow oil, which was purified by column chromatography (DCM: MeOH=30:1) to yield a colorless oil (45 mg, 64%). $^1$H NMR (CD$_3$OD, 400 MHz): δ 6.81 (s, 1H), 6.60 (s, 1H), 5.70 (d, J=6.8 Hz, 1H), 4.23 (d, J=3.6 Hz, 1H), 3.25-2.97 (m, 4H), 2.53 (s, 3H), 2.33 (s, 3H), 2.22 (s, 3H), 1.57 (s, 6H), 1.45 (s, 12H).

Example 12. Esterase-Induced Hydrogen Sulfide Release from H$_2$S Precursors (HPs)

H$_2$S Measurement by a Fluorescent Probe WSP-5.

The ability of esterases to release hydrogen sulfide, as shown in Scheme 17, was examined using a well-known hydrogen sulfide fluorescent probe WSP-5 (3-oxo-3H-spiro[isobenzofuran-1,9'-xanthene]-3',6'-diyl bis(2-(pyridin-2-yldisulfanyl)benzoate) to detect its production in the hydrogen sulfide precursor (HP) reaction mixture. A 200 μM solution of HP 10 was treated with porcine liver esterase (Aldrich, E2884), 4 u/mL) in PBS at 37° C., then 5 μL reaction mixture was taken into 995 μL acetonitrile and detected using WSP-5. The results are shown in FIG. 1 which indicate that HP 10 releases H$_2$S in phosphate buffer saline with 4 units of esterase.

Figure 3:
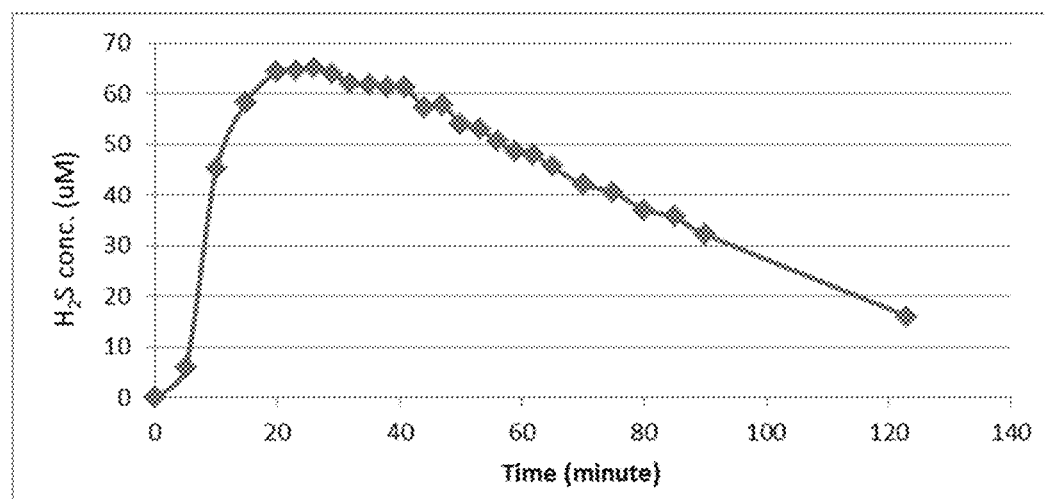
FIG. 3 shows esterase-induced $H_2S$ release from HP-101 in PBS buffer, detected using WSP-5.

The WSP-5 probe was used to detect the concentration of H$_2$S in the reaction solution as shown in FIG. 3. Because of the high volatility of H$_2$S, when the escape rate is greater than formation rate, the concentration decreases. The peak concentration of H$_2$S also appeared within about 25 min.

HP-101 (final concentration: 200 μM) or other control compounds were added to PBS (10 mL) buffer containing esterase (1 unit/mL) at 37° C. After 15 minutes, aliquots of 100 μL samples were taken out and added into 100 μL PBS containing 50 μM WSP-5 and 100 μM CTAB in 96-well plate. After mixing and standing for 5 min at room temperature, the fluorescent intensities at 535 nm were recorded by a plate reader with excitation at 485 nm. (FIG. 1).

The data in FIG. 1 was obtained for enzymatic reactions as follows: a) WSP-5 only in PBS; b) WSP-5+200 μM HP-101 in PBS; c) WSP-5+200 μM HP-101 in DMEM (No FBS), no cells; d) WSP-5+200 μM HP-101 in DMEM (with FBS)+ cells; e) WSP-5+200 μM HP-101 in DMEM (with FBS), no cells; f) WSP-5+200 μM HP-101+1 unit/mL of Esterase; g) WSP-5+200 μM GYY1437; h) WSP-5+1 unit/mL Esterase. The concentration of WSP-5 is 50 μM, and the intensities of fluorescence were recorded after 5 min of incubation of WSP-5 with different substrates at room temperature.

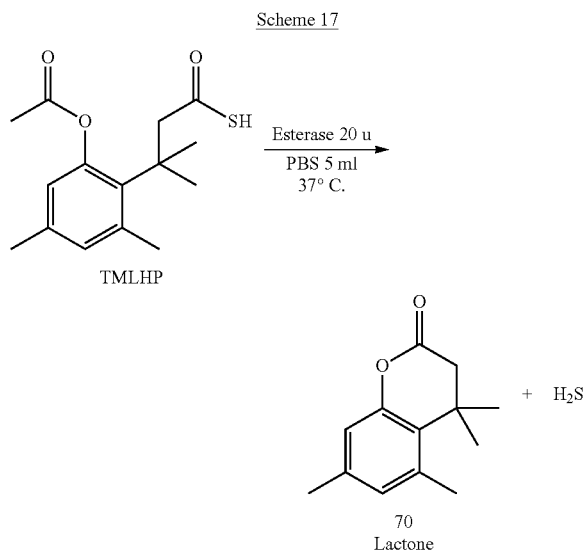

Esterase Triggered Lactone Formation from HPs as Monitored by LC-MS/MS.

Figure 2:
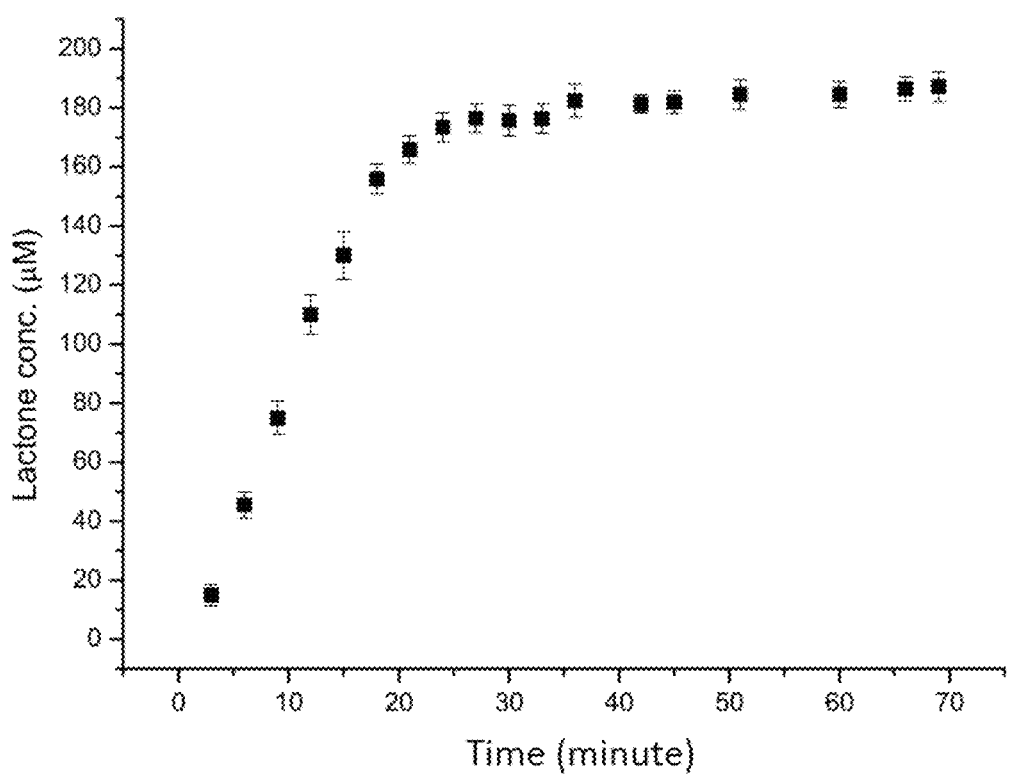
FIG. 2 shows esterase-induced lactone formation via release of $H_2S$ from trimethyl lock based $H_2S$ precursor HP-101 in PBS buffer, detected using LC-MS.

The release of hydrogen sulfide and its release rate were detected using LC-MS. A 200 μM HP 10 reaction mixture was treated with esterase for 25 min which led to formation of more than 180 μM of the lactone product as shown in FIG. 2. Such results indicate that more than 90% of $H_2S$ was released.

HP-101 (final concentration: 200 μM) was added to PBS (10 mL) with 1 unit/mL esterase at 37° C. Reaction mixture (10 μL) was taken out every 3 minutes and added into a vial containing 990 μL methanol at −78° C. for 5 minutes. The mixture (14.5×1000 rp) was centrifuged, and the supernatant was used as the sample for LC-MS/MS analysis (Agilent 1100 LC, 6410 TripleQ MS/MS, Ion transition: 205.0/135.0, positive mode).

$H_2S$ concentration measurement by an electrode probe ISO-$H_2S$-2.

HPs (compounds HP-101, HP-102, HP-103, HP-104; final concentration=200 μM) were added to an incubation chamber (World Precision Instruments; WPI) containing phosphate buffer (10 mM; pH 7.4, 10 mL), and esterase (1 unit/mL) at 37° C. $H_2S$ formation was detected with the use of a 2-mm $H_2S$-selective microelectrode (ISO-$H_2S$-2; WPI) attached to an Apollo 1100 Free Radical Analyser (WPI) and shown as picoamps current generated. A standard curve (using $Na_2S.9H_2O$) was generated by following literature procedures, but using PBS containing esterase at 37° C. (FIG. 4).

The tunability of the release rates was studied by varying the ester group and factors controlling the lactonization step. Variations of the ester group allows for tuning the rate of the unmasking step. It was reasoned that modifying the acyl moiety should help tune the hydrolysis rates. The second direction in tuning $H_2S$ releasing rates is based on controlling the lactonization rate by varying the number of methyl groups in the system. It is well known that the lactonization of compound 1 is much faster than that of o-hydroxydihydrocinnamic acids 3 and 4, which lack pendant methyl groups (Scheme 18) and thus has decreased entropic control of the conformation favorable for lactonization. Therefore, HP-102, -103, and -104 were synthesized to tune the release rates. HP-102 and HP-104 contain a large acyl moiety cyclopropanecarbonyl ester and HP-103 and HP-104 lack two methyl groups on phenyl ring.

Figure 4:
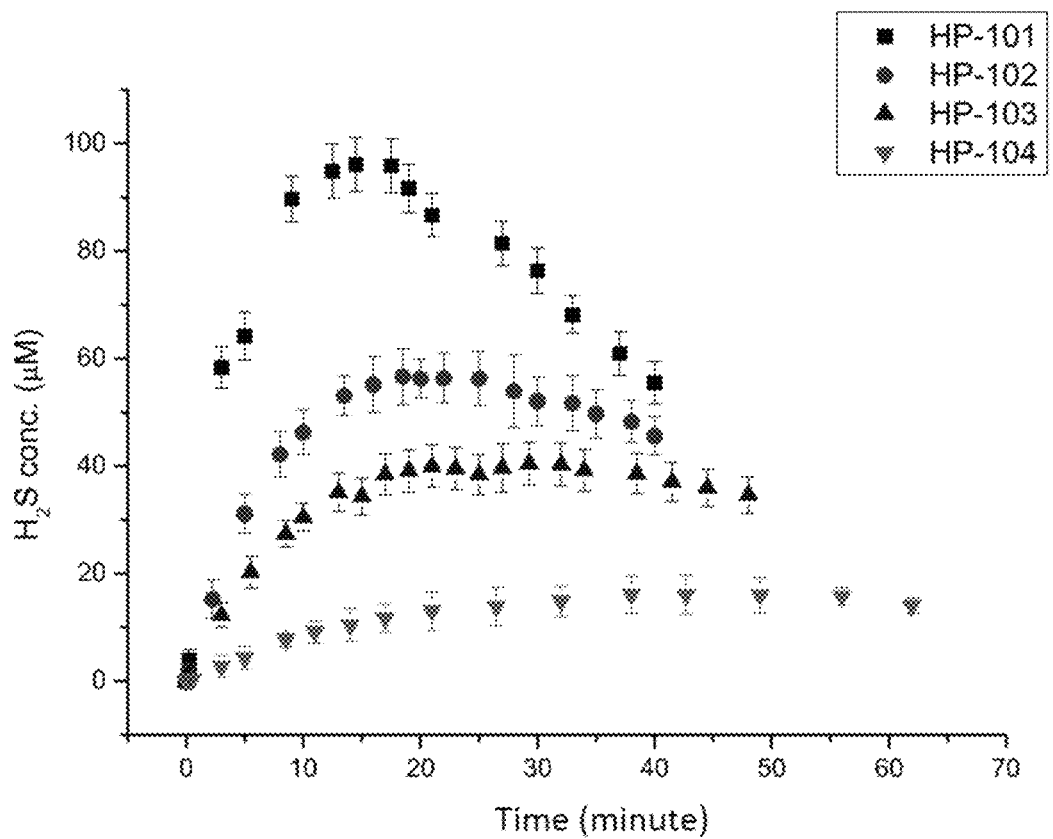
FIG. 4 shows $H_2S$ generation curves for $H_2S$ precursor compounds (200 μM in PBS) with 1 unit/mL esterase at 37° C. (p=0.95, n=3).

$H_2S$ release from these precursors was studied (FIG. 4). The precursor compounds showed very different $H_2S$ release rates. For 200 μM of the precursor compound in PBS at 37° C. with 1 unit/mL PLE, the peak $H_2S$ concentration for the fastest one, HP-101, was about 95 μM at 15 min; and for the slowest one, HP-104, it was about 13 μM at 43 min. Such results demonstrate that the same concentration of the precursor compound may mean very different effective $H_2S$ concentrations, depending on the release rates.

Scheme 18

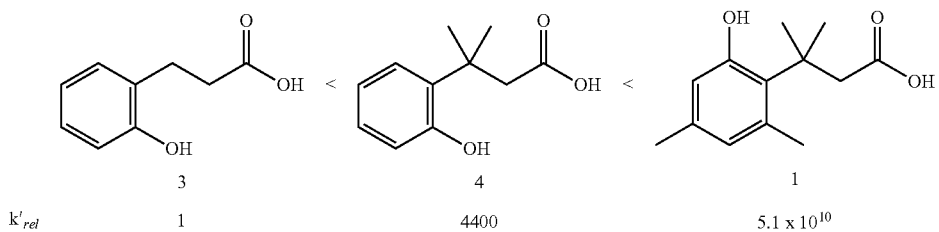

Figure 5:
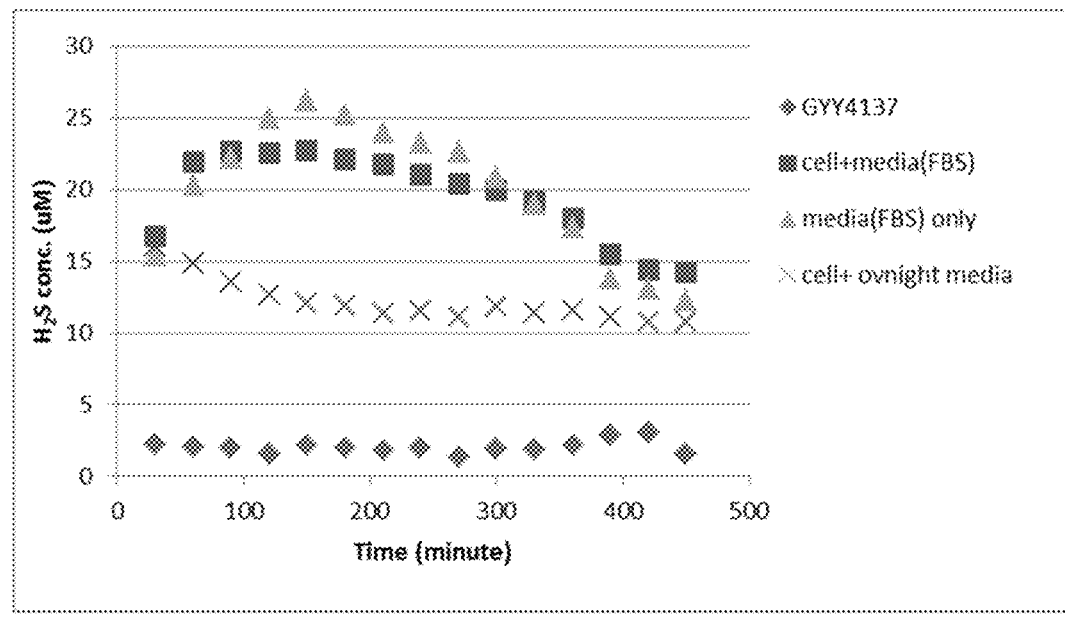
FIG. 5 shows a comparison of $H_2S$ release from: HP-101 in DMEM media; HP-101 in cells+DMEM media without FBS; and HP-101 in cells+DMEM media with FBS.

Example 13. Esterase-Induced Hydrogen Sulfide Release in $H_2S$ Precursor HP-101 in Cell Media The in vitro release of $H_2S$ from HP-101 was studied under various conditions such as HP-101 (200 μM) in DMEM media (5 mL), cell+DMEM media without FBS, and cell+DMEM media with FBS. FIG. 5 shows that HP-101 in the DMEM alone did not release $H_2S$; however, when HP-101 was added into the media collected after overnight of cell culture, $H_2S$ was released at a moderate rate, due to the presence of esterases produced by the cells.

Figure 6:
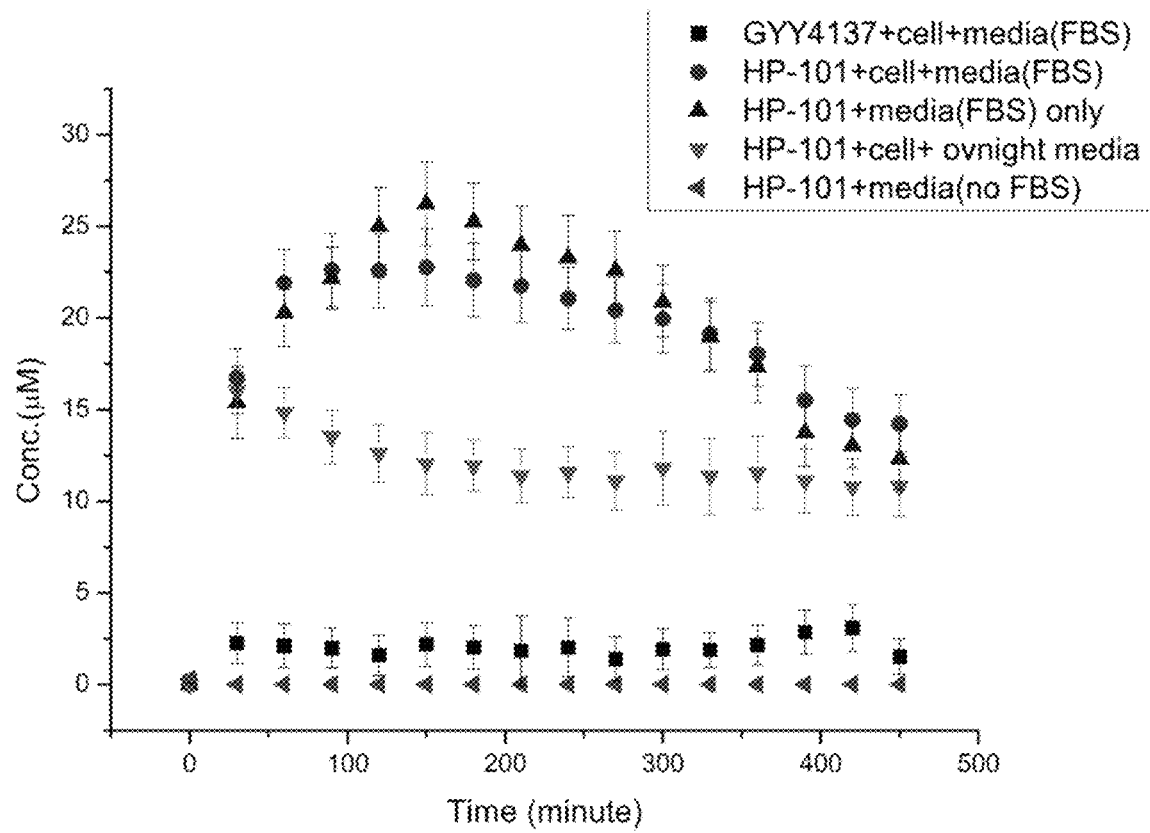
FIG. 6 shows standard curves for $H_2S$ release from HP-101 (200 μM) in cell culture media with or without FBS as detected using an electrode probe. (n=3, p=0.95)

HP-101 (200 μM) was added to an incubation chamber (World Precision Instruments; WPI) containing cell culture media (10 mL) at 37° C. $H_2S$ formation was detected with the use of an ISO-$H_2S$-2 probe attached to an Apollo 1100 Free Radical Analyser and shown as picoamps current generated. A standard curve (using Na2S.9H2O) was also generated under the same conditions. The results indicated that HP-101 in the DMEM did not release H$_2$S; however, when HP-101 was added into the media collected after overnight of cell culturing, H$_2$S was released at a moderate rate, presumably due to the presence of esterases produced by the cells (FIG. 6).

Example 14. Esterase-Triggered Release of H$_2$S and the Parent Drugs from Hybrid Precursor Compounds The reaction of esterase-triggered H$_2$S hybrid drug (HP-105) hydrolysis is shown in Scheme 19.

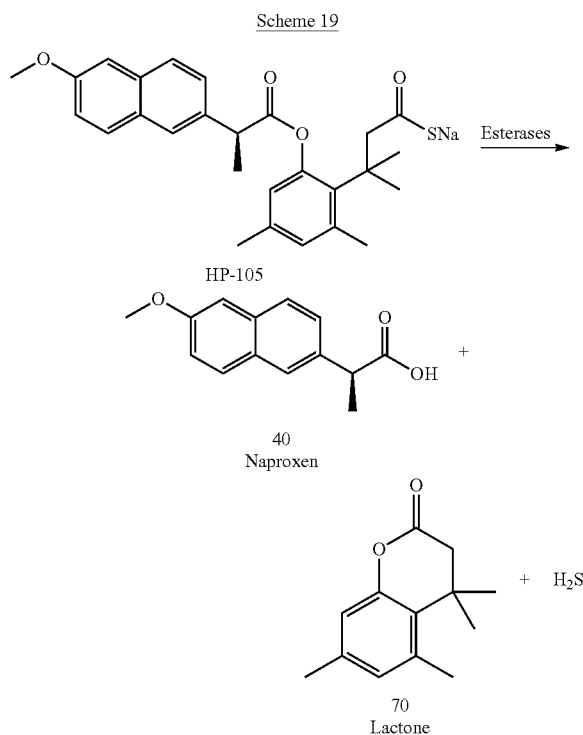

Figure 7A:
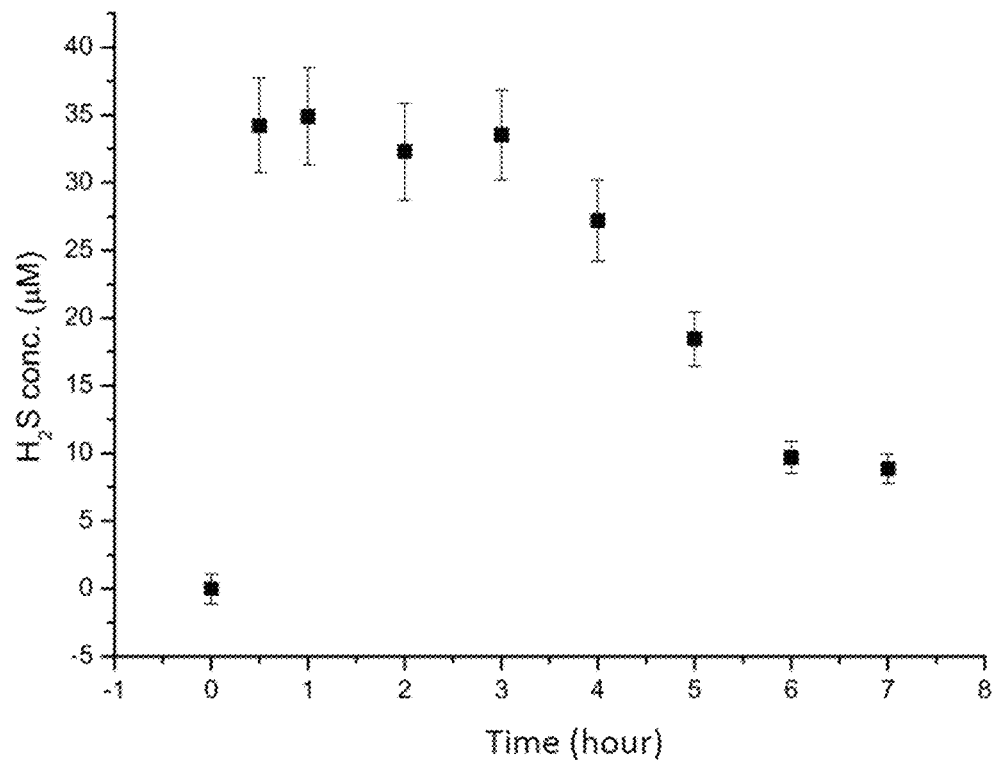
FIG. 7A shows a standard curves for $H_2S$ release from HP-105 (200 μM) in PBS at 37° C. with 20 unit/mL pig liver esterase (PLE) (n=3, p=0.95).
Figure 7B:
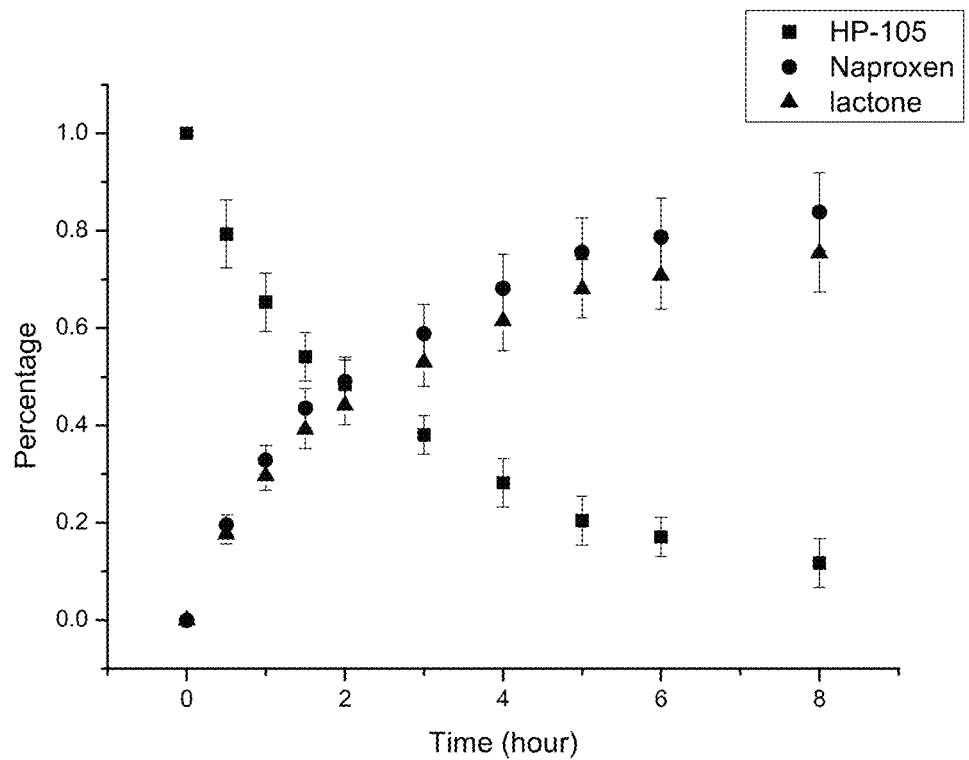
FIG. 7B shows a reaction course for a mixture containing 200 μM HP-105 in PBS (1% DMSO) with esterase 20 unit/mL at 37° C. (p=0.95, n=3).
Figure 8A:
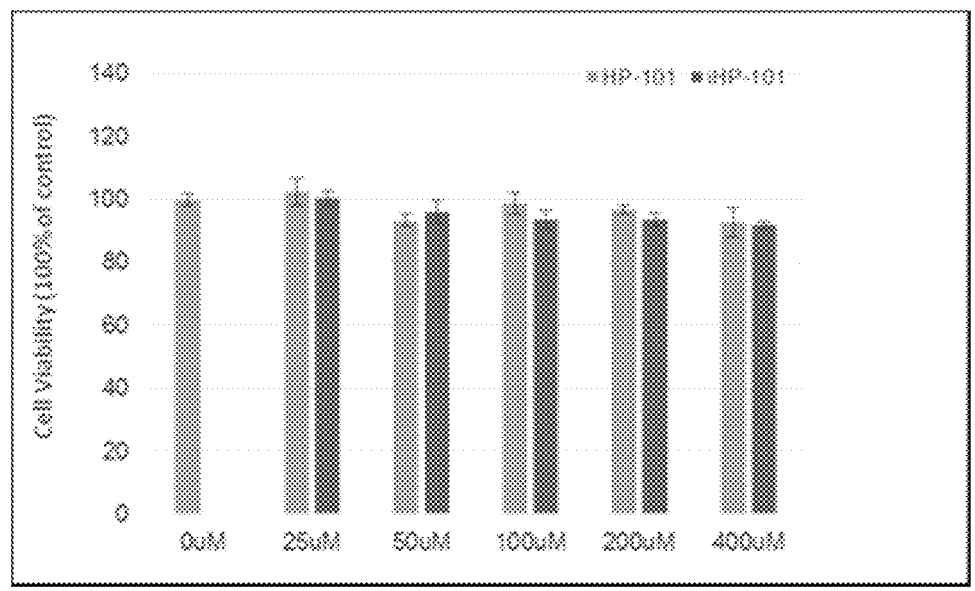
FIG. 8A shows the cytotoxicity of HP compounds (n=4, p=0.95).
Figure 8A:
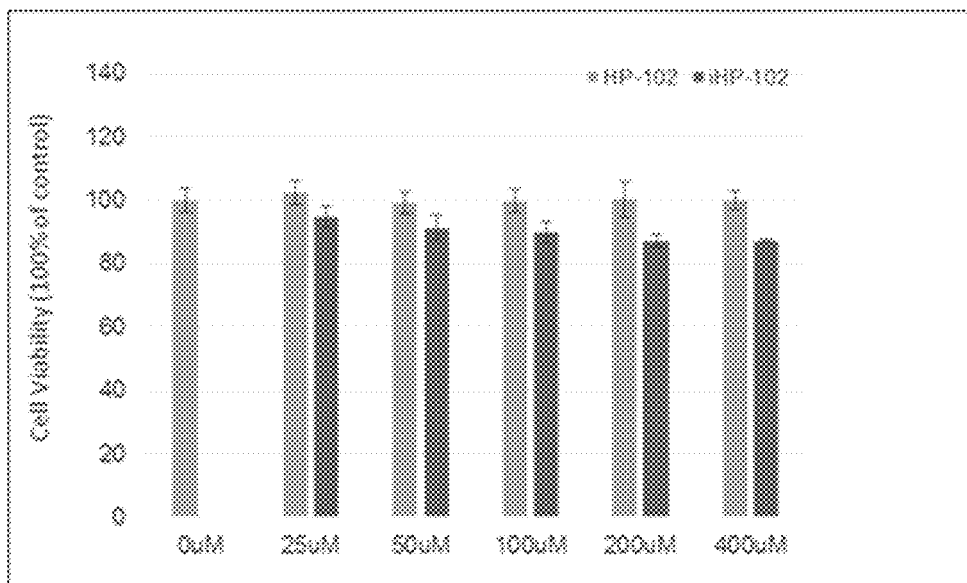
Figure 8B:
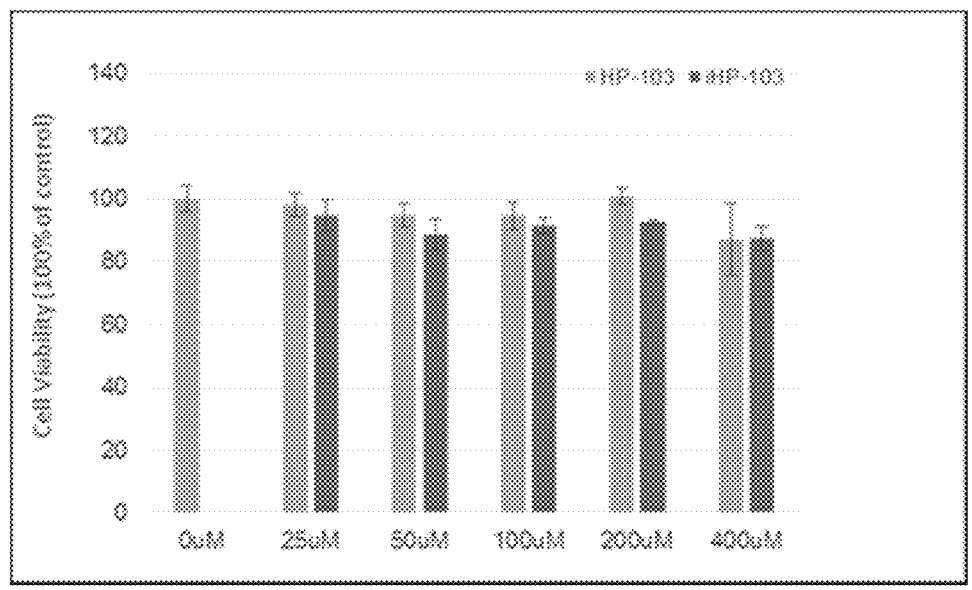
FIG. 8B shows the cytotoxicity of HP compounds (n=4, p=0.95).
Figure 8B:
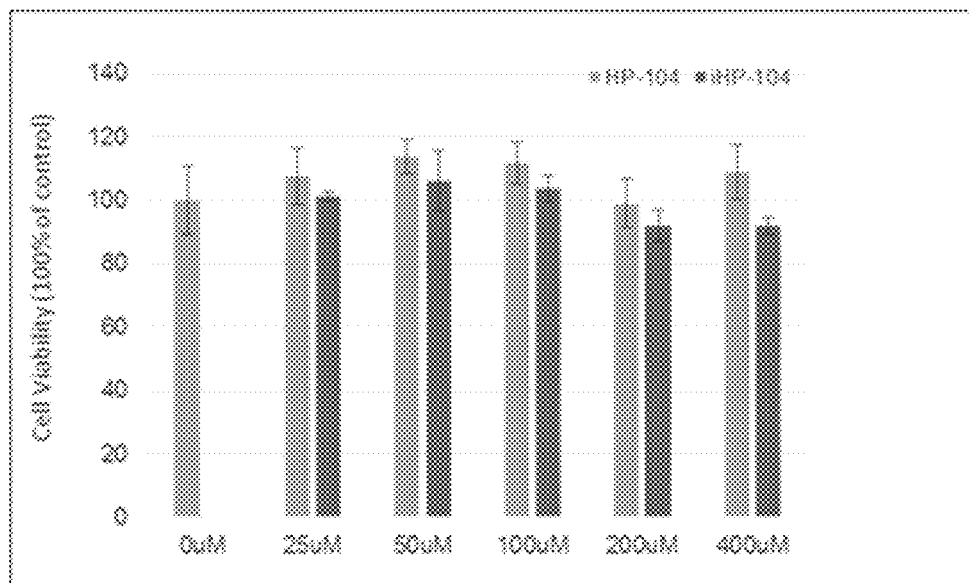

To a 9.9 mL phosphate buffer (pH 7.4) solution was added 11.1 mg (200 unit) PLE, followed by the addition of 100 μL 20 mM HP-105 stock solution (final concentration: 200 μM). The resultant solution was sealed and stirred at 37° C. At every 30 min, 200 μL of reaction solution was taken into a 1.5 mL vial containing 200 μL zinc acetate (1%, w/v). Then the vial was centrifuged for 10 min. (14.5×1000 rp). The supernatant was removed and the precipitate was washed with PBS solution (100 μL×2). 600 μL of N,N-dimethyl-1,4-phenylenediaminesulfate (0.2% w/v in 20% H$_2$SO$_4$ solution) and 50 μL ferric chloride (10% w/v in 0.2% H$_2$SO$_4$ solution) was added to the vial. Then the vial was centrifuged for 5 min (14.5×1000 rp). The absorbance (at 740 nm) of the resulting solution was measured (after stirring for 10 min). H$_2$S concentration was calculated based on a calibration curve of NaHS. (FIG. 7A). HPLC kinetic studies showed that HP-105 could generate naproxen and H$_2$S by treatment with an esterase (FIG. 7B).

Example 15. Kinetic Studies of Esterase-Triggered Lactone Formation

HPs (final concentration: 200 μM) were added to PBS (10 mL) with 1 unit/mL esterase at 37° C. 200 μL reaction mixture was taken out every 10 minutes and added into a vial containing 600 μL ethanol at −78° C. for 5 minutes. The mixture (14.5×1000 rp, 90 seconds) was centrifuged, and the supernatant was used as the sample for HPLC. 200 μL HPLC samples were injected into Shimadzu Prominence UFLC (column: Waters C18 3.5 μM, 4.6×100 mm, injection loop volume: 20 μL). The mobile phase was acetonitrile (MeCN)/H$_2$O (pH=4.0) with ratios defined in the table below (Table 1).

TABLE 1

HPLC monitored esterase triggering lactone formation of HPs. (n = 3, p = 0.95)

| | HP-101 | HP-102 | HP-103 | HP-104 | HP-105 |
|---|---|---|---|---|---|
| Eluent conditions | 50% MeCN 0~20 min | 60% MeCN 0~20 min | 45% MeCN 0~20 min | 55% MeCN 0~20 min | Method b |
| Retention time of HPs (min) | 13.6 ± 0.2 | 9.7 ± 0.2 | 7.7 ± 0.2 | 8.3 ± 0.2 | 20.7 ± 0.3 |
| Retention time of the lactones (min) | 10.7 ± 0.2 | 5.5 ± 0.2 | 8.5 ± 0.2 | 6.1 ± 0.2 | 9.6 ± 0.3 |

Method b: 45% MeCN, 0-10 min; 45%~75% MeCN, 10-15 min; 75% MeCN, 15-20 min; 75%~45% MeCN, 20-25 min.

The lactone product formation by HPLC was monitored, and $t_{1/2}$ values ranging from 13 to 99 min were found for 200 μM precursor compounds in the presence of PLE. Such results further demonstrated the concept of tuning the H$_2$S release rates.

TABLE 2

Half-lives of HP compounds.

| | HP-101 | HP-102 | HP-103 | HP-104 |
|---|---|---|---|---|
| $T_{1/2}$ (min) | 13.0 ± 2.4 | 28.7 ± 1.5 | 44.5 ± 2.1 | 99.0 ± 8.9 |

200 μM precursor compounds in PBS with esterase 1 unit/mL at 37° C., p = 0.95, n = 3.

Example 16. Cytotoxicity Study of HPs (HP-101-104)

RAW 264.7 cells were seeded in 96-well plate one day before the experiment. Different concentrations of HP compounds or inactive oxyacid versions of the compounds ("iHP compounds") were directly dissolved in cell culture media and added into the RAW 264.7 cell culture. The cells were then incubated with the compounds for 24 hours at 37° C. with 5% CO$_2$. The cell viability was tested by the MTT assay. Specifically, after 24 hr of incubation, 0.5 mg/mL MTT (3-(4,5-dimethylthiazol-2-yl)-2, 5-diphenyltetrazolium Bromide) was added into the cell culture for 4 hours. Thereafter, the supernatant was removed and 100 μL DMSO was added into the wells containing the cells. After shaking gently for 3 minutes, absorbance at 570 nm was read by a plate reader (FIG. 8).

Example 17. Anti-Inflammation Study of HPs

Figure 9A:
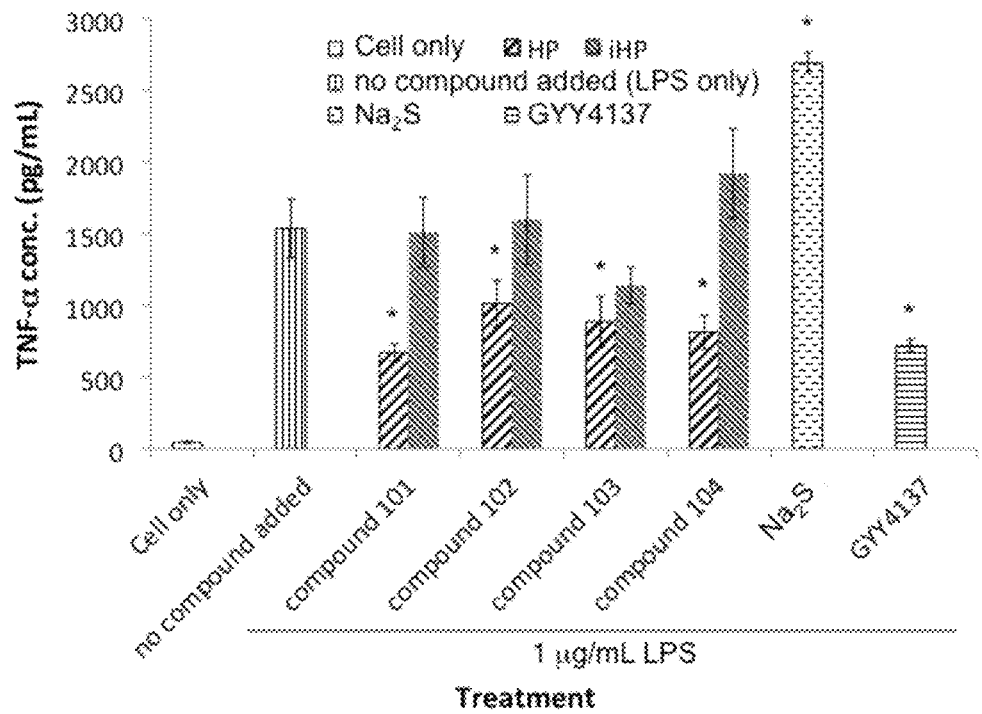
FIG. 9A shows TNF-α concentrations of RAW 264.7 cell culture media after 1-hour co-treatment with treatment with HPs, iHPs $Na_2S$ and GYY4137 (50 μM) and LPS.
Figure 9B:
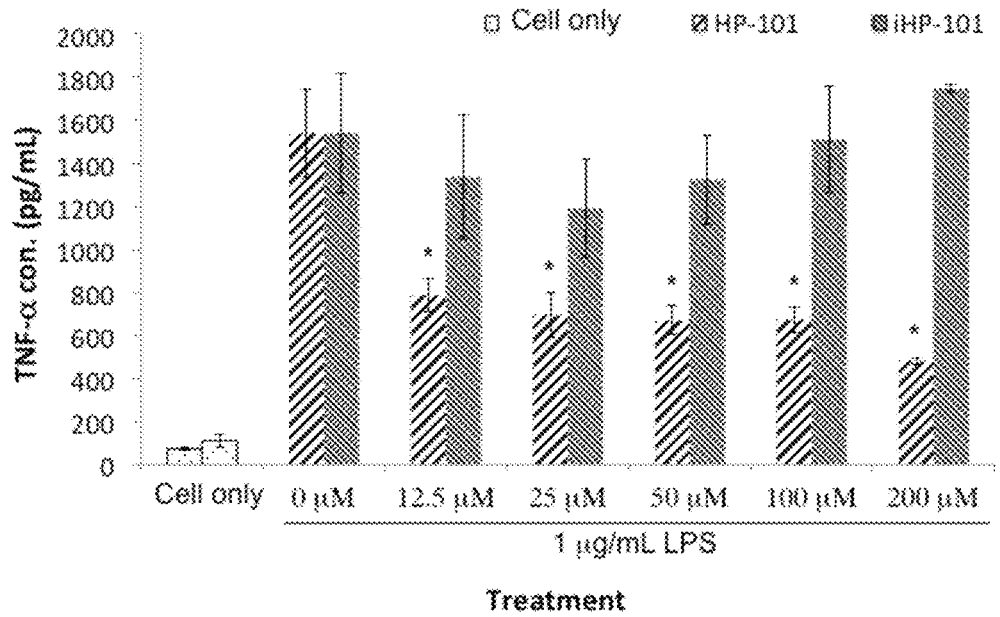
FIG. 9B shows TNF-α concentrations of RAW 264.7 cell culture media after 1-hour co-treatment with various concentrations of HP-101 and iHP-101 (n=4*: p<0.05) and LPS.

RAW 264.7 cells were seeded in the 48-well plate one day before the experiment. Lipopolysaccharide was added into the cell culture to initiate the inflammatory response in RAW 264.7 cells and to trigger the expression of cytokines. RAW 264.7 cells were co-treated with HPs (HP-101, HP-102, HP-103, HP-104) or iHPs, 1 unit/mL esterase and 1 μg/mL of LPS for 1 hour. Thereafter, the cell culture supernatant was collected. The concentrations of TNF-α in the cell culture supernatant was quantified by a commercial ELISA kit (ELISA Ready-SET-Go!®-eBioscience). (FIG. 9) The results showed that only the precursor compounds and GYY 4137 effectively inhibited TNF-α secretion, and Na$_2$S showed pro-inflammatory effect, which is similar to other hydrogen sulfide done systems (see, e.g., Whiteman, et al., *Antioxid. Redox Signal.* 2010, 12, 1147-1154). None of the iHPs showed the same effect, which clearly demonstrated that the inhibition effect on TNF-α production came from the H$_2$S released from the respective precursor compound.

Example 18. Synthesis of 3-(2,4-dimethyl-6-(phosphonooxy)phenyl)-3-methylbutanoic dithioperoxyanhydride. (HP-113)

Hydrogen persulfide precursor HP-113 was synthesized in two steps, as shown in Scheme 20.

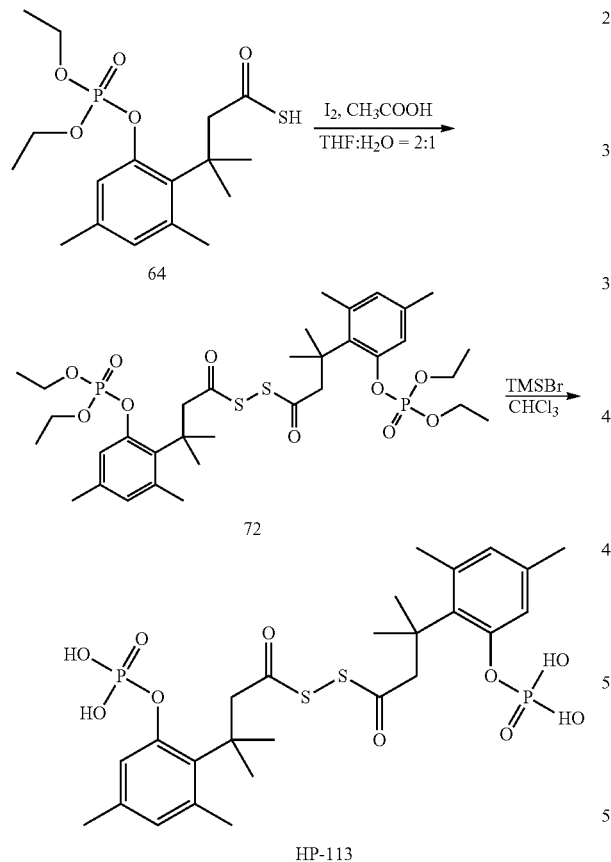

Synthesis of 3-(2-((diethoxyphosphoryl)oxy)-4,6-dimethylphenyl)-3-methylbutanoic dithioperoxyanhydride(72)

To a solution of 3-(2-((diethoxyphosphoryl)oxy)-4,6-dimethylphenyl)-3-methylbutanethioic S-acid (120 mg, 0.32 mmol) and CH$_3$COONa (26 mg, 0.32 mmol) in THF (2 mL) and H$_2$O (1 mL) was added I$_2$ (40 mg, 0.16 mmol) at room temperature. The mixture was stirred at room temperature for 5 min. H$_2$O (20 ml) was added and the mixture was extracted with ethyl acetate (2×10 ml). The combined organic phase was washed by saturated sodium thiosulfate aqueous solution and dried over anhydrous Na$_2$SO$_4$ and then evaporated under reduced pressure to give the product. (110 mg, 92%). $^1$H NMR (CD$_3$OD, 400 MHz): δ 7.11 (s, 2H), 6.69 (s, 2H), 4.24-4.14 (m, 8H), 3.34 (s, 4H), 2.47 (s, 6H), 2.22 (s, 6H), 1.59 (s, 12H), 1.33-1.30 (m, 12H).

Synthesis of 3-(2,4-dimethyl-6-(phosphonooxy)phenyl)-3-methylbutanoic dithioperoxyanhydride (HP-113)

To a solution of 3-(2-((diethoxyphosphoryl)oxy)-4,6-dimethylphenyl)-3-methylbutanoic dithioperoxyanhydride (100 mg, 0.13 mmol) in anhydrous CHCl$_3$ (5 mL) was added TMSBr (200 ul, 1.6 mmol) dropwise at room temperature under N$_2$. The mixture was stirred at room temperature for 48 h, after which 1 ml H$_2$O and 1 ml MeOH was added and the mixture was stirred at room temperature for 30 min. All the solvents were evaporated under reduced pressure to afford a yellow solid, which was purify by C18 column. (14 mg, 16%). $^1$H NMR (400 MHz, MeOD) δ 7.30 (s, 2H), 6.56 (s, 2H), 3.48 (s, 4H), 2.48 (s, 6H), 2.19 (s, 6H), 1.63 (s, 12H).

Example 19. Synthesis of 3-methyl-3-(2-(phosphonooxy)phenyl)butanoic dithioperoxyanhydride (HP-114)

Hydrogen persulfide precursor HP-114 was synthesized in six steps, as shown in Scheme 21.

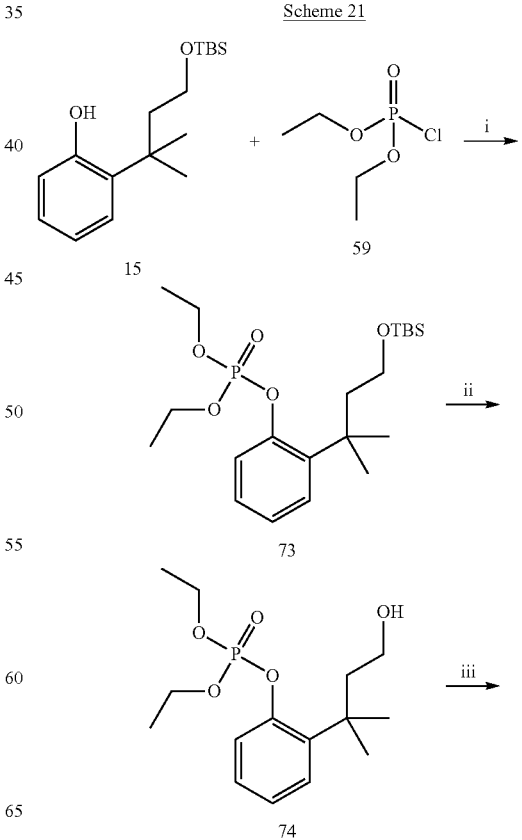

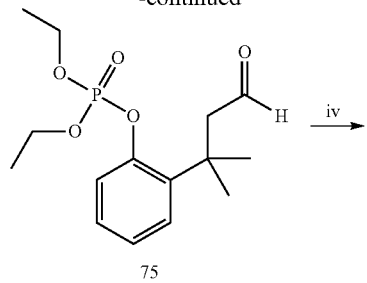

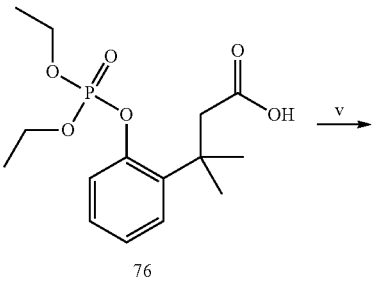

HP-114

Reagents and conditions (i) tBuOK, DCM, 0° C.-rt, 12 h, 62%; (ii) AcOH/H₂O, THF, rt, 4 h, 89%; (iii) Pyridinium chlorochromate (PCC) DCM, rt, 2 h, 59%; (iv) NaClO₂/NaH₂PO₄, 2-methylbut-2-ene, t-BuOH, rt, 2 h, 84%; (v) Lawesson's reagent, DCM, microwave, 6 min; 80%; (vi) I₂, CH₃COONa, THF/H₂O = 2:1, rt, 5 min; 65% (vii) TMSBr, CHCl₃, rt, 48 h, 27%.

2-(4-((tert-butyldimethylsilyl)oxy)-2-methylbutan-2-yl)phenyl diethyl phosphate (73)

To a solution of 2-(4-((tert-butyldimethylsilyl)oxy)-2-methylbutan-2-yl)phenol (2 g, 6.8 mmol) and tBuOK (1.2 g, 10 mmol) in DCM (40 mL) was added dropwise diethyl phosphorochloridate (1.5 ml, 10 mmol) in 20 ml DCM at 0° C. during a period of 10 min. The mixture was allowed to warm to room temperature and was stirred for an additional 12 h. Then the reaction was quenched with the addition of H₂O (100 mL), and extracted with ethyl acetate (2×100 mL). The combined organic phase was dried over anhydrous Na₂SO₄ and evaporated under reduced pressure to give the crude product, which was purified by column chromatography (hexane:ethyl acetate=10:1) to give a colorless oil (1.8 g, 62%). ¹H NMR (400 MHz, CDCl₃) δ 7.11 (d, J=8.0 Hz, 1H), 7.29-7.26 (m, 1H), 7.18-7.14 (m, 1H), 7.07-7.03 (m, 1H), 4.22-4.20 (m, 4H), 3.39 (t, J=7.6 Hz, 2H), 2.07 (t, J=7.6 Hz, 2H), 1.38 (s, 6H), 1.38-1.32 (m, 6H), 0.82 (s, 9H), -0.07 (s, 6H). ¹³C NMR (100 MHz, CDCl₃) δ 150.1 (d, J=7.0 Hz), 137.5 (d, J=9.0 Hz), 128.4, 127.5, 124.2, 119.2 (d, J=2.0 Hz), 64.5 (d, J=6.0 Hz), 60.7, 43.7, 37.1, 29.2, 26.0, 18.3, 16.3 (d, J=7.0 Hz), -5.3.

Diethyl (2-(4-hydroxy-2-methylbutan-2-yl)phenyl) phosphate (74)

To a solution of 2-(4-((tert-butyldimethylsilyl)oxy)-2-methylbutan-2-yl)phenyl diethyl phosphatediethyl phosphate (1.7 g, 3.9 mmol) in tetrahydrofuran (THF, 20 mL) was added H₂O (20 mL) and AcOH (60 mL). All the solvents were evaporated under reduced pressure, and the crude product was purified by silica gel column chromatography (DCM:ethyl acetate=20:1) to give a colorless oil (1.1 g, 89%). ¹H NMR (400 MHz, CDCl₃) δ 7.39 (d, J=8.0 Hz, 1H), 7.26-7.21 (m, 1H), 7.15-7.10 (m, 1H), 7.04-7.00 (m, 1H), 4.21-4.17 (m, 4H), 3.82 (t, J=7.2 Hz, 2H), 2.13 (t, J=7.2 Hz, 2H), 1.37 (s, 6H), 1.31-1.27 (m, 6H).

Diethyl (2-(2-methyl-4-oxobutan-2-yl)phenyl) phosphate (75)

To a solution of PCC (1.5 g, 7.0 mmol) in DCM (10 mL) was added dropwise diethyl (2-(4-hydroxy-2-methylbutan-2-yl)phenyl) phosphate (1.1 g, 3.5 mmol) in DCM (20 mL) at room temperature. After 2 h, the mixture was directly subjected to column chromatography (DCM:ethyl acetate=10:1) to obtain the pure product as colorless oil (650 mg, 59%). ¹H NMR (400 MHz, CDCl₃) δ 9.43 (t, J=2.8 Hz, 1H), 7.49 (d, J=8.0 Hz, 1H), 7.35-7.32 (m, 1H), 7.26-7.20 (m, 1H), 7.13-7.09 (m, 1H), 4.27-4.18 (m, 4H), 2.88 (d, J=2.8 Hz, 2H), 1.48 (s, 6H), 1.35-1.32 (m, 6H). ¹³C NMR (100 MHz, CDCl₃) δ 203.1, 149.7 (d, J=4.0 Hz), 136.0 (d, J=8.0 Hz), 128.3, 128.0, 124.8, 119.7 (d, J=2.0 Hz), 64.7 (d, J=5.0 Hz), 54.0, 36.4, 29.0, 16.2 (d, J=6.0 Hz).

3-(2-((diethoxyphosphoryl)oxy)phenyl)-3-methylbutanoic acid (76)

To a solution of diethyl (2-(2-methyl-4-oxobutan-2-yl) phenyl) phosphate (75, 600 mg, 1.9 mmol) in t-BuOH (12 mL) and 2-methylbut-2-ene (2 mL), NaClO₂ (260 mg, 2.9 mmol) in 0.67 M NaH₂PO₄ (2.5 mL) was added dropwise at room temperature. After 2 h, the reaction mixture was quenched with 1M HCl (20 mL), and extracted with ethyl acetate (2×30 ml). The combined organic phase was dried over anhydrous Na₂SO₄ and then evaporated under reduced pressure to give the crude product, which was purified by column chromatography (DCM:ethyl acetate=10:1) to yield a colorless oil (530 mg, 84%). ¹H NMR (400 MHz, CDCl₃) δ 7.40 (d, J=8.0 Hz, 1H), 7.34-7.31 (m, 1H), 7.20-7.15 (m, 1H), 7.09-7.05 (m, 1H), 4.27-4.12 (m, 4H), 2.85 (s, 2H), 1.50 (s, 6H), 1.35-1.31 (m, 6H). $^{13}$C NMR (100 MHz, CDCl$_3$) δ176.1, 149.7 (d, J=7.0 Hz), 136.5 (d, J=8.0 Hz), 128.4, 127.9, 124.6, 119.4 (d, J=1.0 Hz), 64.8 (d, J=6.0 Hz), 45.4, 36.8, 31.2, 28.6, 16.1 (d, J=6.0 Hz).

3-(2-((diethoxyphosphoryl)oxy)phenyl)-3-methylbutanethioic S-acid (77)

To a solution of 3-(2-((diethoxyphosphoryl)oxy)phenyl)-3-methylbutanoic acid (120 mg, 0.36 mmol) in DCM (5 mL) was added Lawesson's reagent (74 mg, 0.5 mmol). The mixture was heated in a microwave at 100° C. for 6 min. The mixture was directly subjected to column chromatography (hexane:ethyl acetate=5:1) to obtain the pure product as colorless oil. (100 mg, 80%). $^1$H NMR (400 MHz, CDCl$_3$) δ 7.47 (d, J=8.4 Hz, 1H), 7.34-7.33 (m, 1H), 7.24-7.20 (m, 1H), 7.13-7.09 (m, 1H), 4.31-4.21 (m, 4H), 3.19 (s, 2H), 1.50 (s, 6H), 1.38-1.35 (m, 6H). $^{13}$C NMR (100 MHz, CDCl$_3$) δ196.2, 149.8 (d, J=7.0 Hz), 136.0 (d, J=9.0 Hz), 128.4, 128.2, 124.7, 119.4, 64.8 (d, J=6.0 Hz), 56.0, 37.7, 28.5, 16.3 (d, J=7.0 Hz).

3-(2-((diethoxyphosphoryl)oxy)-4,6-dimethylphenyl)-3-methylbutanoic 3-(2-((diethoxyphosphoryl)oxy)phenyl)-3-methylbutanoic dithioperoxyanhydride (78). To a solution of 3-(2-((diethoxyphosphoryl)oxy)phenyl)-3-methylbutanethioic S-acid (77 mg, 0.22 mmol) and CH$_3$COONa (18 mg, 0.22 mmol) in THF (2 mL) and H$_2$O (1 mL) was added I$_2$ (28 mg, 0.11 mmol) at room temperature. The mixture was stirred at room temperature for 5 min. H$_2$O (20 ml) was added and the mixture was extracted with ethyl acetate (2×10 ml). The combined organic phase was washed by saturated sodium thiosulfate aqueous solution and dried over anhydrous Na$_2$SO$_4$ and then evaporated under reduced pressure to give the product. (50 mg, 65$^1$H NMR (400 MHz, CDCl$_3$) δ 7.46 (d, J=8.4 Hz, 2H), 7.30-7.26 (m, 2H), 7.21-7.18 (m, 2H), 7.09-7.05 (m, 2H), 4.26-4.18 (m, 8H), 3.26 (s, 4H), 1.49 (s, 12H), 1.34-1.31 (m, 12H). $^{13}$C NMR (100 MHz, CDCl$_3$) δ191.2, 149.9, 135.9 (d, J=8.0 Hz), 128.2, 128.2, 124.6, 119.4, 53.0, 56.0, 38.0, 28.4, 16.3 (d, J=7.0 Hz).

3-methyl-3-(2-(phosphonooxy)phenyl)butanoic dithioperoxyanhydride. (HP-114) To a solution of 3-(2-((diethoxyphosphoryl)oxy)-4,6-dimethylphenyl)-3-methylbutanoic 3-(2-((diethoxyphosphoryl)oxy)phenyl)-3-methylbutanoic dithioperoxyanhydride (45 mg, 0.065 mmol) in anhydrous CHCl$_3$ (5 mL) was added TMSBr (116 ul, 0.91 mmol) dropwise at room temperature under N$_2$. The mixture was stirred at room temperature for 48 h, after which 1 ml H$_2$O and 1 ml MeOH was added and the mixture was stirred at room temperature for 30 min. All the solvents were evaporated under reduced pressure to afford a yellow solid, which was purified by C18 column chromatography. (10 mg, 27%). $^1$H NMR (400 MHz, MeOD) δ 7.48 (d, J=7.6 Hz, 2H), 7.27 (d, J=7.6 Hz, 2H), 7.17 (t, J=7.6 Hz, 2H), 7.00 (t, J=7.6 Hz, 2H), 3.38 (s, 4H), 1.49 (s, 12H).

Example 20. H$_2$S$_2$ Release from Compound HP-110

Stock solutions of fluorescent probe DSP-3 (0.5 mM; see, J. Am. Chem. Soc. 2014, 136, 7257-7260) were prepared in CH$_3$CN and a stock solution of cetrimonium bromide (CTAB, 5 mM) was prepared in EtOH. Stock solutions of HP-110 (2.5 mM) were prepared in DMSO and 10 units/ml esterase from porcine liver was prepared in PBS (pH=7.4). Na$_2$S$_4$ (1 mM) was freshly prepared in PBS (pH=7.4).

Test samples were prepared as follows. For Group 1, 0.2 ml HP-110 was mixed with 10 ml 10 units/ml esterase. For Group 2, 0.2 ml DMSO was mixed with 10 ml 10 units/ml esterase. For Group 3, 0.2 ml HP-110 was mixed with 10 ml PBS. For Group 4, 0.2 ml DMSO and 0.5 ml Na$_2$S$_4$ was mixed with 9.5 ml 10 units/ml esterase.

Figure 10:
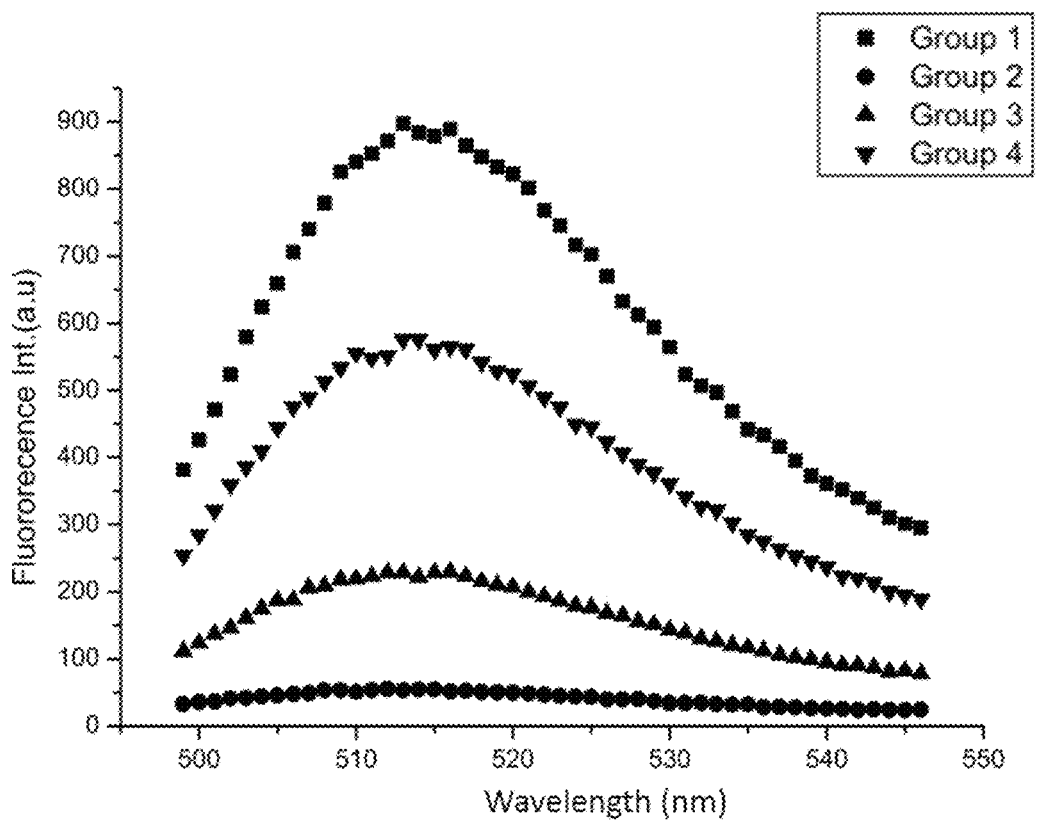
FIG. 10 shows $H_2S_2$ release from compound HP-110 (Group 1), detected using DSP-3, compared with control samples.

All groups were incubated at 37° C. for 5 min, after which 4 ml sample from each groups were extracted to new test tubes and 1 g NaCl was added. To each group, 20 μl CTAB and 80 μl DSP-3 were added immediately after they were cooled down to room temperature. After 5 min, 3 ml of the reaction solution from each group were transferred into cells for fluorescence measurement ($\lambda_{ex}$=490 nm). The data is shown in FIG. 10.

Example 21. H$_2$S$_2$ Release from Compound HP-113

Stock solutions of DSP-3 (0.5 mM) were prepared in CH$_3$CN and a stock solution of cetrimonium bromide (CTAB, 5 mM) was prepared in EtOH. Stock solutions of HP-113 (10 mM) were prepared in MeOH and 20 units/ml phosphatase was prepared in PBS (pH=7.4). Na$_2$S$_2$ (1 mM) was freshly prepared in PBS (pH=7.4).

Test samples were prepared as follows. For Group 1, 40 μl HP-113 was mixed with 4 ml 20 units/ml phosphatase. For Group 2, 40 μl MeOH was mixed 4 ml 20 units/ml phosphatase. For Group 3, 40 μl HP-113 was mixed with 4 ml PBS. For Group 4, 200 μl Na$_2$S$_2$ was mixed 4 ml 20 units/ml phosphatase.

Figure 11:
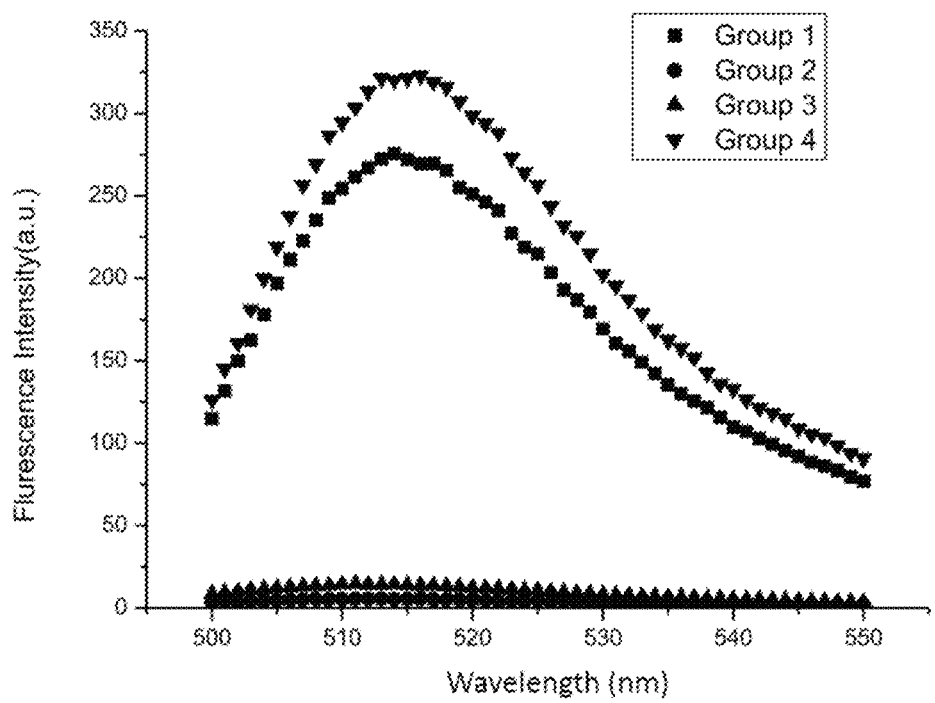
FIG. 11 shows $H_2S_2$ release from compound HP-113 (Group 1) compared with control samples.

All groups were incubated at 37° C. for 5 min. To each groups, 20 μl CTAB and 80 μl DSP-3 were added immediately after they were cooled down to room temperature. After 5 min, 3 ml of the reaction solution from each group were transferred into cells for fluorescence measurement ($\lambda_{ex}$=490 nm). The data is shown in FIG. 11.

Figure 12:
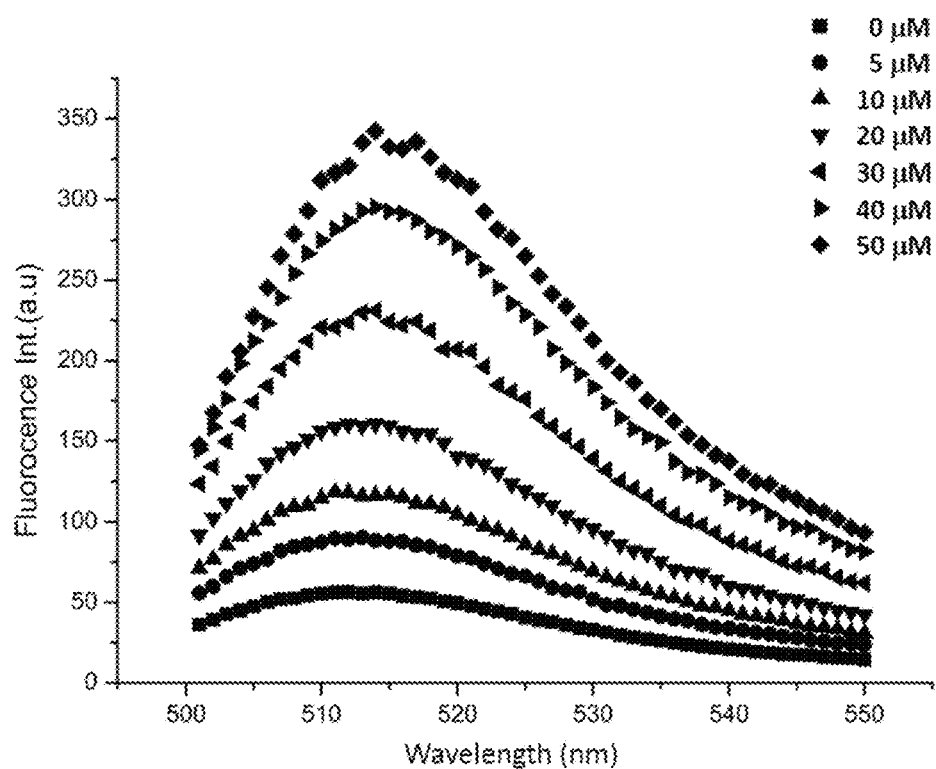
FIG. 12 shows $H_2S_2$ release in reaction mixtures containing varying concentrations of compound HP-113.

Stock solutions of DSP-3 (1 mM) were prepared in CH$_3$CN and a stock solution of cetrimonium bromide (CTAB, 5 mM) was prepared in EtOH. Stock solutions of HP-113 (10 mM) were prepared in MeOH and 10 units/ml phosphatase was prepared in PBS (pH=7.4). Different volumes of HP-113 stock solution, 20 μl CTAB and 80 μl DSP-3 were mixed with 4 ml 10 units/ml phosphatase. The reaction mixtures were incubated at 37° C. for 60 min and, after cooling down to room temperature, 3 ml of the reaction solution from each group was transferred into cells for fluorescence measurement ($\lambda_{ex}$=490 nm). The data is shown in FIG. 12.

Example 22. H$_2$S$_2$ Release from Compound HP-114

Stock solutions of DSP-3 (0.5 mM) were prepared in CH$_3$CN and a stock solution of cetrimonium bromide (CTAB, 5 mM) was prepared in EtOH. Stock solutions of HP-114 (10 mM) were prepared in MeOH and 20 units/ml phosphatase was prepared in PBS (pH=7.4). Na$_2$S$_2$ (1 mM) was freshly prepared in PBS (pH=7.4).

Test samples were prepared as follows. For Group 1, 40 μl HP-114 was mixed with 4 ml 20 units/ml phosphatase. For Group 2, 40 μl MeOH was mixed 4 ml 20 units/ml phosphatase. For Group 3, 40 μl HP-114 was mixed with 4 ml PBS. For Group 4, 200 μl Na$_2$S$_2$ was mixed 4 ml 20 units/ml phosphatase.

All groups were incubated at 37° C. for 5 min. To each groups, 20 μl CTAB and 80 μl DSP-3 were added immediately after they were cooled down to room temperature.

Figure 13:
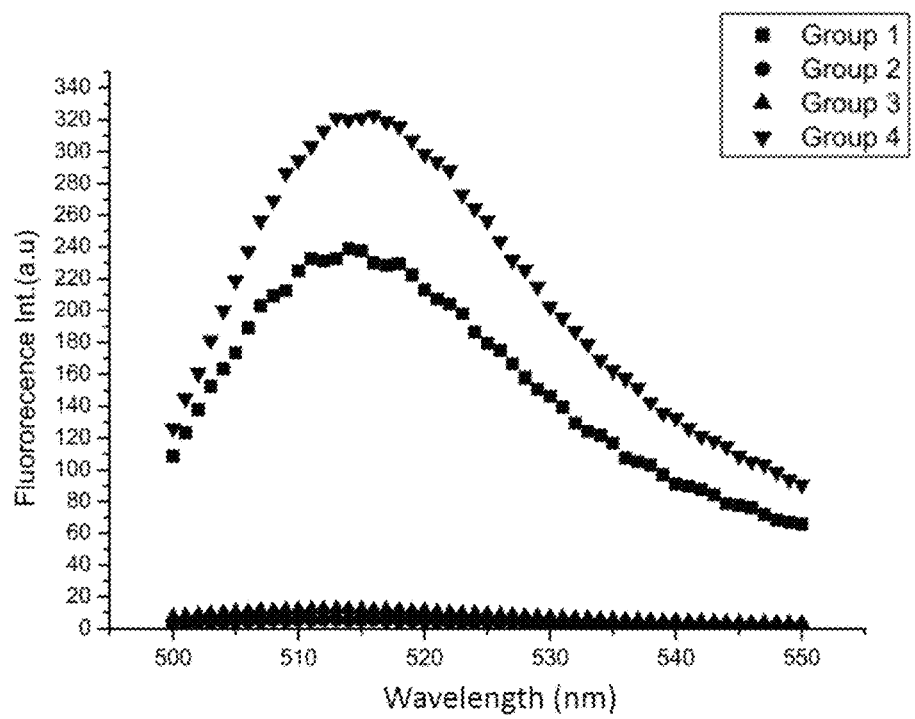
FIG. 13 shows $H_2S_2$ release from compound HP-114 (Group 1) compared with control samples.

After 5 min, 3 ml of the reaction solution from each group were transferred into cells for fluorescence measurement ($\lambda_{ex}$=490 nm). The data is shown in FIG. 13.

Figure 14:
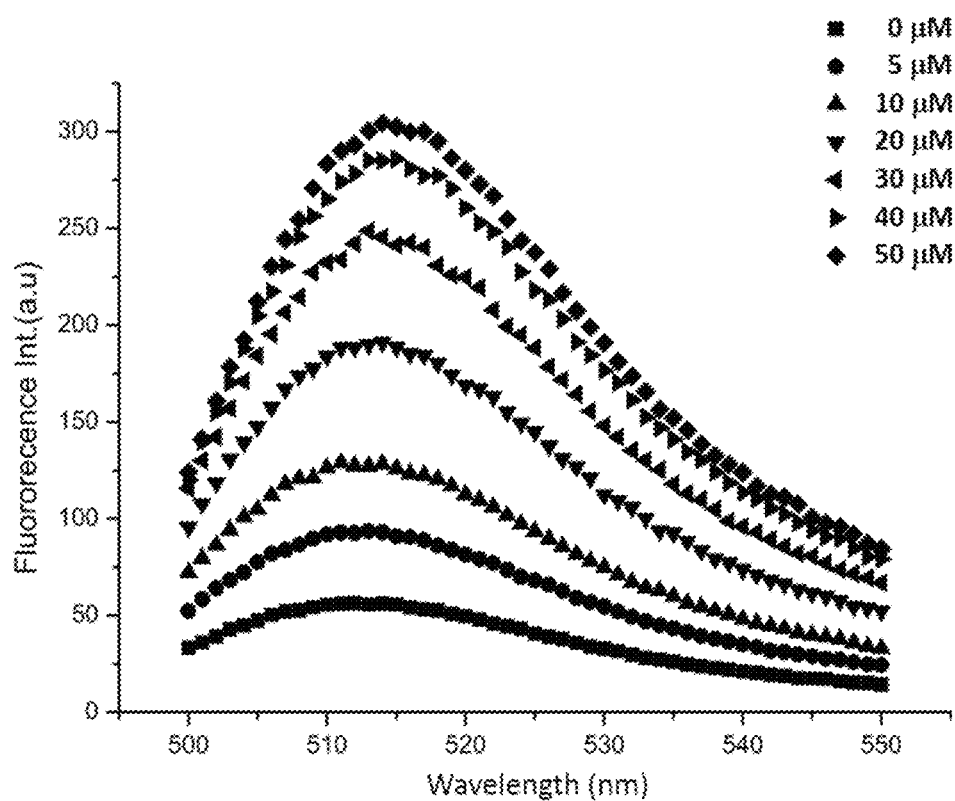
FIG. 14 shows $H_2S_2$ release in reaction mixtures containing varying concentrations of compound HP-114.

Stock solutions of DSP-3 (1 mM) were prepared in $CH_3CN$ and a stock solution of cetrimonium bromide (CTAB, 5 mM) was prepared in EtOH. Stock solutions of HP-114 (10 mM) were prepared in MeOH and 10 units/ml phosphatase was prepared in PBS (pH=7.4). Different volumes of HP-114 stock solution, 20 µl CTAB and 80 µl DSP-3 were mixed with 4 ml 10 units/ml phosphatase. The reaction mixtures were incubated at 37° C. for 60 min and, after cooling down to room temperature, 3 ml of the reaction solution from each group was transferred into cells for fluorescence measurement ($\lambda_{ex}$=490 nm). The data is shown in FIG. 14.

Example 23. Kinetic Study of $H_2$ Release from Compounds HP-113 and HP-114

Figure 15:
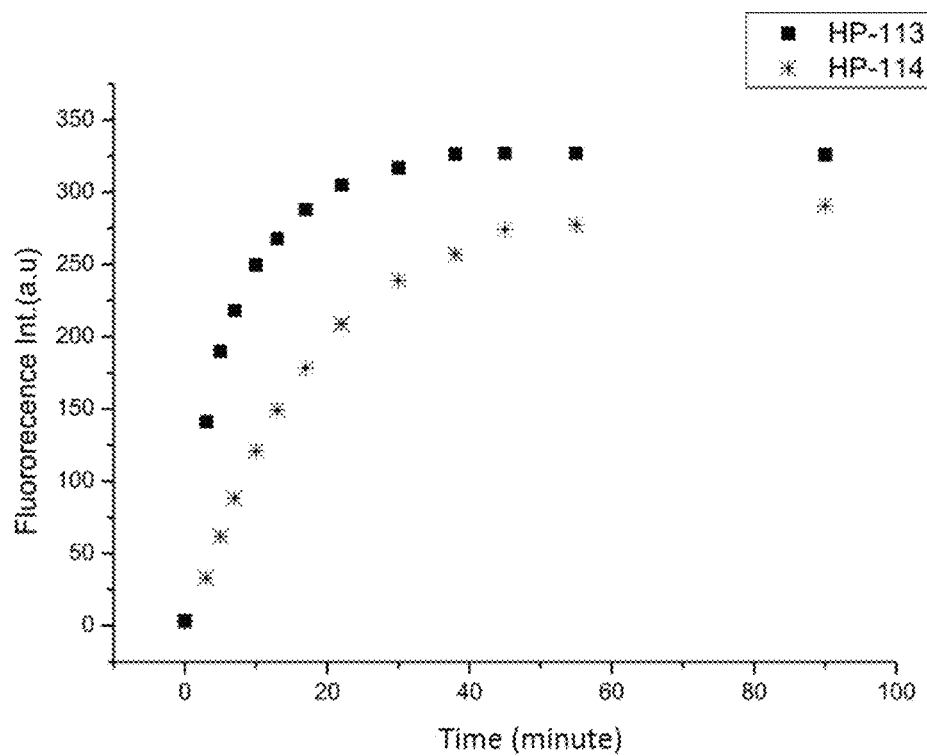
FIG. 15 shows $H_2S_2$ release from compounds HP-113 and HP-114 over time.

Stock solutions of DSP-3 (1 mM) were prepared in $CH_3CN$ and a stock solution of cetrimonium bromide (CTAB, 5 mM) was prepared in EtOH. Stock solutions of HP-113 and HP-114 (10 mM) were prepared in MeOH and 10 units/ml phosphatase was prepared in PBS (pH=7.4). 15 µl HP-113 or HP-114 stock solution, 15 µl CTAB and 75 µl DSP-3 was mixed with 3 ml 10 units/ml phosphatase and was transferred into sealed cells. The reaction mixtures were incubated at 37° C., and the fluorescence intensity was measured at different times ($\lambda_{ex}$=490 nm, ($\lambda_{ex}$=516 nm). The data is shown in FIG. 15.

Although the foregoing has been described in some detail by way of illustration and example for purposes of clarity and understanding, one of skill in the art will appreciate that certain changes and modifications can be practiced within the scope of the appended claims. In addition, each reference provided herein is incorporated by reference in its entirety to the same extent as if each reference was individually incorporated by reference.

What is claimed is:

1. A compound according to Formula I:

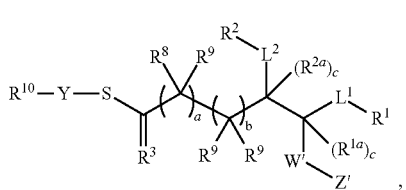

(I)

or a pharmaceutically acceptable salt thereof, wherein:
subscripts a and b are each 1;
each subscript c is 0;
$L^1$ and $L^2$ are each a bond;
$R^1$ and $R^2$ are taken together to form $C_6$-$C_{10}$ aryl, which is optionally substituted with 1-3 $R^4$;
each $R^4$ is independently selected from the group consisting of $C_1$-$C_6$ alkyl, $C_1$-$C_6$ alkoxy, $C_1$-$C_6$ haloalkyl, $C_1$-$C_6$ haloalkoxy, $C_1$-$C_6$ aminoalkyl, $C_1$-$C_6$ aminoalkoxy, $C_3$-$C_6$ cycloalkyl;
$R^3$ is O;
W is O;
Y is a bond and $R^{10}$ is H, or
Y is —S— and $R^{10}$ is selected from the group consisting of $C_1$-$C_6$ alkyl and ($C_6$-$C_{10}$ aryl)-($C_1$-$C_6$ alkyl), wherein $C_1$-$C_6$ alkyl and ($C_6$-$C_{10}$ aryl)-($C_1$-$C_6$ alkyl) are optionally substituted with 1-5 $R^{10a}$, or wherein $C_1$-$C_6$ alkyl and ($C_6$-$C_{10}$ aryl)-($C_1$-$C_6$ alkyl) optionally substituted with —OR' wherein R' is $C_{1-6}$ alkyl;

Z is selected from the group consisting of —C(=O)$R^6$, —C(=O)O$R^6$, —(CH$_2$)$_x$O$R^6$, —(CH$_2$)$_x$C(=O)$R^6$, —(CH$_2$)$_x$OC(=O)$R^6$, —(CH$_2$)$_x$OP(=O)(O$R^6$)$_x$, —OP(=O)(O$R^6$)$_x$, —P(=O)(O$R^6$)$_x$, and $R^7$, wherein each subscript x is independently 0, 1, 2, 3, or 4;

each $R^8$ is independently selected from the group consisting of H and $C_1$-$C_6$ alkyl, each $R^9$ is independently $C_1$-$C_6$ alkyl, wherein one $R^8$ is optionally taken together with one $R^9$ to form a double bond;

each $R^{10a}$ is independently selected from the group consisting of $C_1$-$C_6$ alkyl, —C(=O)O$R^5$, —N$R^5$C(=O)O$R^5$, and a moiety —W—Z;

each $R^5$ is independently selected from the group consisting of H and $C_1$-$C_4$ alkyl;

each $R^6$ is independently selected from the group consisting of $C_1$-$C_4$ alkyl, $C_2$-$C_4$ alkenyl, $C_2$-$C_4$ alkynyl, and $C_3$-$C_4$ cycloalkyl; and $R^7$ is a monosaccharide or a non-steroidal anti-inflammatory drug, wherein the non-steroidal anti-inflammatory drug is selected from the group consisting of ibuprofen, naproxen, sulindac, aceclofenac, salicylates, indomethacin, flurbiprofen, diclofenac, ketorolac, etodolac, fenoprofen, flufenamic acid, ketoprofen, mefenamic acid, diflunisal, tolmetin, ketorolac, aspirin, and lumiracoxib.

2. The compound of claim 1, wherein Z is selected from the group consisting of —C(=O)$R^6$, —C(=O)O$R^6$, —(CH$_2$)$_x$O$R^6$, —(CH$_2$)$_x$C(=O)O$R^6$, —(CH$_2$)$_x$OC(=O)$R^6$, —(CH$_2$)$_x$OP(=O)(O$R^6$)$_x$, —OP(=O)(O$R^6$)$_x$, and —P(=O)(O$R^6$)$_x$, wherein each subscript x is independently 0, 1, 2, 3, or 4.

3. The compound of claim 1, wherein:
Z is —C(=O)$R^6$ and $R^6$ is $C_1$-$C_4$ alkyl; or
wherein Z is $R^7$ and $R^7$ is the non-steroidal anti-inflammatory drug.

4. The compound of claim 1, or a pharmaceutically acceptable salt thereof, having a structure according to Formula Ia:

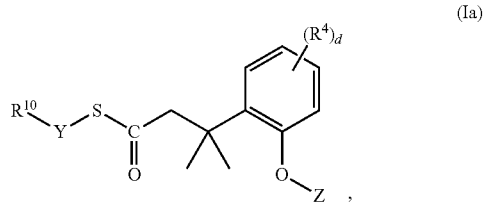

(Ia)

wherein:
subscript d is 0, 1, or 2.

5. The compound of claim 1, or a pharmaceutically acceptable salt thereof, having a structure according to Formula Ib:

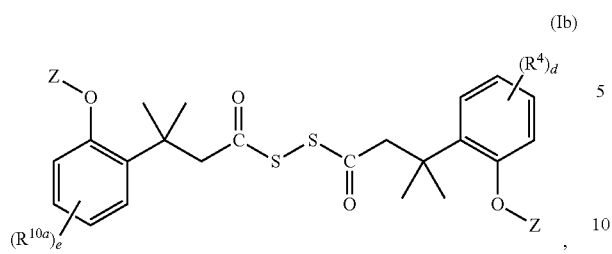
wherein subscripts d and e are independently 0, 1, or 2; and
each $R^{10a}$ is independently selected from the group consisting of $C_1$-$C_6$ alkyl, —C(=O)OR$^5$, and —NR$^5$C(=O)OR$^5$.
6. The compound of claim 1, which is selected from the group consisting of:
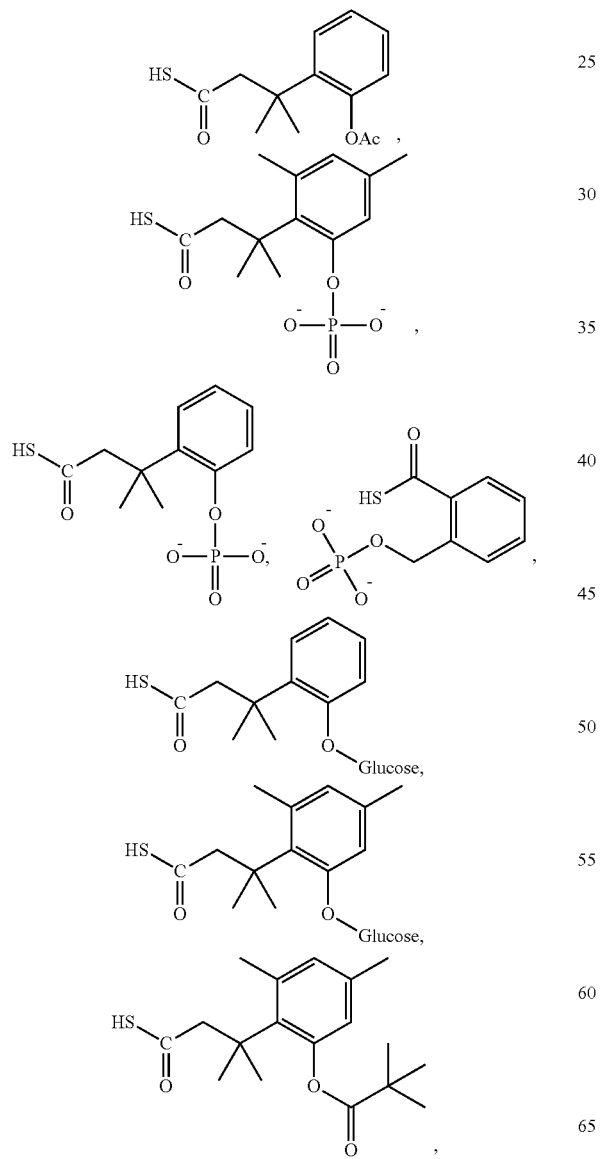
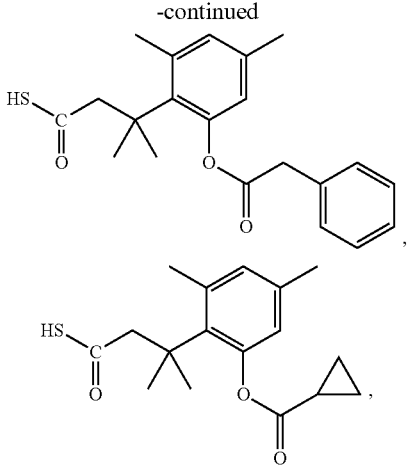
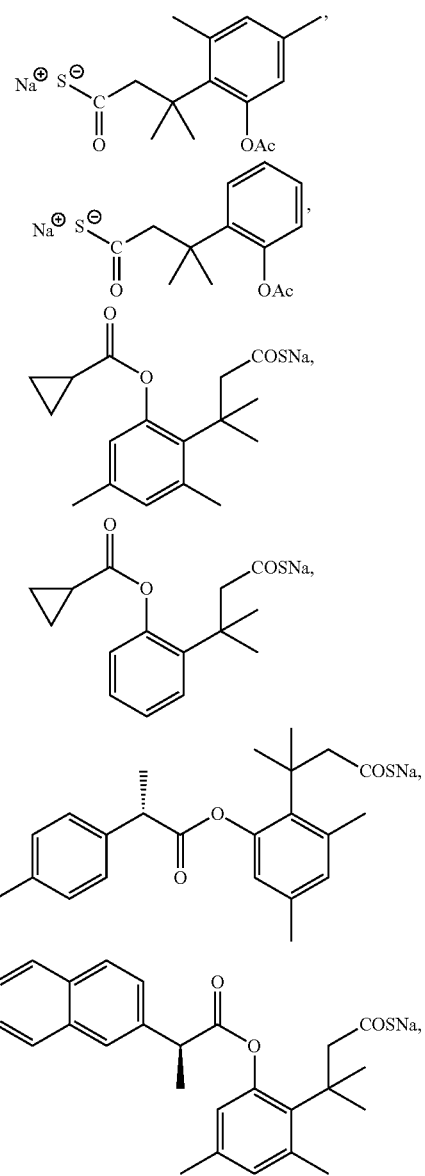

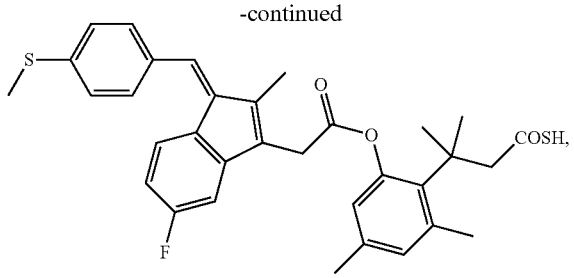
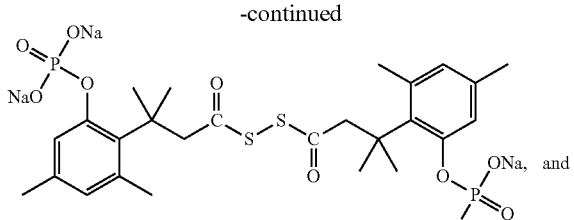
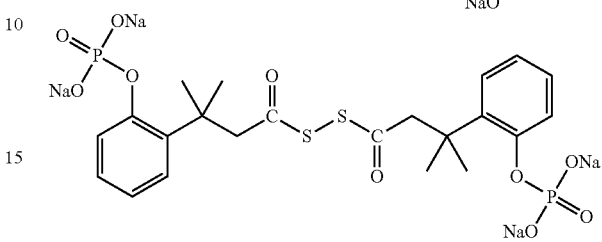
and pharmaceutically acceptable salts thereof.
7. The compound of claim 1, which is
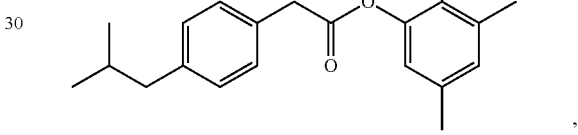
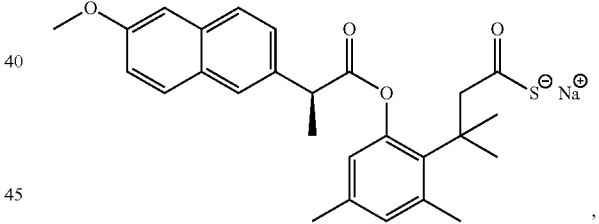
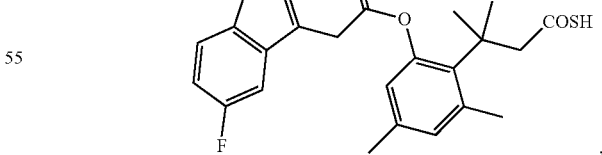
or a pharmaceutically acceptable salt thereof.
8. A pharmaceutical composition comprising a compound according claim 1 and a pharmaceutically acceptable excipient.
* * * * *
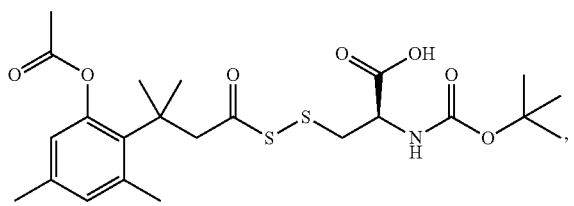

UNITED STATES PATENT AND TRADEMARK OFFICE
CERTIFICATE OF CORRECTION

PATENT NO. : 10,689,335 B2
APPLICATION NO. : 15/563887
DATED : June 23, 2020
INVENTOR(S) : Binghe Wang et al.

It is certified that error appears in the above-identified patent and that said Letters Patent is hereby corrected as shown below:

In the Claims

In Column 73, Lines 43-50 (Approx.), in Claim 1, delete

"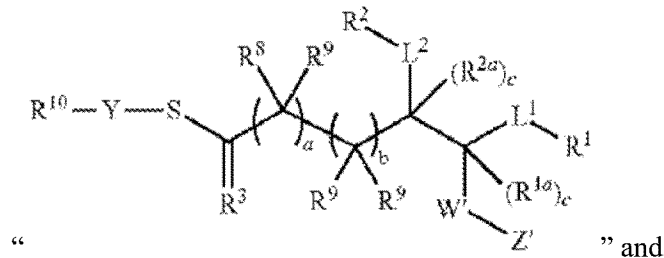" and insert --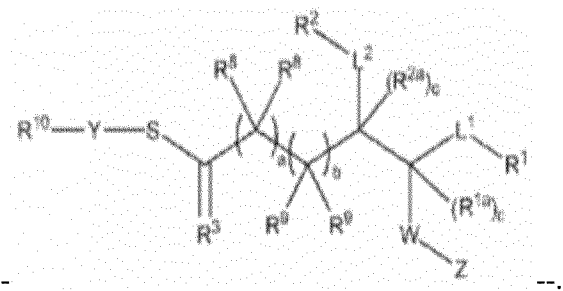--.

In Column 78, Line 63 (Approx.), in Claim 8, after "according" insert -- to --.

Signed and Sealed this
Second Day of July, 2024

Katherine Kelly Vidal
*Director of the United States Patent and Trademark Office*